(12) United States Patent
Chun et al.

(10) Patent No.: US 9,670,309 B2
(45) Date of Patent: Jun. 6, 2017

(54) NOVOLAC-BASED EPOXY COMPOUND, PRODUCTION METHOD FOR SAME, COMPOSITION AND CURED ARTICLE COMPRISING SAME, AND USE FOR SAME

(71) Applicant: KOREA INSTITUTE OF INDUSTRIAL TECHNOLOGY, Cheonan (KR)

(72) Inventors: Hyun-Aee Chun, Seongnam (KR); Yun-Ju Kim, Seoul (KR); Sang-Yong Tak, Busan (KR); Su-Jin Park, Ansan (KR); Sung-Hwan Park, Gunpo (KR)

(73) Assignee: KOREA INSTITUTE OF INDUSTRIAL TECHNOLOGY, Cheonan (KR)

( * ) Notice: Subject to any disclaimer, the term of this patent is extended or adjusted under 35 U.S.C. 154(b) by 0 days.

(21) Appl. No.: 14/413,226

(22) PCT Filed: Jul. 5, 2013

(86) PCT No.: PCT/KR2013/006005
§ 371 (c)(1),
(2) Date: Jan. 6, 2015

(87) PCT Pub. No.: WO2014/007582
PCT Pub. Date: Jan. 9, 2014

(65) Prior Publication Data
US 2015/0203626 A1 Jul. 23, 2015

(30) Foreign Application Priority Data

Jul. 6, 2012 (KR) ............... 10-2012-0074196
Jul. 4, 2013 (KR) ............... 10-2013-0078347

(51) Int. Cl.
| | | |
|---|---|---|
| *C08G 59/20* | (2006.01) | |
| *C08G 59/14* | (2006.01) | |
| *C08G 77/00* | (2006.01) | |
| *C08L 63/04* | (2006.01) | |
| *C08L 83/00* | (2006.01) | |
| *C08K 7/00* | (2006.01) | |
| *C08K 7/04* | (2006.01) | |
| *C07D 303/04* | (2006.01) | |
| *C07F 7/18* | (2006.01) | |
| *C08K 3/36* | (2006.01) | |
| *C08K 7/14* | (2006.01) | |
| *C08G 59/08* | (2006.01) | |

(52) U.S. Cl.
CPC ....... *C08G 59/1494* (2013.01); *C07D 303/04* (2013.01); *C07F 7/1836* (2013.01); *C08G 59/08* (2013.01); *C08G 59/1433* (2013.01); *C08K 3/36* (2013.01); *C08K 7/14* (2013.01); *C08L 63/04* (2013.01); *C08L 2205/02* (2013.01)

(58) Field of Classification Search
None
See application file for complete search history.

(56) References Cited

U.S. PATENT DOCUMENTS

| | | | |
|---|---|---|---|
| 4,220,513 A | 9/1980 | Green et al. | |
| 4,292,151 A | 9/1981 | Inata et al. | |
| 4,789,711 A | 12/1988 | Monnier et al. | |
| 5,019,607 A * | 5/1991 | Coltrain ................. | C08G 18/58 523/435 |
| 5,300,588 A | 4/1994 | Shiobara et al. | |
| 5,336,786 A | 8/1994 | Shiobara et al. | |
| 6,087,513 A | 7/2000 | Liao et al. | |
| 6,160,040 A | 12/2000 | Ghosh | |
| 2003/0078322 A1 | 4/2003 | Honda et al. | |
| 2004/0241331 A1 | 12/2004 | Durairaj et al. | |
| 2005/0284087 A1* | 12/2005 | Yang ..................... | B82Y 30/00 52/741.1 |

(Continued)

FOREIGN PATENT DOCUMENTS

| | | |
|---|---|---|
| CN | 1293685 A | 5/2001 |
| CN | 1303382 A | 7/2001 |

(Continued)

OTHER PUBLICATIONS

Nobuo Suzuki et al., "Concise Encyclopedia of Polymer Science and Engineering", Polymer Dictionary, 1994, pp. 455-456, Maruzen Inc., Japan.
Extended European Search Report for European Application No. 13813009.1 dated Feb. 12, 2016.
Tsung-Han Ho et al., "Modification of epoxy resin with siloxane containing phenol aralkyl epoxy resin for electronic encapsulation application" European Polymer Journal, 2001, pp. 267-274, vol. 37, Elsevier Science Ltd.
Barry Arkles, "Silane Coupling Agents: Connecting Across Boundaries", 2006, pp. 1-60, Gelest Inc., http://www.gelest.de/goods/pdf/couplingagents.pdf.
Chinese Office Action for CN Application No. 201280053687.4, dated May 20, 2015.
Extended European Search Report for European Patent Application No. 13796871.5 dated Dec. 9, 2015.

(Continued)

*Primary Examiner* — Michael J Feely

(57) ABSTRACT

A novolac epoxy compound having an alkoxysilyl group of which composite has low CTE and increase of glass transition temperature, and requiring no coupling agent, a production method thereof, an epoxy composition including the same and a cured article thereof, are provided. A novolac epoxy compound having an alkoxysilyl group of Formulae I-1 to I-4, a production method of the novolac epoxy compound having an alkoxysilyl group by the epoxidation, alkenylation and alkoxysilylation of a novolac epoxy compound, a production method of the novolac epoxy compound having an alkoxysilyl group by the epoxidation and alkoxysilylation of a novolac epoxy compound, an epoxy composition including the novolac epoxy compound having an alkoxysilyl group, and a cured article, are provided. The cured article, i.e., the composite of the epoxy composition has improved chemical bonding efficiency due to alkoxysilyl groups. Low CTE and high glass transition temperature are exhibited.

17 Claims, 2 Drawing Sheets

(56) References Cited

U.S. PATENT DOCUMENTS

| | | | |
|---|---|---|---|
| 2007/0100043 A1 | 5/2007 | Shiono | |
| 2007/0282081 A1 | 12/2007 | Ichiroku | |
| 2008/0221238 A1 | 9/2008 | Su et al. | |
| 2009/0004484 A1 | 1/2009 | Kim et al. | |
| 2009/0286924 A1* | 11/2009 | Tsuchida | C07F 7/1836 524/588 |
| 2011/0020555 A1 | 1/2011 | Wothke et al. | |
| 2011/0082321 A1 | 4/2011 | Sakurai et al. | |
| 2011/0143092 A1 | 6/2011 | Asai et al. | |
| 2011/0319589 A1 | 12/2011 | Takeyama et al. | |
| 2012/0041102 A1 | 2/2012 | Chun et al. | |
| 2012/0153512 A1 | 6/2012 | Sugimoto et al. | |
| 2012/0292487 A1 | 11/2012 | Yukawa et al. | |
| 2012/0295199 A1 | 11/2012 | Takeyama et al. | |
| 2012/0315765 A1 | 12/2012 | Nakajima et al. | |

FOREIGN PATENT DOCUMENTS

| | | |
|---|---|---|
| CN | 1784462 A | 6/2006 |
| CN | 101701058 A | 5/2010 |
| EP | 0 618 246 A2 | 10/1994 |
| EP | 1114834 A1 | 11/2001 |
| EP | 2 119 721 A1 | 11/2009 |
| EP | 2 767 535 A2 | 8/2014 |
| JP | 61-272244 A | 12/1986 |
| JP | 62-050312 A | 3/1987 |
| JP | S62-292828 A | 12/1987 |
| JP | S63-280720 A | 11/1988 |
| JP | 06-345847 A | 12/1994 |
| JP | 07-258240 A | 10/1995 |
| JP | 08-193091 A | 7/1996 |
| JP | 2003-040970 A | 2/2003 |
| JP | 2003-048953 A | 2/2003 |
| JP | 2003-055435 A | 2/2003 |
| JP | 2003-141933 A | 5/2003 |
| JP | 2006-012784 A | 1/2006 |
| JP | 2006-137800 A | 6/2006 |
| JP | 2006-176732 A | 7/2006 |
| JP | 2007-126496 A | 5/2007 |
| JP | 2010-003897 A | 1/2010 |
| JP | 2010-065161 A | 3/2010 |
| JP | 2010-520952 A | 6/2010 |
| JP | 2011-057755 A | 3/2011 |
| JP | 2011-208120 A | 10/2011 |
| JP | 2012-246422 A | 12/2012 |
| JP | 2012-246425 A | 12/2012 |
| KR | 10-2000-0062386 A | 10/2000 |
| KR | 10-2005-0058727 A | 6/2005 |
| KR | 10-2006-0077959 A | 7/2006 |
| KR | 10-0835784 B1 | 6/2008 |
| KR | 10-0929380 B1 | 12/2009 |
| KR | 10-2011-0008212 A | 1/2011 |
| WO | WO 99/62894 A2 | 12/1999 |
| WO | WO 2010/092947 A1 | 8/2010 |
| WO | WO 2011/093188 A1 | 8/2011 |
| WO | WO 2011/093236 A1 | 8/2011 |
| WO | WO 2011/102470 A1 | 8/2011 |
| WO | WO 2012/070637 A1 | 5/2012 |
| WO | WO 2013/180375 A1 | 12/2013 |

OTHER PUBLICATIONS

Tahseen Razzaq et al., "Investigating the Existence of Nonthermal/Specific Microwave Effects Using Silicon Carbide Heating Elements as Power Modulators", The Journal of Organic Chemistry, 2008, pp. 6321-6329, vol. 73, No. 16, American Chemical Society.

Zhang et al., "Characterization of Siliconized Diallyl Bisphenol A Type Epoxy Resin and Study on its Curing Properties," Chemistry and Adhesion, Jun. 2006, pp. 369-371 & 375, vol. 28, No. 6.

Lei Xue et al., "Precise Synthesis of Poly(silphenylenesiloxane)s with Epoxy Side Functional Groups by Tris(pentafluorophenyl)borane as a Catalyst," Polyer Journal, 2007, pp. 379-388, vol. 39, No. 4.

Chinese Office Action for Chinese Patent Application No. 201280052291.8 dated Oct. 28, 2015.

Chinese Office Action for Chinese Patent Application No. 201380046568.0 dated Nov. 2, 2015.

Extended European Search Report for European Patent Application No. 13772355.7 dated Oct. 16, 2015.

* cited by examiner

NOVOLAC-BASED EPOXY COMPOUND, PRODUCTION METHOD FOR SAME, COMPOSITION AND CURED ARTICLE COMPRISING SAME, AND USE FOR SAME

TECHNICAL FIELD

The present invention relates to a novolac epoxy compound containing an alkoxysilyl group (hereinafter 'novolac epoxy compound') exhibiting good heat resistance property in a composite thereof, a production method of the same, a composition including the same, a cured article of the composition, and a use of the composition. More particularly, the present invention relates to a novel novolac epoxy compound exhibiting good heat resistance property, in particular, low thermal expansion property and increase of glass transition temperature (including a glass transition temperature-less (Tg-less) effects, which means that the composite does not have a glass transition temperature) and flame retardancy, and not requiring a separate coupling agent, a production method of the same, a composition including the same, a cured article of the composition, and a use of the composition.

BACKGROUND ART

The Coefficient of Thermal Expansion (CTE) of a polymer material—specifically, an epoxy resin—is about 50 to 80 ppm/° C., a significantly higher several to ten times than the CTE of a inorganic material such as ceramic material or a metal (for example, the CTE of silicon is 3 to 5 ppm/° C. and the CTE of copper is 17 ppm/° C.). Thus, when the polymer material is used in conjunction with an inorganic material or metal in a semiconductor, a display, or the like, the properties and processability of the polymer material may be significantly limited due to the mismatch in the coefficients of thermal expansion of the polymer material and the inorganic material or the metal material. In addition, during semiconductor packaging in which a silicon wafer and a polymer substrate are used side by side, or during a coating in which a polymer film is coated with an inorganic shielding layer to impart gas barrier property, product defects such as the generation of cracks in an inorganic layer, the warpage of a substrate, the peeling-off of a coating layer, the failure of a substrate, and the like, may be generated due to a large mismatch of coefficient of thermal expansion (CTE-mismatch) between constituent elements upon the changes in processing and/or applied temperature conditions.

Because of the high CTE of the polymer material and the resultant dimensional change of the polymer material, the development of technologies such as next generation semiconductor substrates, printed circuit boards (PCBs), packaging, organic thin film transistors (OTFTs), and flexible display substrates may be limited. Particularly, currently, in the semiconductor and PCB fields, designers are facing challenges in the design of next generation parts requiring high degrees of integration, miniaturization, flexibility, performance, and the like, in securing processability and reliability in parts due to polymer materials having significantly high CTE as compared to metal/ceramic materials. In other words, due to the high thermal expansion property of the polymer material at processing temperatures, defects may be generated, processability may be limited, and the design of the parts and the securing of processability and reliability therein may be objects of concern. Accordingly, improved thermal expansion property or dimensional stability of the polymer material is necessary in order to secure processability and reliability in electronic parts.

In general, in order to improve thermal expansion property—i.e., to obtain a low CTE value in a polymer material such as an epoxy resin, (1) a method of making a composite of the epoxy resin with inorganic particles (an inorganic filler) and/or fabrics and (2) a method of designing and synthesizing a novel epoxy resin with a decreased CTE have been used.

When the composite of the epoxy compound with the inorganic particles as the filler is formed in order to improve thermal expansion property, a large amount of inorganic silica particles, having a diameter of about 2 to 30 μm are required to be used to obtain the significant decrease of CTE. However, due to the addition of the large amount of inorganic particles, the processability and performance of the parts may be deteriorated. That is, the presence of the large amount of inorganic particles may decrease fluidity, and voids may be generated during the filling of narrow spaces. In addition, the viscosity of the material may increase exponentially due to the addition of the inorganic particles. Further, the size of the inorganic particles tends to decrease due to the miniaturization of semiconductor structure. When a filler having a particle size of 1 μm or less is used, the decrease in fluidity (increase in viscosity) may be worsened. When inorganic particles having a large average particle diameter are used, the frequency of insufficient filling in the case of a composition including a resin and the inorganic particles may increase. While the CTE of the composite may be decreased significantly when a composition including an organic resin and a fiber as the filler is used, it may remain still high as compared to that of a silicon chip or the like.

As described above, the manufacturing of highly integrated and high performance electronic parts for next generation semiconductor substrates, PCBs, and the like, may be limited due the limitations in the composite technology of epoxy compounds. Thus, the development of a epoxy composite having improved heat resistance property—namely, a low CTE and a high glass transition temperature—and good crosslinking density is required to overcome the a lack of heat resistance property due to a high CTE and poor processability of a common thermosetting polymer composite.

DISCLOSURE

Technical Problem

An aspect of the present invention may provide a novel novolac epoxy compound, a composite of which exhibits good heat resistance property, particularly, a low Coefficient of Thermal Expansion (CTE) and high glass transition temperature property, and a cured article of which exhibits good flame retardancy.

An aspect of the present invention may also provide a production method of the novel novolac epoxy compound, a composite of which exhibits good heat resistance property, particularly, a low CTE and high glass transition temperature property, and a cured article of which exhibits good flame retardancy.

An aspect of the present invention may also provide an epoxy composition, a composite of which exhibits good heat resistance property, particularly, a low CTE and high glass transition temperature property, and a cured article of which exhibits good flame retardancy.

Further, an aspect of the present invention may also provide a cured article of the epoxy composition, a composite of which exhibits good heat resistance property, particularly, a low CTE and high glass transition temperature property, and a cured article of which exhibits good flame retardancy.

In addition, an aspect of the present invention may also provide a use of an epoxy composition according to an embodiment of the present invention.

Technical Solution

According to a first aspect of the present invention, a novolac epoxy compound having at least one alkoxysil group selected from the group consisting of the following Formulae I-1 to I-4 is provided.

[Formula I-1]

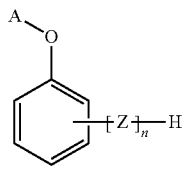

In the above Formula I-1, Z is one selected from the group consisting of the following Formulae 1A to 1F.

1A

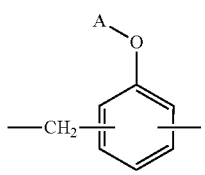

1B

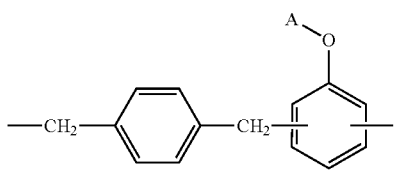

1C

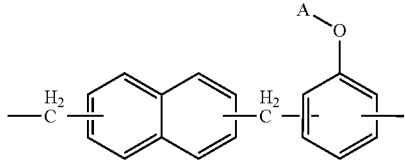

1D

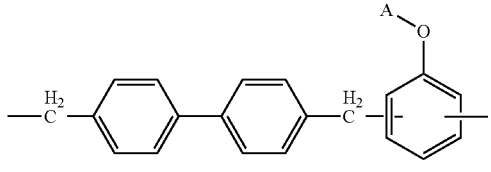

1E

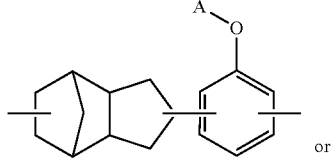

or

1F

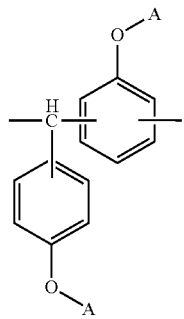

[I-2]

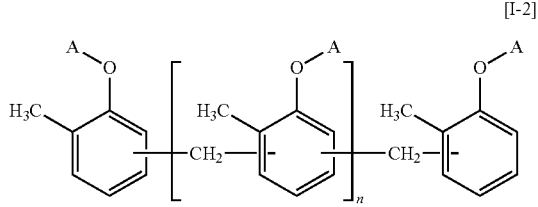

[I-3]

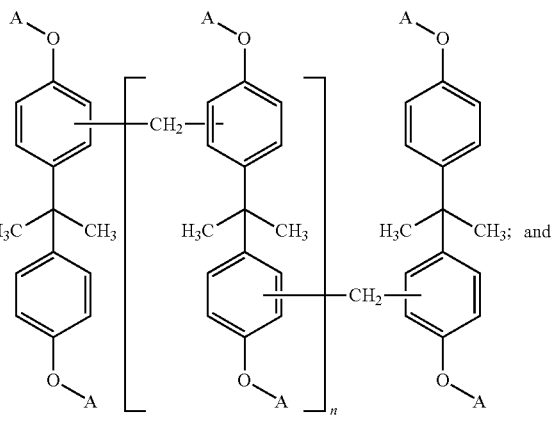

[I-4]

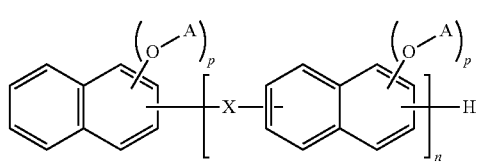

In the above Formula I-4, x is

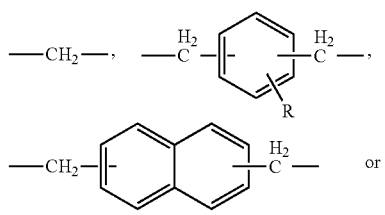

or

-continued

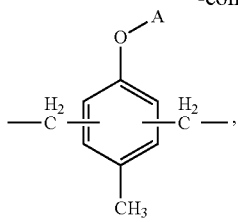

and in

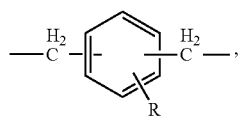

R is a linear or branched alkyl group of C1-C10.

In the above Formulae I-1 to I-4, at least two of a plurality of A have the structure of the following Formula A2, and at least one of the plurality of A has the structure of the following Formula A3 or A4. In the case that at least one of A is A3, the remainder thereof are the following Formula B3 or hydrogen, and in the case that at least one of A is A4, the remainder thereof are hydrogen. In the above Formula I-1, in the case that Z is 1A to 1E, n is an integer of at least 2 or higher, and in the case that Z is 1F, n is an integer of at least 1. In the above Formulae I-2 and I-3, n is an integer of at least 1. In the above Formula I-4, in the case that x is

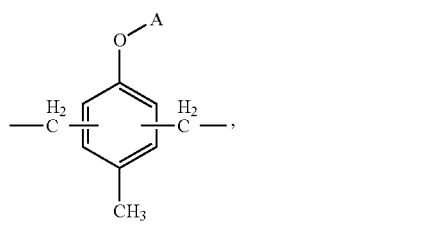

n is an integer of at least 2, and in the case that x is

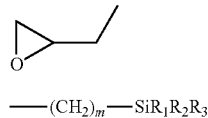

n is an integer of at least 1. In the above Formula I-4, p is 1 or 2.

[Formula A2]

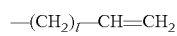

—(CH$_2$)$_m$—SiR$_1$R$_2$R$_3$  [Formula A3]

—CONH(CH$_2$)$_m$—SiR$_1$R$_2$R$_3$  [Formula A4]

In the above Formulae A3 and A4, at least one of R$_1$ to R$_3$ is an alkoxy group having 1 to 5 carbon atoms, and the remainder thereof are an alkyl group having 1 to 10 carbon atoms, the alkoxy group and the alkyl group are a linear or a branched, and m is an integer from 3 to 10.

—(CH$_2$)$_l$—CH=CH$_2$  [Formula B3]

In the above Formula B3, l is an integer from 1 to 8.

According to a second aspect of the present invention, at least one of R$_1$ to R$_3$ may be an ethoxy group in the above Formulae A3 and A4 in the novolac epoxy compound having at least one alkoxysilyl group according to the first aspect.

According to a third aspect of the present invention, a production method of a novolac epoxy compound having at least one alkoxysilyl group selected from the group consisting of Formulae I-1 to I-4, is provided. The production method includes a first step of preparing one intermediate of the following Formulae IB-1 to IB-4 by reacting one starting material of the following Formulae IA-1 to IA-4, an alkenyl compound of the following Formula II and epichlorohydrin in the presence of a base and an optional solvent; and a second step of preparing one compound of Formulae I-1 to I-4 having a structure of Formula A3 by reacting one intermediate of the above Formulae IB-1 to IB-4 and alkoxysilane of the following Formula IIIA in the presence of a platinum catalyst and an optional solvent.

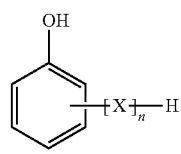
[Formula IA-1]

In the above Formula IA-1, X is one selected from the group consisting of the following Formulae 2A to 2F.

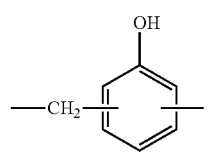
2A

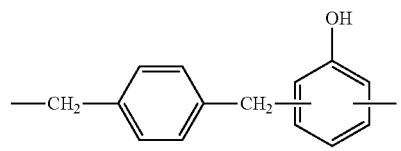
2B

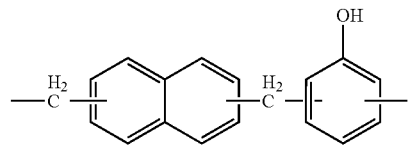
2C

-continued

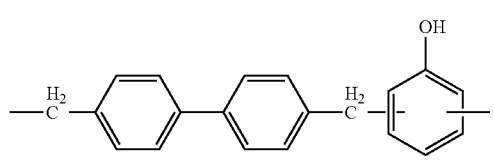
2D

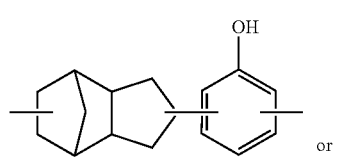
2E or

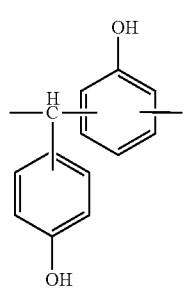
2F

[Formula IA-2]
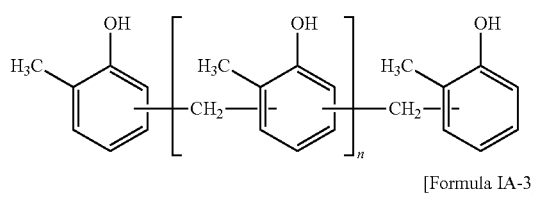

[Formula IA-3]
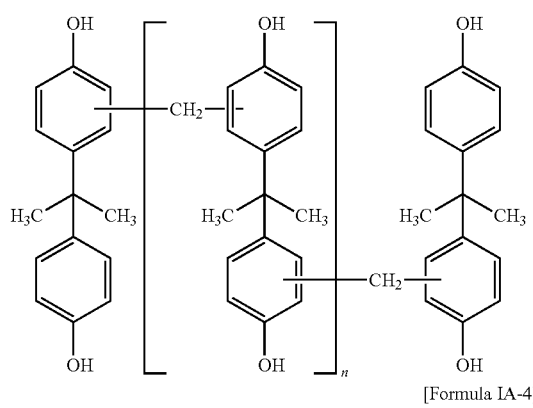

[Formula IA-4]
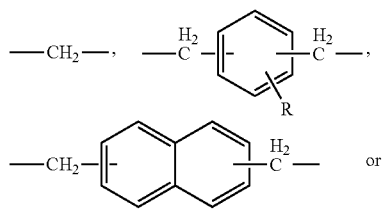

In the above Formula IA-4, x1 is

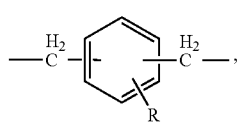

and in

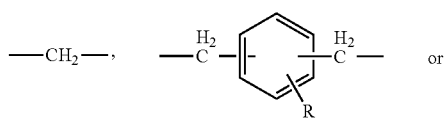

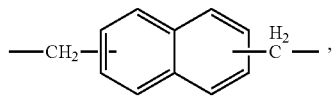

R is a linear or a branched alkyl group of C1-C10.

In the above Formula IA-1, in the case that X is 2A to 2E, n is an integer of at least 2, and in the case that X is 2F, n is an integer of at least 1. In the above Formulae IA-2 and IA-3, n is an integer of at least 1. In the above Formula IA-4, in the case that x1 is

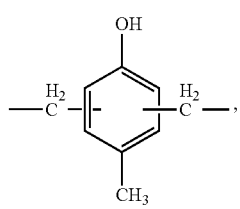

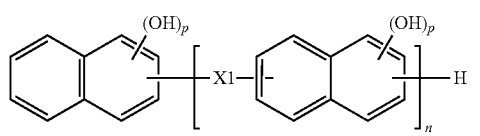

n is an integer of at least 2, and in the case that x1 is

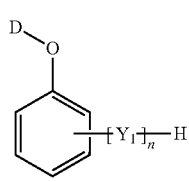

n is an integer of at least 1. In the above Formula IA-4, p is 1 or 2.

[Formula IB-1]

In the above Formula IB-1, $Y_1$ is one selected from the group consisting of the following Formulae 3A to 3F.

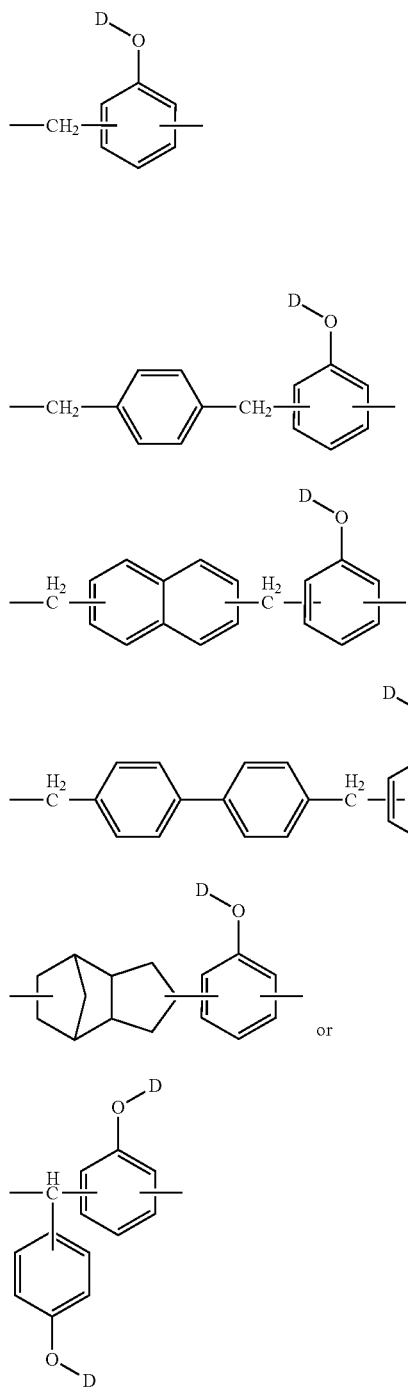

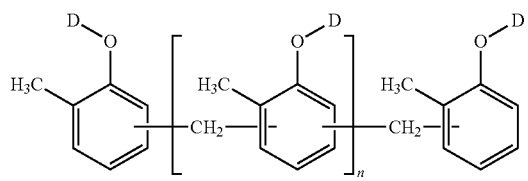

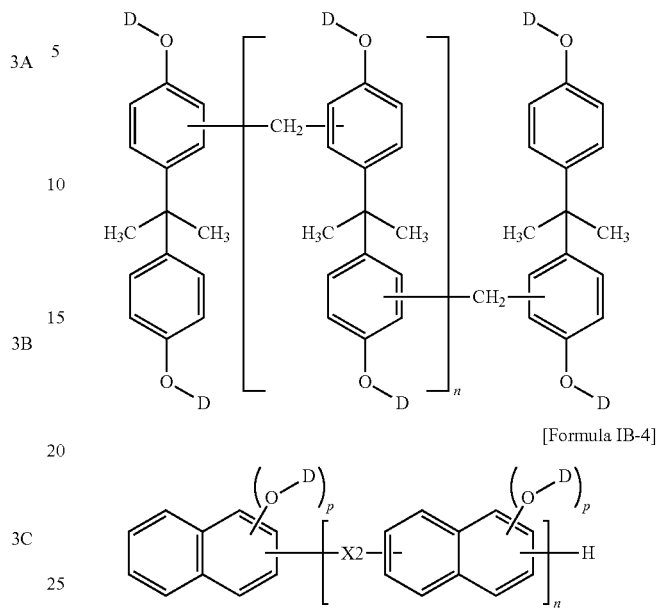

In the above Formula IB-4, x2 is

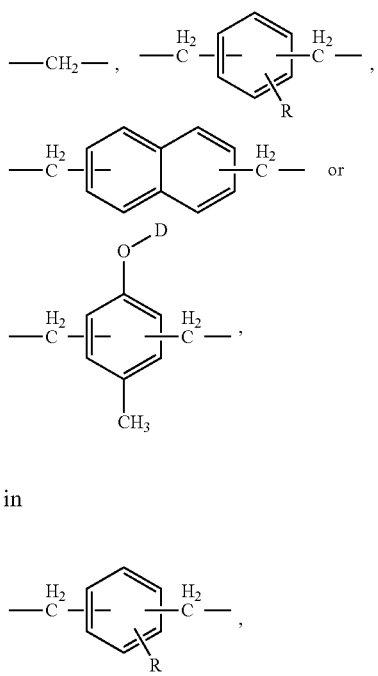

and in

R is a linear or branched alkyl group of C1-C10.

In the above Formula IB-1 to IB-4, at least two of a plurality of D may be the following Formula B2, at least one of D may be the following Formula B3 and the remainder may be hydrogen. In the above Formulae IB-1, in the case that Y1 is 3A to 3E, n is an integer of at least 2, and in the case that Y1 is 3F, n is an integer of at least 1. In the above Formulae IB-2 and IB-3, n is an integer of at least 1. In the above Formula IB-4, in the case that x2 is

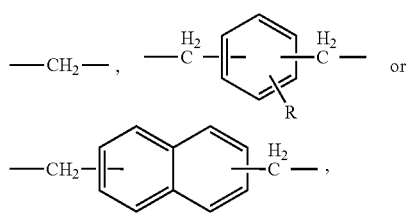 or

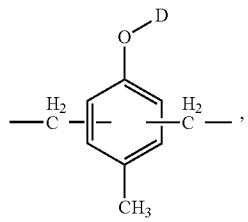

n is an integer of at least 2, and in the case that x2 is

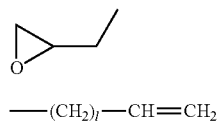

n is an integer of at least 1. In the above Formula IB-4, p is 1 or 2.

[Formula B2]

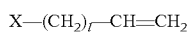

[Formula B3]

—(CH$_2$)$_l$—CH=CH$_2$

In the above Formula B3, l is an integer from 1 to 8.

X—(CH$_2$)$_l$—CH=CH$_2$ [Formula II]

In the above Formula II, l is an integer from 1 to 8, X is a halide such as Cl, Br or I, —O—SO$_2$—CH$_3$, —O—SO$_2$—CF$_3$, or —O—SO$_2$—C$_6$H$_4$—CH$_3$.

HSiR$_a$R$_b$R$_c$ [Formula IIIA]

In the above Formula IIIA, at least one of R$_a$ to R$_c$ is an alkoxy group of C1-C5, and the remainder are an alkyl group of C1-C10, and the alkoxy group and the alkyl group may be a linear or a branched.

[Formula I-1]

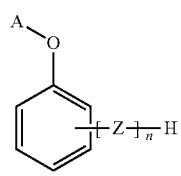

In the above Formula I-1, Z is one selected from the group consisting of the following Formulae 1A to 1F.

1A

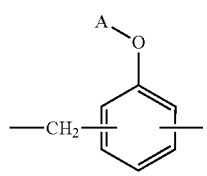

1B

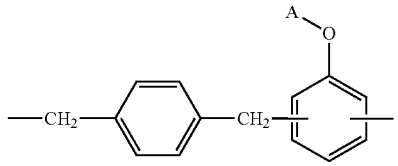

1C

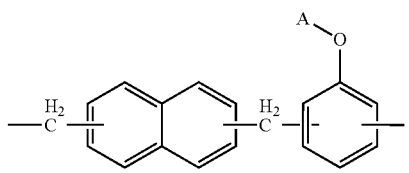

1D

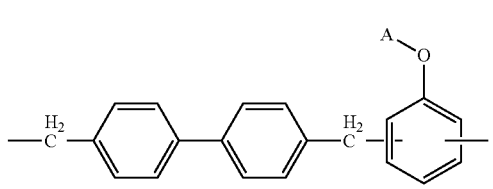

1E

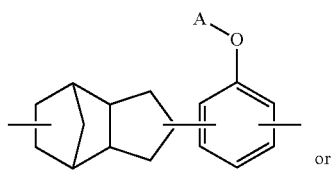 or

1F

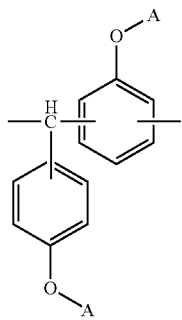

[I-2]

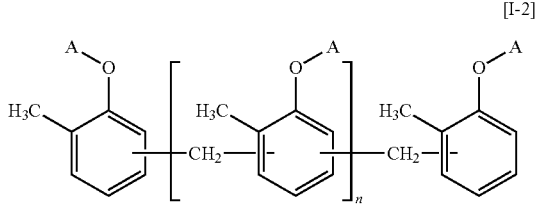

-continued

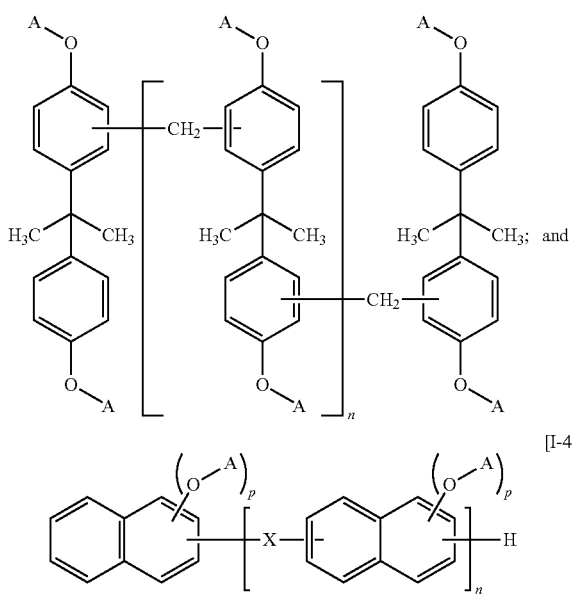
[I-3]

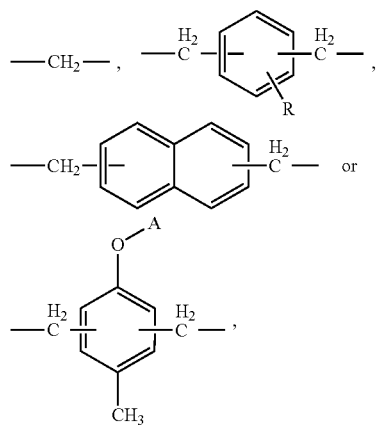
[I-4]

In the above Formula I-4, x is

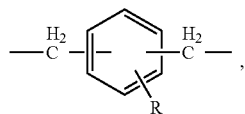

and in

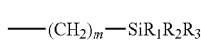,

R is a linear or branched alkyl group of C1-C10.

In the above Formulae I-1 to I-4, at least two of a plurality of A have the structure of the following Formula A2, and at least one of A has the following Formula A3, and the remainder thereof have the following Formula B3 or hydrogen. In the above Formula I-1, in the case that Z is 1A to 1E, n is an integer of at least 2, and in the case that Z is 1F, n is an integer of at least 1. In the above Formulae I-2 and I-3, n is an integer of at least 1. In the above Formula I-4, in the case that x is

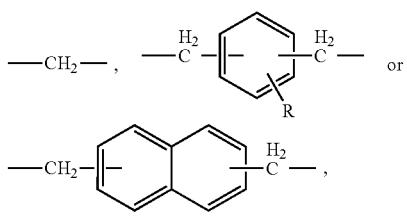

n is an integer of at least 2, and in the case that x is

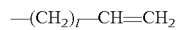, n is an integer of at least 1. In the above Formula I-4, p is 1 or 2.

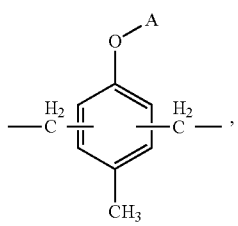 [Formula A2]

—(CH$_2$)$_m$—SiR$_1$R$_2$R$_3$ [Formula A3]

In the above Formulae A3, at least one of $R_1$ to $R_3$ is an alkoxy group having 1 to 5 carbon atoms, and the remainder thereof are an alkyl group having 1 to 10 carbon atoms, the alkoxy group and the alkyl group are a linear or a branched, and m is an integer from 3 to 10.

—(CH$_2$)$_l$—CH=CH$_2$ [Formula B3]

In the above Formula B3, l is an integer from 1 to 8.

According to a fourth aspect of the present invention, a reaction in the first step may be performed using 0.1 to 10 equivalents of an alkylene group of the alkenyl compound of the above Formula II and 1 to 10 equivalents of an epoxy group of the epichlorohydrin with respect to 1 equivalent of a hydroxyl group of one starting material of the above Formulae IA-1 to IA-4 in the production method of the novolac epoxy compound having at least one alkoxysilyl group according to the third aspect.

According to a fifth aspect of the present invention, a reaction in the first step may be performed at −20° C. to 100° C. for 1 to 120 hours in the production method of the novolac epoxy compound having at least one alkoxysilyl group according to the third aspect.

According to a sixth aspect of the present invention, a reaction in the second step may be performed using 0.1 to 5 equivalents of the alkoxysilane with respect to 1 equivalent of an alkenyl group of one intermediate of the above Formulae IB-1 to IB-4 in the production method of the novolac epoxy compound having at least one alkoxysilyl group according to the third aspect.

According to a seventh aspect of the present invention, a reaction in the second step may be performed at −20° C. to 120° C. for 1 to 72 hours in the production method of the novolac epoxy compound having at least one alkoxysilyl group according to the third aspect.

According to an eighth aspect of the present invention, a production method of a novolac epoxy compound selected from the group consisting of Formulae I-1 to I-4, is provided. The production method includes a first step of preparing one intermediate of the following Formulae IC-1 to IC-4 by reacting one starting material of the following Formulae IA-1 to IA-4 and epichlorohydrin in the presence of a base and an optional solvent; and a second step of preparing one compound of Formulae I-1 to I-4 having a structure of Formula A4 by reacting the one intermediate of the above Formulae IC-1 to IC-4 and alkoxysilane of the following Formula IIIB in the presence of an optional base and an optional solvent.

[Formula IA-1]

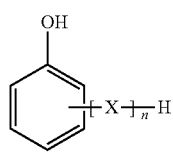

In the above Formula IA-1, X is one selected from the group consisting of the following Formulae 2A to 2F.

2A

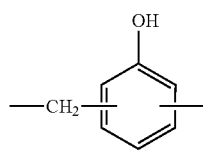

2B

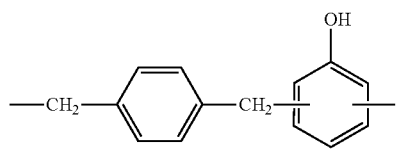

2C

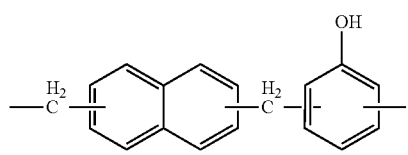

2D

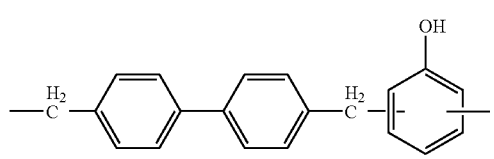

2E

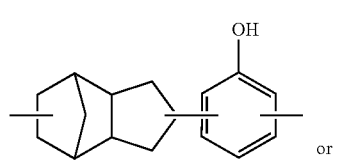

or

2F

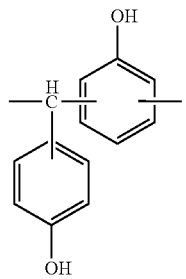

[Formula IA-2]

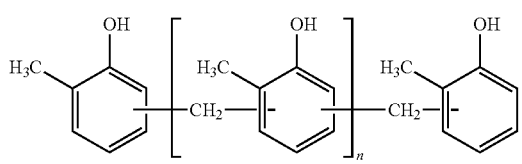

[Formula IA-3]

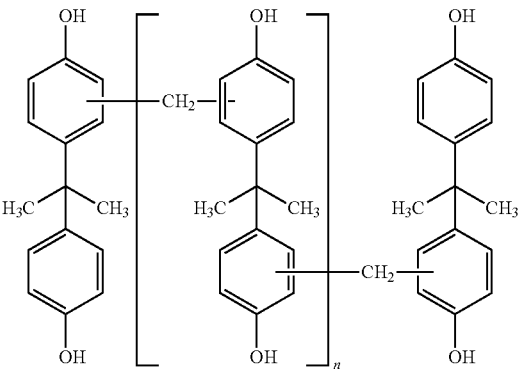

[Formula IA-4]

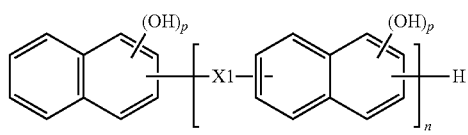

In the above Formula IA-4, x1 is

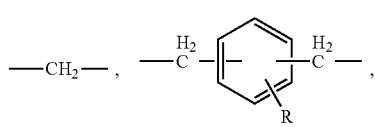

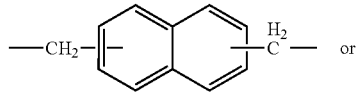

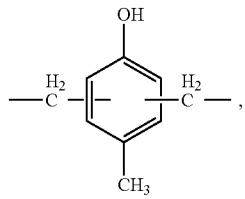

and in

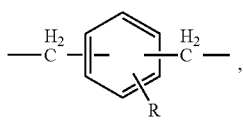

R is a linear or a branched alkyl group of C1-C10.

In the above Formula IA-1, in the case that X is 2A to 2E, n is an integer of at least 2, and in the case that X is 2F, n is an integer of at least 1. In the above Formulae IA-2 and IA-3, n is an integer of at least 1. In the above Formula IA-4, in the case that x1 is

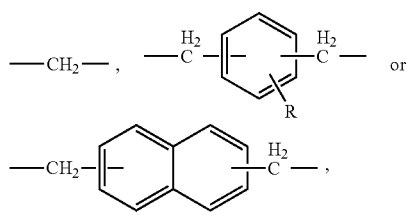

n is an integer of at least 2, and in the case that x1 is

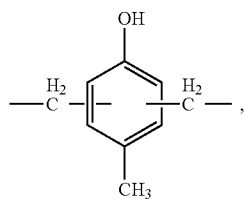

n is an integer of at least 1. In the above Formula IA-4, p is 1 or 2.

[Formula IC-1]

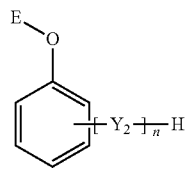

In the above Formula IC-1, $Y_2$ is one selected from the group consisting of the following Formulae 4A to 4F.

4A

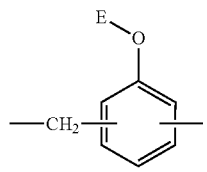

4B

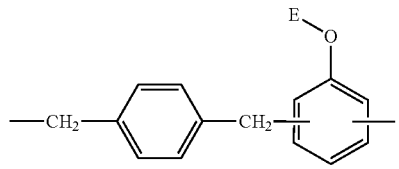

4C

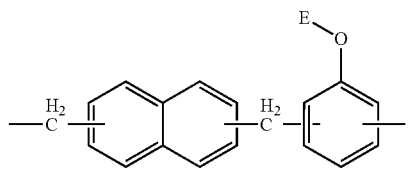

4D

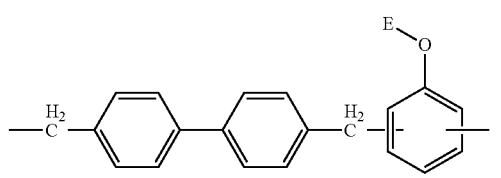

4E

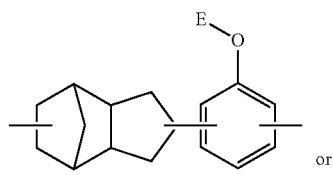

or

4F

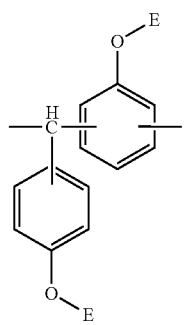

[Formula IC-2]

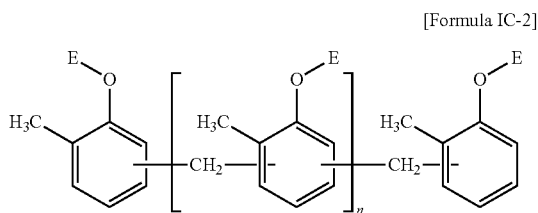

[Formula IC-3]

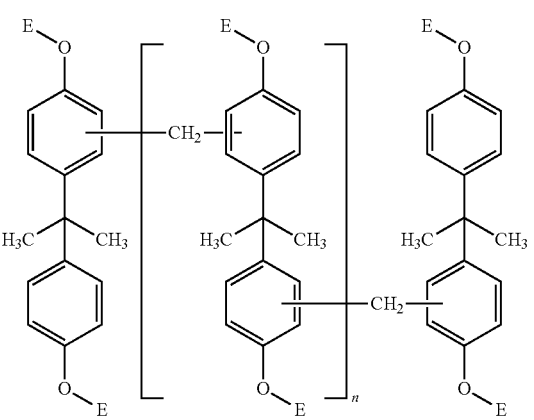

-continued

[Formula IC-4]
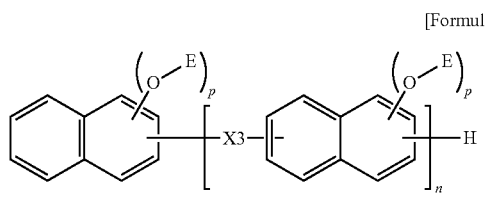

In the above Formula IC-4, x3 is

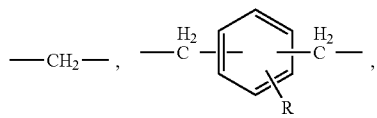

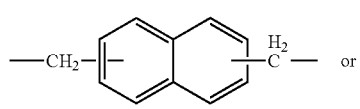

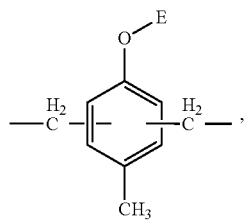

and in

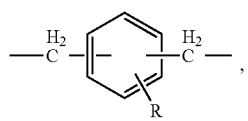

R is a linear or a branched alkyl group of C1-C10.

In the above Formula IC-1 to IC-4, at least two of a plurality of E are the following Formula B2, and the remainder are hydrogen. In the above Formula IC-1, in the case that Y2 is 4A to 4E, n is an integer of at least 2, and in the case that Y2 is 4F, n is an integer of at least 1. In the above Formulae IC-2 and IC-3, n is an integer of at least 1. In the above Formula IC-4, in the case that x3 is

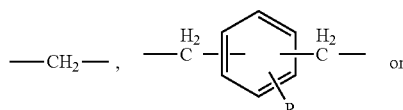

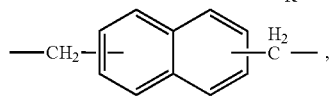

n is an integer of at least 2, and in the case that x3 is

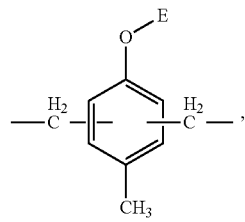

n is an integer of at least 1. In the above Formula IC-4, p is 1 or 2.

[Formula B2]
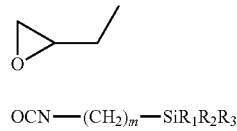

[Formula IIIB]

OCN—(CH$_2$)$_m$—SiR$_1$R$_2$R$_3$

In the above Formula IIIB, at least one of R$_1$ to R$_3$ is an alkoxy group having 1 to 5 carbon atoms, and the remainder thereof are an alkyl group of having 1 to 10 carbon atoms, the alkoxy group and the alkyl group may be a linear or a branched, and m is an integer from 3 to 10.

[Formula I-1]
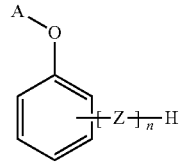

In the above Formula I-1, Z is one selected from the group consisting of the following Formulae 1A to 1F.

1A

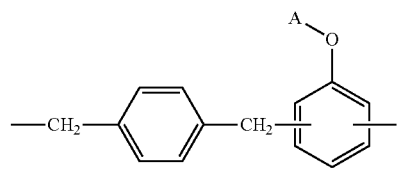

1B

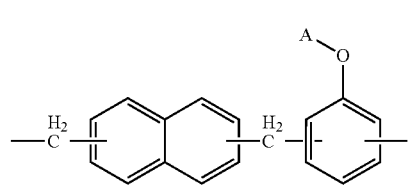

1C

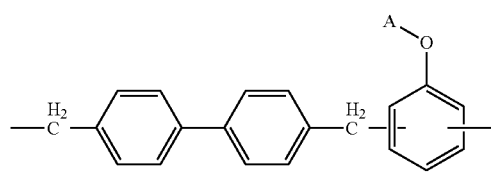
1D

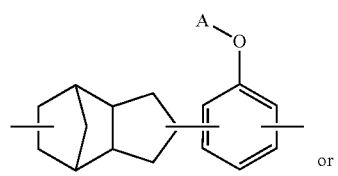
1E or

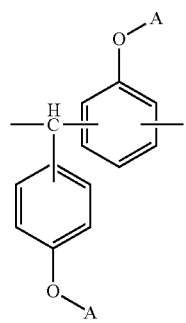
1F

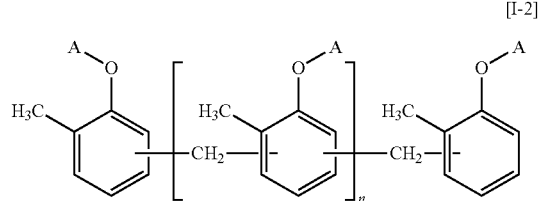
[I-2]

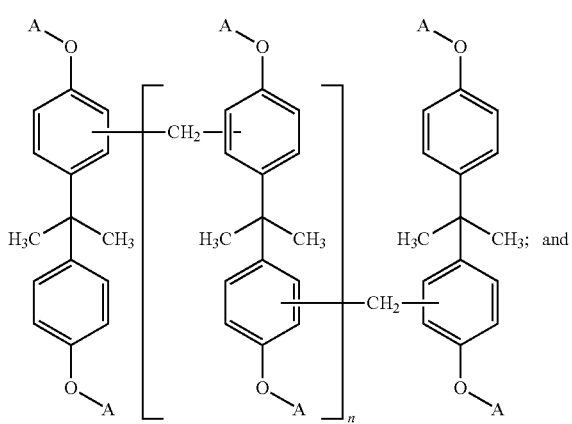
[I-3]

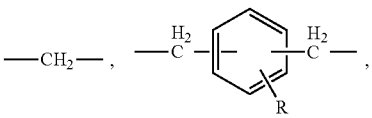
[I-4]

In the above Formula I-4, x is

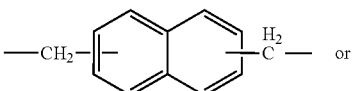

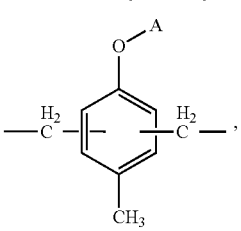

and in

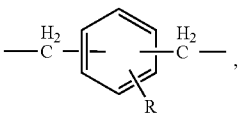

R is a linear or a branched alkyl group of C1-C10.

In the above Formulae I-1 to I-4, at least two of a plurality of A have the structure of the following Formula A2, and at least one of A has the following Formula A4 and the remainder thereof are hydrogen. In the above Formula I-1, in the case that Z is 1A to 1E, n is an integer of at least 2, and in the case that Z is 1F, n is an integer of at least 1. In the above Formulae I-2 and I-3, n is an integer of at least 1. In the above Formula I-4, in the case that x is

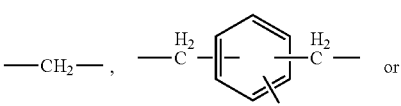

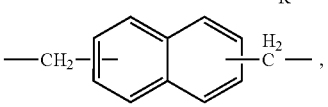

n is an integer of at least 2, and in the case that x is

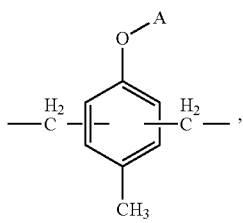

n is an integer of at least 1. In the above Formula I-4, p is 1 or 2.

[Formula A2]

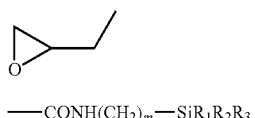

[Formula A4]

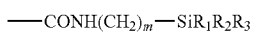

In the above Formulae A4, at least one of $R_1$ to $R_3$ is an alkoxy group having 1 to 5 carbon atoms, and the remainder thereof are an alkyl group having 1 to 10 carbon atoms, the alkoxy group and the alkyl group are a linear or a branched, and m is an integer from 3 to 10.

According to a ninth aspect of the present invention, a reaction in the first step may be performed using 1 to 10 equivalents of an epoxy group of the epichlorohydrin with respect to 1 equivalent of a hydroxyl group of one starting material of the above Formulae IA-1 to IA-4 in the production method of a novolac epoxy compound having at least one alkoxysilyl group according to the eighth aspect.

According to a tenth aspect of the present invention, a reaction in the first step may be performed at −20° C. to 100° C. for 1 to 120 hours in the production method of a novolac epoxy compound having at least one alkoxysilyl group according to the eighth aspect.

According to an eleventh aspect of the present invention, a reaction in the second step may be performed using 0.1 to 5 equivalents of the alkoxysilane with respect to 1 equivalent of a hydroxyl group of one intermediate of the above Formulae IC-1 to IC-4 in the production method of a novolac epoxy compound having at least one alkoxysilyl group according to the eighth aspect.

According to a twelfth aspect of the present invention, a reaction in the second step may be performed at −20° C. to 120° C. for 1 to 72 hours in the production method of a novolac epoxy compound having at least one alkoxysilyl group according to the eighth aspect.

According to a thirteenth aspect of the present invention, an epoxy composition including a novolac epoxy compound having at least one alkoxysil group selected from the group consisting of the following Formulae I-1 to I-4, is provided.

[Formula I-1]

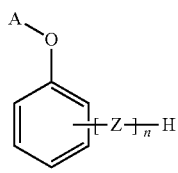

In the above Formula I-1, Z is one selected from the group consisting of the following Formulae 1A to 1F.

1A

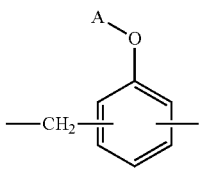

1B

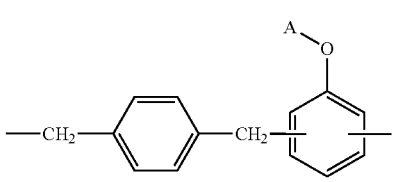

1C

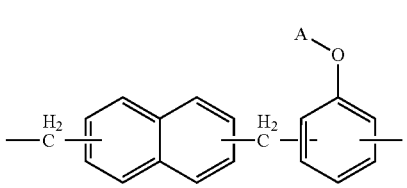

1D

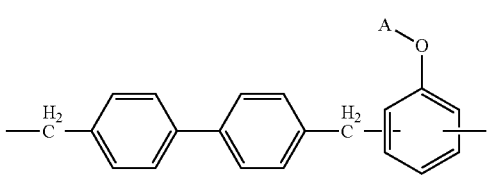

1E

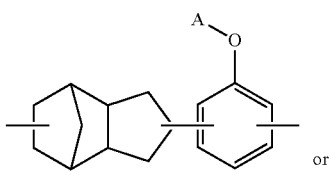

or

1F

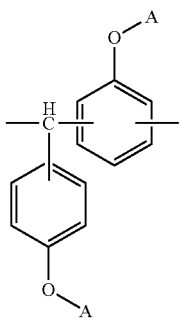

[I-2]

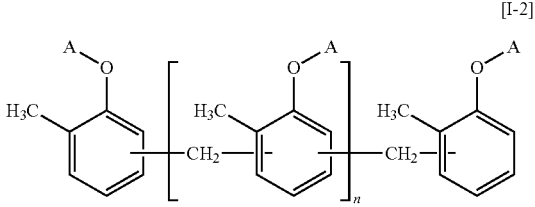

-continued

[I-3]

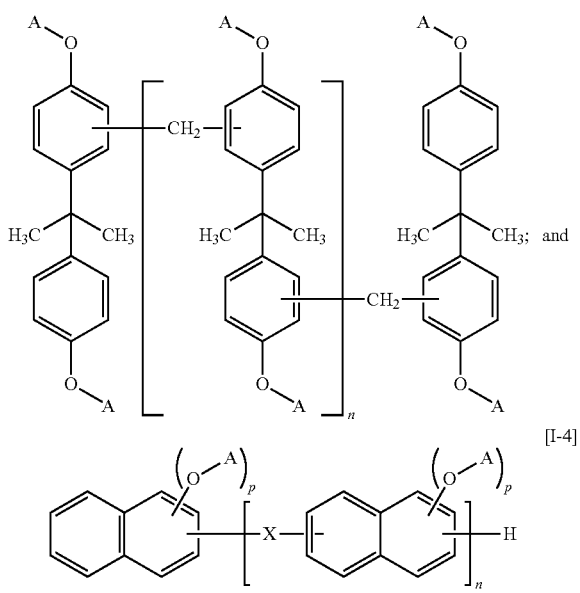

[I-4]

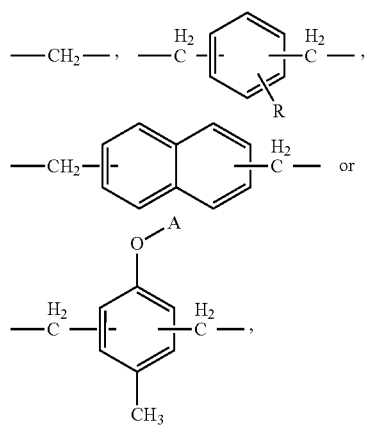

In the above Formula I-4, x is

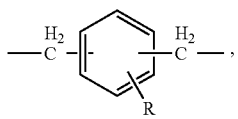

and in

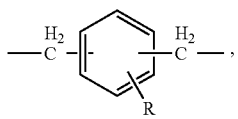

R is a linear or a branched alkyl group of C1-C10.

In the above Formulae I-1 to I-4, at least two of a plurality of A have the structure of the following Formula A2, and at least one of A has the structure of the following Formula A3 or A4, where in the case that at least one of A is A3, the remainder thereof have the following Formula B3 or hydrogen, and in the case that at least one thereof is A4, the remainder thereof are hydrogen. In the above Formula I-1, in the case that Z is 1A to 1E, n is an integer of at least 2, and in the case that Z is 1F, n is an integer of at least 1. In the above Formulae I-2 and I-3, n is an integer of at least 1.

In the above Formula I-4, in the case that x is

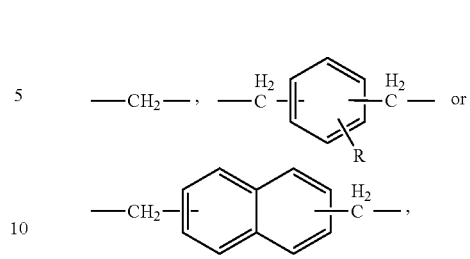

n is an integer of at least 2, and in the case that x is

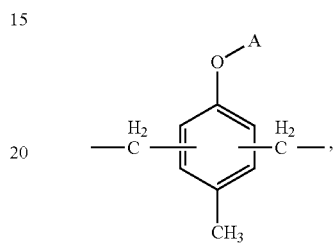

n is an integer of at least 1. In the above Formula I-4, p is 1 or 2.

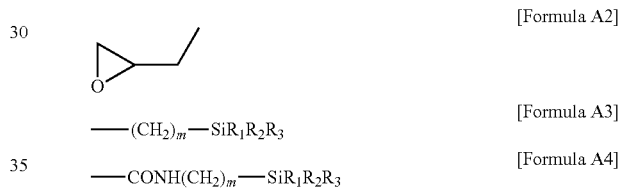

[Formula A2]

[Formula A3] —(CH$_2$)$_m$—SiR$_1$R$_2$R$_3$

[Formula A4] —CONH(CH$_2$)$_m$—SiR$_1$R$_2$R$_3$

In the above Formulae A3 and A4, at least one of $R_1$ to $R_3$ is an alkoxy group having 1 to 5 carbon atoms, and the remainder thereof are an alkyl group having 1 to 10 carbon atoms, the alkoxy group and the alkyl group are a linear or a branched, and m is an integer from 3 to 10.

—(CH$_2$)$_l$—CH=CH$_2$  [Formula B3]

In the above Formula B3, l is an integer from 1 to 8.

According to a fourteenth aspect of the present invention, at least one epoxy compound selected from the group consisting of a glycidyl ether-based epoxy compound, a glycidyl-based epoxy compound, a glycidyl amine-based epoxy compound, a glycidyl ester-based epoxy compound, a rubber modified epoxy compound, an aliphatic polyglycidyl-based epoxy compound and an aliphatic glycidyl amine-based epoxy compound may be further included in the epoxy composition according to the thirteenth aspect.

According to a fifteenth aspect of the present invention, the epoxy compound may include bisphenol A, bisphenol F, bisphenol S, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol, a cyclo aliphatic compound, or a novolac unit, as a core structure in the epoxy composition according to the fourteenth aspect.

According to a sixteenth aspect of the present invention, the epoxy compound may include the bisphenol A, the biphenyl, the naphthalene, or the fluorene as the core structure in the epoxy composition according to the fifteenth aspect.

According to a seventeenth aspect of the present invention, the epoxy composition may include 10 wt % to 100 wt % of the epoxy compound having an alkoxysilyl group and 0 wt % to 90 wt % of at least one epoxy compound selected from the group consisting of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound based on the total content of the epoxy compound in the epoxy composition according to the fourteenth aspect.

According to an eighteenth aspect of the present invention, the epoxy composition may include 30 wt % to 100 wt % of the epoxy compound having an alkoxysilyl group and 0 wt % to 70 wt % of at least one epoxy compound selected from the group consisting of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound based on the total content of the epoxy compound in the epoxy composition according to the seventeenth aspect.

According to a nineteenth aspect of the present invention, at least one filler selected from the group consisting of inorganic particles or a fiber may be further included in the epoxy composition according to any one of the thirteenth to eighteenth aspects.

According to a twentieth aspect of the present invention, the inorganic particle may be at least one selected from the group consisting of a metal oxide selected from the group consisting of silica, zirconia, titania, alumina, silicon nitride and aluminum nitride, T-10 type silsesquioxane, ladder type silsesquioxane and cage type silsesquioxane in the epoxy composition according to the nineteenth aspect.

According to a twenty-first aspect of the present invention, an content of the inorganic particles may be 5 wt % to 95 wt % based on a total solid content of the epoxy composition in the epoxy composition according to the nineteenth aspect.

According to a twenty-second aspect of the present invention, an content of the inorganic particles may be 30 wt % to 95 wt % based on a total solid content of the epoxy composition in the epoxy composition according to the twenty-first aspect.

According to a twenty-third aspect of the present invention, an content of the inorganic particles may be 5 wt % to 60 wt % based on a total solid content of the epoxy composition in the epoxy composition according to the twenty-first aspect.

According to a twenty-fourth aspect of the present invention, the fiber may be at least one glass fiber selected from the group consisting of an E-glass fiber, a T-glass fiber, an S-glass fiber, an NE-glass fiber, an E-glass fiber, an H-glass fiber, quartz, and at least one organic fiber selected from the group consisting of a liquid crystal polyester fiber, a polyethyleneterephthalate fiber, a wholly aromatic fiber, a polyoxybenzasol fiber, a nylon fiber, a polyethylene naphthalate fiber, a polypropylene fiber, a polyether sulfone fiber, a polyvinylidene fluoride fiber, a polyethylene sulfide fiber and a polyether ether ketone fiber in the epoxy composition according to the nineteenth aspect.

According to a twenty-fifth aspect of the present invention, the fiber may be an E-glass fiber in the epoxy composition according to the twenty-fourth aspect.

According to a twenty-sixth aspect of the present invention, the fiber may be a T-glass fiber in the epoxy composition according to the twenty-fourth aspect.

According to a twenty-seventh aspect of the present invention, an content of the fiber may be 10 wt % to 90 wt % based on a total solid content of the epoxy composition in the epoxy composition according to the nineteenth aspect.

According to a twenty-eighth aspect of the present invention, inorganic particles may be further included in the case that a fiber is included in the epoxy composition according to the nineteenth aspect.

According to a twenty-ninth aspect of the present invention, a curing agent may be further included in the epoxy composition according to any one of the thirteenth to twenty-eighth aspects.

According to a thirtieth aspect of the present invention, an reaction catalyst for alkoxysilyl group may be further included in the epoxy composition according to any one of the thirteenth to twenty-ninth aspects.

According to a thirty-first aspect of the present invention, the reaction catalyst for alkoxysilyl group may be at least one selected from the group consisting of at least one inorganic acid selected from the group consisting of nitric acid, sulfuric acid, hydrochloric acid, acetic acid and phosphoric acid, ammonia, KOH, NH$_4$OH, amine, a transition metal alkoxide, and a tin compound in the epoxy composition according to the thirtieth aspect.

According to a thirty-second aspect of the present invention, the reaction catalyst may be used by 0.01 phr to 10 phr based on the epoxy compound having an alkoxysilyl group in the epoxy composition according to the thirtieth aspect.

According to a thirty-third aspect of the present invention, water may be further included in the epoxy composition according to the thirtieth aspect.

According to a thirty-fourth aspect of the present invention, an electronic material including the epoxy composition according to any one of the thirteenth to thirty-third aspects, is provided.

According to a thirty-fifth aspect of the present invention, a substrate including the epoxy composition according to any one of the thirteenth to thirty-third aspects, is provided.

According to a thirty-sixth aspect of the present invention, a film including the epoxy composition according to any one of the thirteenth to thirty-third aspects, is provided.

According to a thirty-seventh aspect of the present invention, a laminate including a metal layer placed on a base layer formed by using the epoxy composition according to any one of the thirteenth to thirty-third aspects, is provided.

According to a thirty-eighth aspect of the present invention, a printed circuit board including the laminate according to the thirty-seventh aspect, is provided.

According to a thirty-ninth aspect of the present invention, a semiconductor device including the printed circuit board according to the thirty-eighth aspect, is provided.

According to a fortieth aspect of the present invention, a semiconductor packaging material including the epoxy composition according to any one of the thirteenth to thirty-third aspects, is provided.

According to a forty-first aspect of the present invention, a semiconductor device including the semiconductor packaging material according to the fortieth aspect, is provided.

According to a forty-second aspect of the present invention, an adhesive including the epoxy composition according to any one of the thirteenth to thirty-third aspects, is provided.

According to a forty-third aspect of the present invention, a paint including the epoxy composition according to any one of the thirteenth to thirty-third aspects, is provided.

According to a forty-fourth aspect of the present invention, a composite material including the epoxy composition according to any one of the thirteenth to thirty-third aspects, is provided.

According to a forty-fifth aspect of the present invention, a prepreg including the epoxy composition according to any one of the thirteenth to thirty-third aspects, is provided.

According to a forty-sixth aspect of the present invention, a laminate including a metal layer placed on the prepreg of the forty-fifth aspect, is provided.

According to a forty-seventh aspect of the present invention, a cured article of the epoxy composition according to any one of the thirteenth to thirty-third aspects, is provided.

According to a forty-eighth aspect of the present invention, the cured article may have a CTE of less than or equal to 60 ppm/° C. according to the forty-seventh aspect.

According to a forty-ninth aspect of the present invention, the cured article may have a glass transition temperature of 100° C. or above, or may not exhibit the glass transition temperature according to the forty-seventh aspect.

Advantageous Effects

According to exemplary embodiments of the present invention, due to chemical bonding formed by a chemical reaction between an alkoxysilyl group and a filler (fiber and/or inorganic particles) and between the alkoxysilyl groups in the composite and/or cured article of an epoxy composition including a novel novolac epoxy compound having at least one alkoxysilyl group, heat resistance property may be improved. That is, the CTE of an epoxy composite may be decreased, and a glass transition temperature may be increased or the glass transition temperature may not be observed (Tg-less). In addition, the cured article of the novolac epoxy compound having at least one alkoxysilyl group may exhibit good flame retardancy due to the introduction of the alkoxysilyl group.

Further, when the composition of novolac epoxy according to the present invention is applied on a metal film, good adhesive property may be exhibited with respect to the metal film due to the chemical bonding between the functional group at the surface of the metal film and the alkoxysilyl group. In addition, due to the increase in chemical bonding efficiency of the composition including the novolac epoxy compound, a silane coupling agent used in a common epoxy composition may be unnecessary in the composition including the novolac epoxy compound. The epoxy composition including the novolac epoxy compound may have good curing efficiency, and a composite obtained by curing thereof may exhibit good thermal expansion property such as a low CTE and a high glass transition temperature or Tg-less.

DESCRIPTION OF DRAWINGS

The above and other aspects, features and other advantages of the present invention will be more clearly understood from the following detailed description taken in conjunction with the accompanying drawings, in which.

BEST MODE

Figure 1:
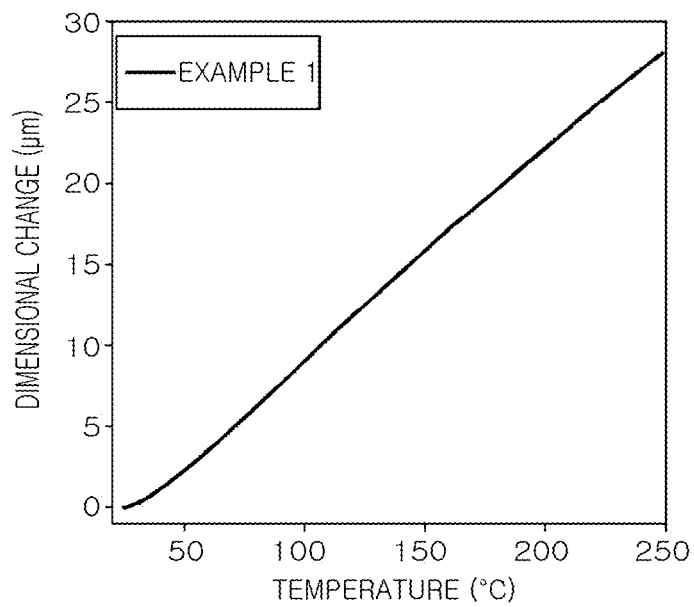
FIG. 1 is a graph illustrating dimensional change with the variation of the temperature of a composite according to Example 1.

The present invention provides a novel novolac epoxy compound containing an alkoxysilyl group, a production method of the same, an epoxy composition and a cured article including the same, and a cured article of the composition, in which a composite obtained by curing the epoxy composition exhibits improved heat resistance property, a particularly low CTE and a high Tg (including Tg-less), and/or a cured article of the epoxy composition exhibits good flame retardancy.

In the present invention, "composite" refers to a cured article formed by using a composition including an epoxy compound and a filler (fiber and/or inorganic particles). In the present invention, "cured article", as a general sense, refers to a cured article formed from a composition including an epoxy compound, for example, a cured article formed of a composition including an epoxy compound, a curing agent, and at least one selected from the group consisting of a filler, an additional curing agent, an optional curing accelerator and other additives. In addition, the term "cured article" is also used to denote a "partially-cured article". Generally, only a cured article reinforced with inorganic particles and/or a fiber is called as a composite, and the cured article has a wider meaning than the composite. However, the term "cured article" reinforced with inorganic particles and/or fibers may be considered to have the same meaning as the term "composite."

When forming a composite through curing the novolac epoxy compound in accordance with the present invention, an epoxy group may react with a curing agent to conduct a crosslinking reaction, and the alkoxysilyl group may form an interfacial bonding with the surface group of the filler (fiber and/or inorganic particles), and/or chemical bonding may be formed between alkoxysilyl groups. Thus, the remarkably high chemical bonding efficiency may be obtained in an epoxy composite system, and as a result a low CTE and high increasing effect of glass transition temperature or Tg-less may be achieved. Therefore, dimensional stability may be improved. In addition, separate silane coupling agents are not necessary. Further, the cured article including the novolac epoxy compound of the present invention may exhibit good flame retardancy.

In addition, when applying the epoxy composition of the present invention to a chemically treated metal film such as a copper film, a chemical bonding may be formed with a hydroxyl group or the like on the surface of the metal produced through the metal surface treatment, thereby exhibiting good adhesion with respect to the metal film.

1. Epoxy Compound

According to an embodiment of the present invention, a novolac epoxy compound having at least one alkoxysilyl group selected from the group consisting of the following Formulae I-1 to I-4 is provided.

[Formula I-1]

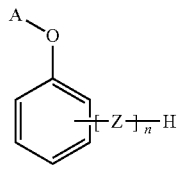

In the above Formula I-1, Z is one selected from the group consisting of the following Formulae 1A to 1F.

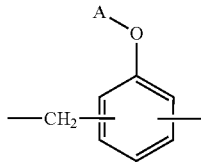

1A

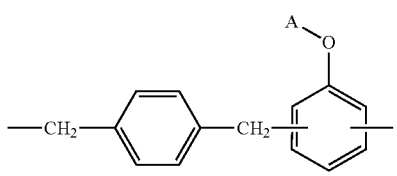

1B

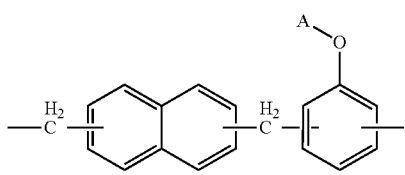

1C

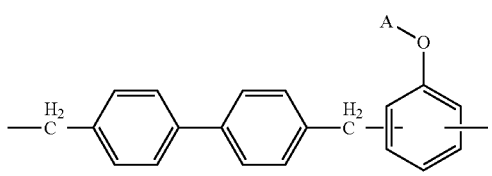

1D

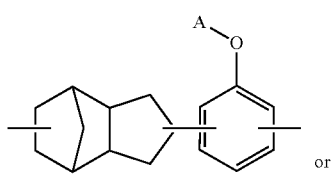

1E

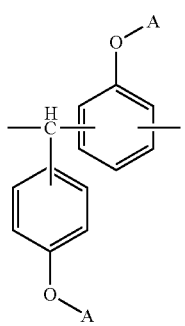

or

1F

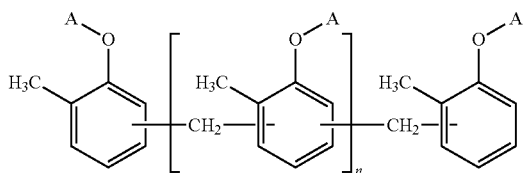

[I-2]

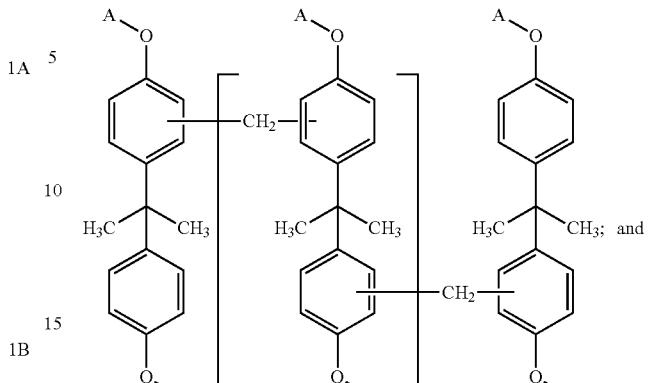

[I-3]

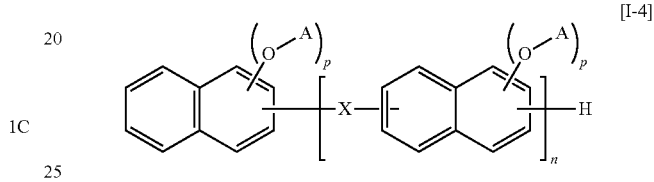

[I-4]

In the above Formula I-4, x is

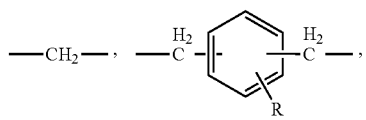

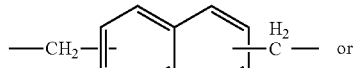

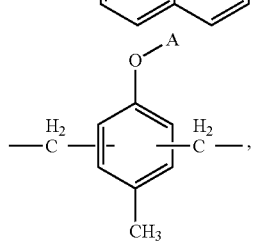

and in

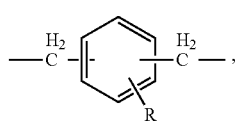

R is a linear or a branched alkyl group of C1-C10.

In the above Formulae I-1 to I-4, at least two of a plurality of A have the structure of the following Formula A2, and at least one of A has the structure of the following Formula A3 or A4, where in the case that at least one of A is A3, the remainder thereof have the following Formula B3 or hydrogen, and in the case that at least one of A is A4, the remainder thereof are hydrogen. In the above Formula I-1, in the case that Z is 1A to 1E, n is an integer of at least 2, and in the case that Z is 1F, n is an integer of at least 1. In the above Formulae I-2 and I-3, n is an integer of at least 1. In the above Formula I-4, in the case that x is

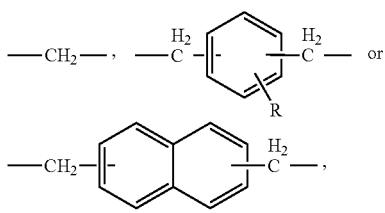

n is an integer of at least 2, and in the case that x is

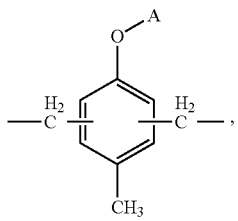

n is an integer of at least 1.

Here, n is an integer of at least 1, for example an integer from 1 to 1,000, and for example, an integer from 2 to 1,000 and includes all integers in the range. Particularly, in the case that Z is 1A to 1E in Formula I-1, and in the case that z is

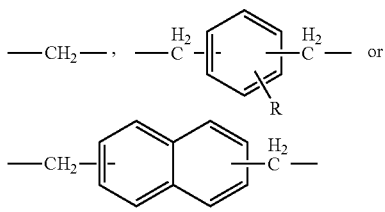

in Formula I-4, n is an integer from 2 to 1,000. In the above Formula I-4, p is 1 or 2.

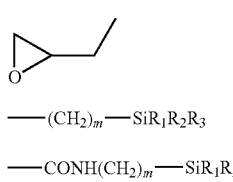
[Formula A2]

—(CH$_2$)$_m$—SiR$_1$R$_2$R$_3$     [Formula A3]

—CONH(CH$_2$)$_m$—SiR$_1$R$_2$R$_3$     [Formula A4]

In the above Formulae A3 and A4, at least one of R$_1$ to R$_3$ is an alkoxy group having 1 to 5 carbon atoms, and preferably, an ethoxy group, and the remainder thereof are an alkyl group having 1 to 10 carbon atoms, and m is an integer from 3 to 10, and preferably, an integer from 3 to 6. The alkoxy group and the alkyl group may be a linear or a branched.

—(CH$_2$)$_l$—CH=CH$_2$     [Formula B3]

In the above Formula B3, l is an integer from 1 to 8.

In the novolac epoxy compound having at least one alkoxysilyl group according to an embodiment of the present invention, and in the above Formulae A3 and A4, at least one of R$_1$ to R$_3$ may preferably be an ethoxy group in consideration of reaction stability and/or reactivity with a filler during curing reaction.

In the present application, "alkoxy group" denotes a monovalent group of —OR (R is an alkyl group) and may be a linear or branched.

In the present application, "alkyl group" denotes a monovalent hydrocarbon group and may be a linear or a branched.

Further, a composite obtained by curing of a composition including the novolac epoxy compound having at least one alkoxysilyl group according to an embodiment of the present invention exhibits a low CTE, high glass transition temperature increasing effect or Tg-less property.

2. Production Method of Epoxy Compound

The novolac epoxy compound of the above Formulae I-1 to I-4 according to an embodiment of the present invention may be synthesized by the following methods.

(1) Production Method of Novolac Epoxy Compound of Formulae I-1 to I-4 Having Formula A3 (Method 1)

According to another embodiment of the present invention, a production method of an epoxy compound having Formulae I-1 to I-4 containing a substituent of Formula A3 is provided. The epoxy compound of Formula I containing the substituent of Formula A3 may be prepared via alkenylation, epoxidation of a starting material (first step) and alkoxysilylation (second step).

In the first step, through the reaction of a starting material of the following Formulae IA-1 to IA-4 (hereinafter, 'starting material' or 'starting material IA'), an alkenyl compound of the following Formula II and epichlorohydrin, hydroxyl group may be partially alkenylated and partially epoxidized to form an intermediate of Formulae IB-1 to IB-4 (hereinafter, 'intermediate IB').

[Formula IA-1]

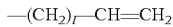

In the above Formula IA-1, X is one selected from the group consisting of the following Formulae 2A to 2F.

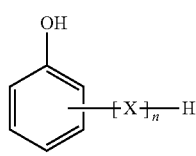
2A

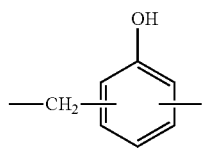
2B

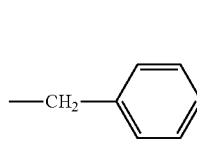
2C

-continued

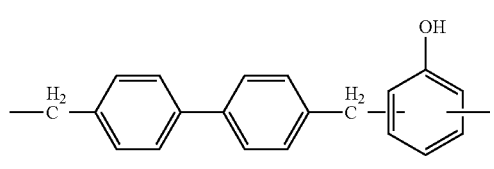
2D

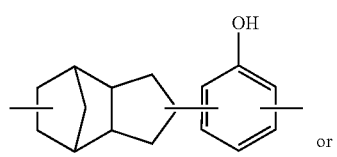
2E

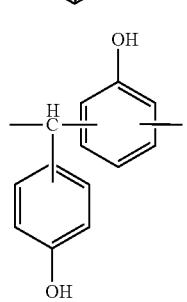
or

[Formula IA-2]

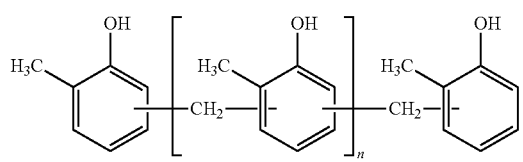

[Formula IA-3]

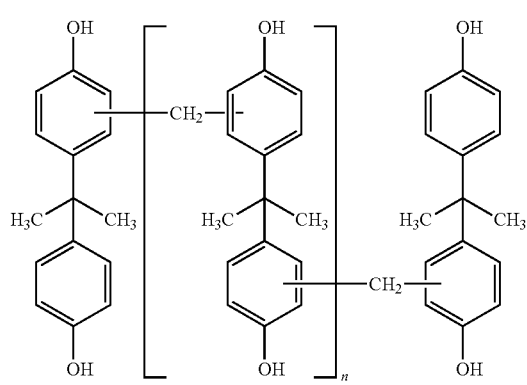

[Formula IA-4]

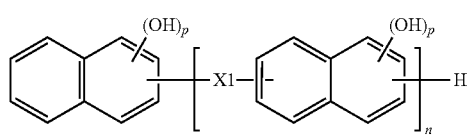

In the above Formula IA-4, x1 is

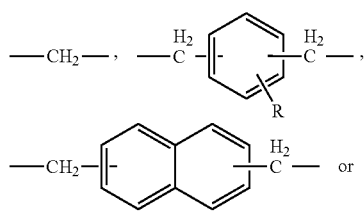
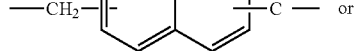
or

-continued

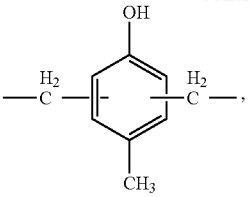
2F and in

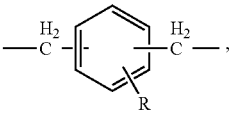

R is a linear or a branched alkyl group of C1-C10.

In the above Formula IA-1, in the case that X is 2A to 2E, n is an integer of at least 2, and in the case that X is 2F, n is an integer of at least 1. In the above Formulae IA-2 and IA-3, n is an integer of at least 1. In the above Formula IA-4, in the case that x1 is

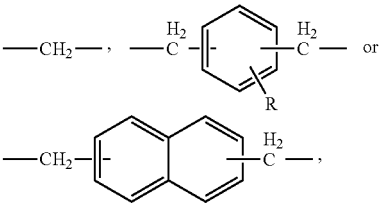

n is an integer of at least 2, and in the case that x1 is

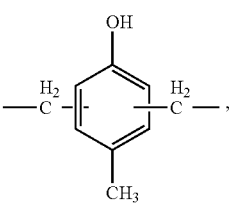

n is an integer of at least 1.

Particularly, in the above Formulae IA-1 to IA-4, n is an integer of at least 1, for example, an integer from 1 to 1,000, and for example, an integer from 2 to 1,000 and includes all integers in the range. Particularly, in the case that X is 2A to 2E in Formula IA-1, and in the case that x1 is

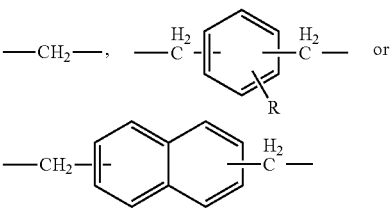

in Formula IA-4, n is an integer from 2 to 1,000. In the above Formula IA-4, p is 1 or 2.

[Formula IB-1]
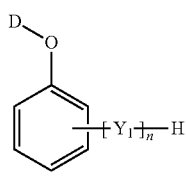
In the above Formula IB-1, $Y_1$ is one selected from the group consisting of the following Formulae 3A to 3F.
3A
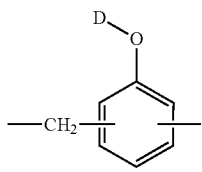
3B
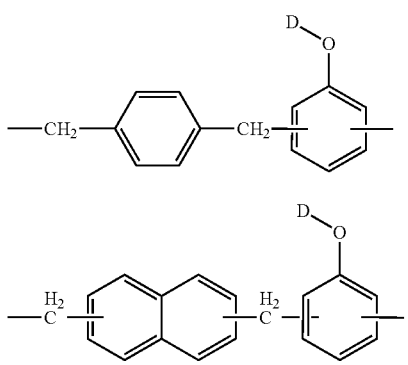
3C
3D
3E
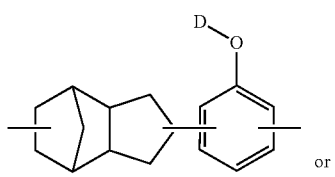
or
3F
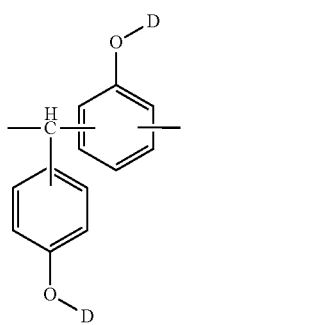
[Formula IB-2]
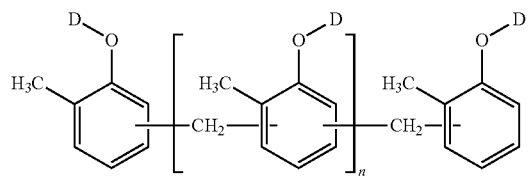
[Formula IB-3]
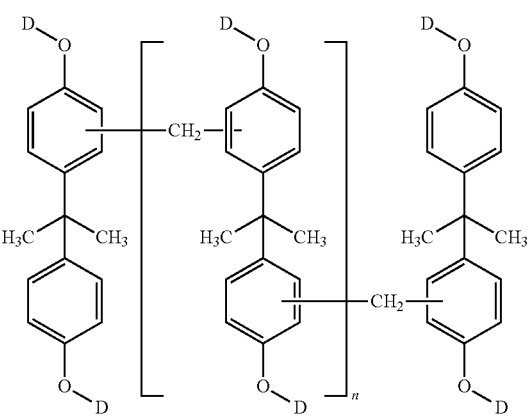
[Formula IB-4]
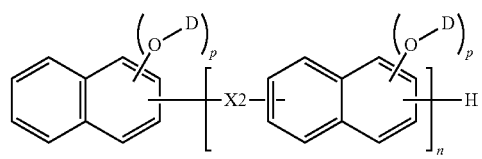
In the above Formula IB-4, x2 is
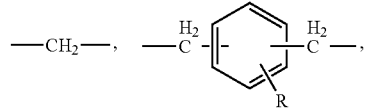
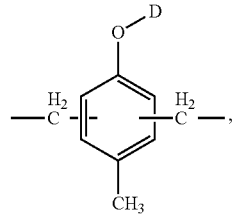
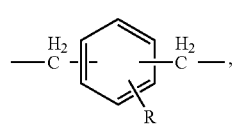
R is a linear or a branched alkyl group of C1-C10.
In the above Formulae IB-1 to IB-4, at least two of a plurality of D may be the following Formula B2, at least one of D may be the following Formula B3, and the remainder thereof may be hydrogen. In the above Formulae IB-1, in the case that Y1 is 3A to 3E, n is an integer of at least 2, and in the case that Y1 is 3F, n is an integer of at least 1. In the above Formulae IB-2 and IB-3, n is an integer of at least 1. In the above Formula IB-4, in the case that x2 is

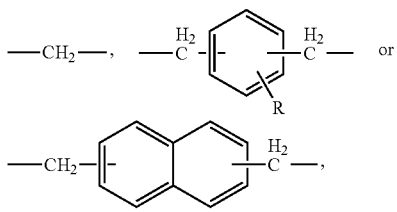

n is an integer of at least 2, and in the case that x2 is

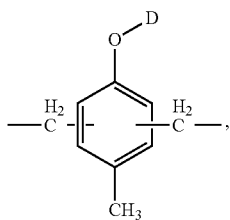

n is an integer of at least 1.

n is an integer of at least 1, for example, an integer from 1 to 1,000, and for example, an integer from 2 to 1,000 and refers to all integers in the range. Particularly, in the case that Y1 is 3A to 3E in Formula IB-1, and in the case that x2 is

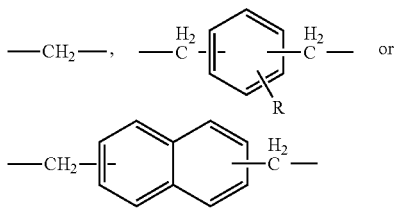

in Formula IB-4, n is an integer from 2 to 1,000. In the above Formula IB-4, p is 1 or 2.

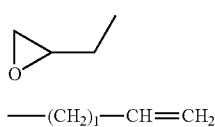 [Formula B2]

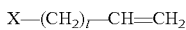 [Formula B3]

In the above Formula B3, l is an integer from 1 to 8, and preferably, an integer from 1 to 4.

X—(CH$_2$)$_l$—CH═CH$_2$  [Formula II]

In the above Formula II, l is an integer from 1 to 8, and preferably, an integer from 1 to 4, and X is a halide such as Cl, Br or I, —O—SO$_2$—CH$_3$, —O—SO$_2$—CF$_3$, or —O—SO$_2$—C$_6$H$_4$—CH$_3$.

The alkenylation and the epoxidation in the first step are performed by reacting the starting material of the above Formulae IA-1 to IA-4, the alkenyl compound of the above Formula II and the epichlorohydrin in the presence of a base and an optional solvent. In this case, the reaction may be performed by adding the alkenyl compound and the epichlorohydrin to the starting material at the same time, or by adding the alkenyl compound and the epichlorohydrin in the starting material one by one in-situ. In consideration of the control of reactivity, the alkenyl compound and the epichlorohydrin may preferably be added one by one for the reaction.

Further, in the first step reaction, the reaction of the starting material, the alkenyl compound and the epichlorohydrin is performed so that 0.1 to 10 equivalents of an alkenyl group with respect to 1 equivalent of the hydroxyl group of the starting material and 1 to 10 equivalents of an epoxy group (glycidyl group) of the epichlorohydrin with respect to 1 equivalent of the hydroxyl group of the starting material may react, in the presence of the base and the optional solvent, to produce intermediate IB. The reactants react according to equivalent ratios on the basis of stoichiometry, and through the reaction of the reactants by the equivalent ratio, target intermediate IB is obtained.

The reaction temperature and the reaction time of the first step may change depending on the kind of reactants, and the reaction may be performed, for example, at from −20° C. to 100° C. for 1 to 120 hours to produce intermediate IB.

The base used may include, for example, KOH, NaOH, K$_2$CO$_3$, Na$_2$CO$_3$, KHCO$_3$, NaHCO$_3$, NaH, triethylamine and diisopropylethylamine, without limitation. These bases may be used alone or as a combination of two or more thereof. 0.1 to 5 equivalents of the base may be used with respect to 1 equivalent of the hydroxyl group of the starting material IA in consideration of reaction efficiency.

The solvents used during the reaction of the first step may be any solvents as occasion demands. For example, the solvent may not be used if the viscosity of the reactants at the reaction temperature is appropriate for carrying out the reaction without using a separate solvent in the first step reaction. That is, a separate solvent is not necessary in the case in which the viscosity of the reactants is sufficiently low, and the mixing and stirring of the reactants may be easily performed without solvents. This may be easily decided upon by a person skilled in the art. In the case in which a solvent is used, any organic solvent may be used, if able to dissolve the reactants properly, not inducing any adverse influence to the reaction, and being easily removed after the reaction. For example, acetonitrile, tetrahydrofuran (THF), methyl ethyl ketone (MEK), dimethylformamide (DMF), dimethyl sulfoxide (DMSO), methylene chloride (MC), H$_2$O, alcohols, toluene, or the like, may be used, without specific limitation. These solvents may be used alone or as a mixture of two or more thereof. The content of the solvent may not be limited to being within a specific range, and an appropriate content of the solvent may be used within a range needed for dissolving the reactants sufficiently and not adversely affecting the reaction. A person skilled in the art may select an appropriate content of the solvent in consideration of the above-mentioned points.

After that, in the second step, the above intermediate IB is alkoxysilylated in the presence of a platinum catalyst and an optional solvent to produce a novolac epoxy compound of Formulae I-1 to I-4 having substituent A3 according to an embodiment of the present invention.

In the second step reaction, the reaction of intermediate IB and alkoxysilane is performed according to the equivalent ratio of the alkenyl group of intermediate IB and the alkoxysilane. Thus, the reaction of intermediate IB and the alkoxysilane of the following Formula IIIA is performed so that 0.1 to 5 equivalents of the alkoxysilane of the following Formula IIIA with respect to 1 equivalent of an alkenyl group of the above intermediate IB may react in consideration of the equivalent ratio.

 [Formula IIIA]

In the above Formula IIIA, at least one of $R_a$ to $R_c$ is an alkoxy group of C1-C5, and preferably, an ethoxy group, and the remainder thereof are an alkyl group of C1-C10, and the alkoxy group and the alkyl group may be a linear or a branched.

The reaction temperature and the reaction time of the second step may change depending on the kind of reactants, and the reaction may be performed, for example, within a temperature range from −20° C. to 120° C. for 1 to 72 hours to produce a novolac epoxy compound of Formulae I-1 to I-4 having substituent A3.

In the second step, the platinum catalyst may be, for example, $PtO_2$ or chloroplatinic acid ($H_2PtCl_6$), without limitation. $1\times10^{-4}$ to 0.05 equivalents of the platinum catalyst with respect to 1 equivalent of the alkenyl group of intermediate IB may preferably be used in consideration of reaction efficiency.

The solvents used during the second step reaction may be any optional solvent. For example, the solvent may not be used if the viscosity of the reactants at the reaction temperature is appropriate for carrying out the second step reaction without using a separate solvent. That is, a separate solvent is not necessary in the case in which the viscosity of the reactants is sufficiently low, and the mixing and stirring of the reactants may be easily performed without solvents. This may be easily decided upon by a person skilled in the art. In the case in which a solvent is used, any aprotic solvent may be used, if able to dissolve the reactants properly, not inducing any adverse influence to the reaction, and being easily removed after the reaction. For example, toluene, acetonitrile, THF (tetra hydro furan), MEK (methyl ethyl ketone), DMF (dimethyl formamide), DMSO (dimethyl sulfoxide), methylene chloride (MC) or the like, may be used, without limitation. These solvents may be used alone or as a mixture of two or more thereof. The content of the solvent may not be limited to being within a specific range, and an appropriate content of the solvent may be used within a range for dissolving the reactants sufficiently and not adversely affecting the reaction. A person skilled in the art may select an appropriate content of the solvent in consideration of the above-mentioned points.

An exemplary reaction scheme of the above production method (1) of Formula I-1 when Z is IA is as follows.

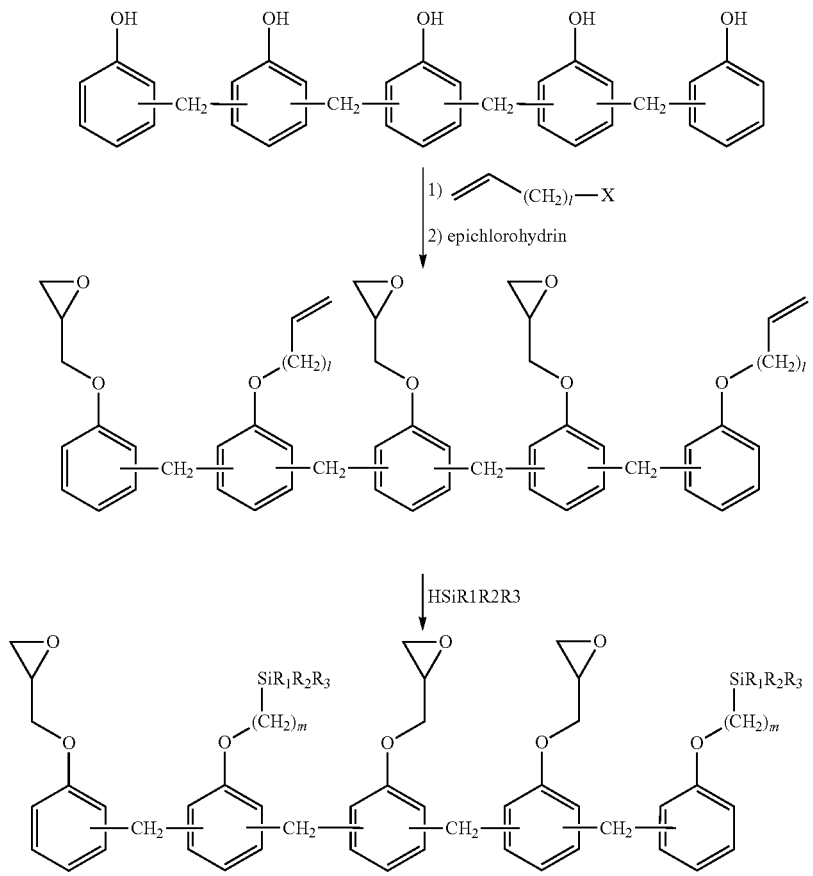

As defined in the epoxy compounds of the above Formulae I-1 to I-4, at least two of a plurality of substituent A of Formulae I-1 to I-4 may have the structure of Formula A2 (that is, an epoxy group), at least one thereof may have the structure of Formula A3 (that is, an alkoxysilyl group), and the remainder may be hydrogen.

The extent of substitution of the epoxy group and the alkoxysilyl group with respect to Formulae I-1 to I-4 may be changed by controlling the number of hydroxyl groups alkenylated and epoxidated by controlling the equivalents of the alkenyl compound and the epichlorohydrin and the reaction temperature in the first reaction of the first step. A person skilled in the art may appropriately select the substitution state in consideration of the reactivity from the above-mentioned points.

(2) Production Method of Novolac Epoxy Compound of Formulae I-1 to I-4 Having Substitutent of Formula A4 (Method 2)

According to another embodiment of the present invention, a production method of an epoxy compound of Formulae I-1 to I-4 having a substitutent of Formula A4 is provided. The novolac epoxy compound of Formulae I-1 to I-4 having the substitutent of Formula A4 may be prepared by the method of epoxidation (first step) of a starting material and alkoxysilylation (second step).

In the first step, through the reaction of a starting material of the above starting materials, Formulae IA-1 to IA-4 (hereinafter, 'starting material' or 'starting material IA') and epichlorohydrin in the presence of a base and an optional solvent, the hydroxyl group of the starting material may be epoxidized to form an intermediate of Formula IC. In this case, the reaction of the starting material and the epichlorohydrin is performed so that 1 to 10 equivalents of the epoxy group (glycidyl group) of the epichlorohydrin with respect to 1 equivalent of the hydroxyl group of the starting material may react, in the presence of the base and the optional solvent, to produce an intermediate of Formulae IC-1 to IC-4 (hereinafter 'intermediate IC').

The reaction temperature and the reaction time of the first step may change depending on the kind of reacting material, and the reaction may be performed, for example, at from −20° C. to 100° C. for 1 to 120 hours to produce intermediate IC.

The base used may include, for example, KOH, NaOH, $K_2CO_3$, $Na_2CO_3$, $KHCO_3$, $NaHCO_3$, NaH, triethylamine, and diisopropylethylamine, without limitation. These bases may be used alone or as a combination of two or more thereof. 0.1 to 5 equivalents of the base may be used with respect to 1 equivalent of the hydroxyl group of the starting material IA in consideration of reaction efficiency.

The solvent used during the reaction of the first step may be any solvent, as occasion demands. For example, the solvent may not be used if the viscosity of the reactants at the reaction temperature is appropriate for carrying out the reaction without using a separate solvent in the first step reaction. That is, a separate solvent is not necessary in the case in which the viscosity of the reactants is sufficiently low, and the mixing and stirring of the reactants may be easily performed without solvents. This may be easily decided upon by a person skilled in the art. In the case in which a solvent is used, any organic solvent may be used, if able to dissolve the reactants properly, not inducing any adverse influence to the reaction, and being easily removed after the reaction. For example, acetonitrile, THF (tetra hydro furan), MEK (methyl ethyl ketone), DMF (dimethyl formamide), DMSO (dimethyl sulfoxide), methylene chloride (MC), $H_2O$, alcohols, or the like may be used, without limitation. These solvents may be used alone or as a mixture of two or more thereof. The content of the solvent may not be limited to being within a specific range, and an appropriate content of the solvent may be used within a range sufficient for sufficiently dissolving the reactants and not adversely affecting the reaction. A person skilled in the art may select an appropriate content of the solvent in consideration of the above-mentioned points.

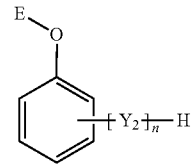

[Formula IC-1]

In the above Formula IC-1, $Y_2$ is one selected from the group consisting of the following Formulae 4A to 4F.

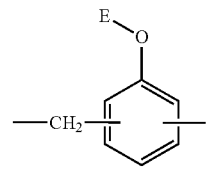

4A

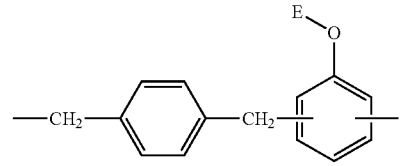

4B

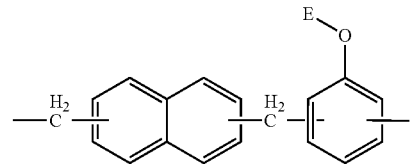

4C

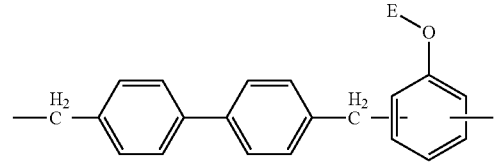

4D

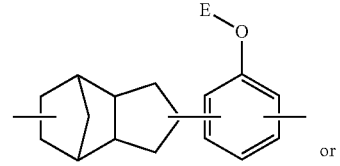

4E or

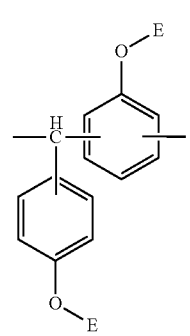

4F

-continued

[Formula IC-2]

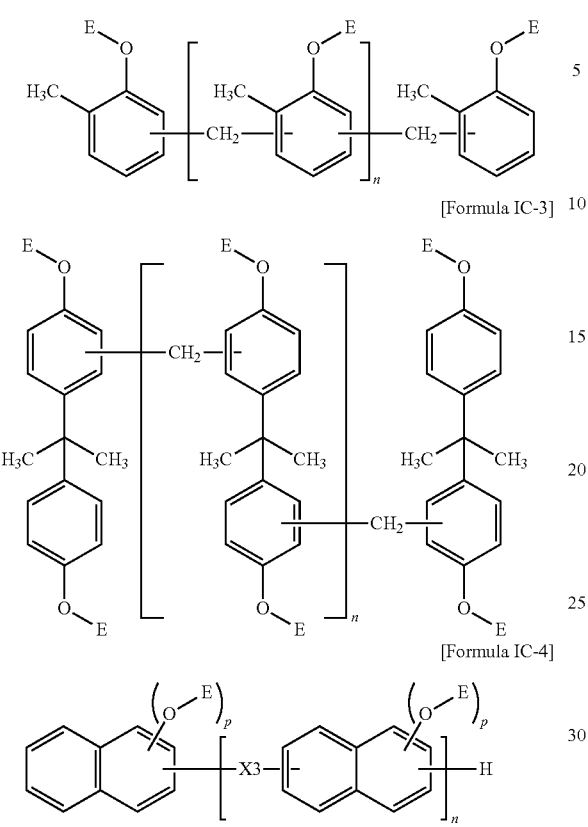

[Formula IC-3]

[Formula IC-4]

In the above Formula IC-4, x3 is

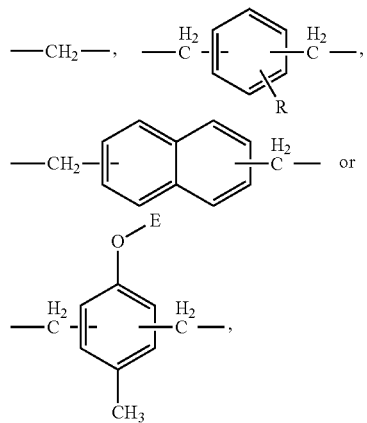

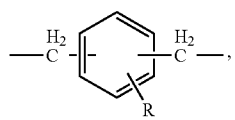,

R is a linear or a branched alkyl group of C1-C10.

In the above Formulae IC-1 to IC-4, at least two of a plurality of E are the following Formula B2, and the remainder thereof are hydrogen. In the above Formulae IC-1, in the case that Y2 is 4A to 4E, n is an integer of at least 2, and in the case that Y2 is 4F, n is an integer of at least 1. In the above Formulae IC-2 and IC-3, n is an integer of at least 1. In the above Formula IC-4, in the case that x3 is

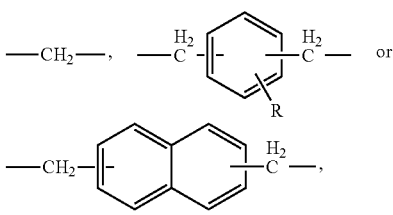

n is an integer of at least 2, and in the case that x3 is

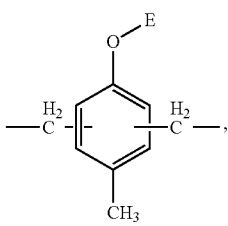

n is an integer of at least 1.

n is an integer of at least 1, for example, an integer from 1 to 1,000, and for example, an integer from 2 to 1,000 and refers to all integers in the range. Particularly, in the case that Y2 is 4A to 4E in Formula IC-1, and in the case that x3 is

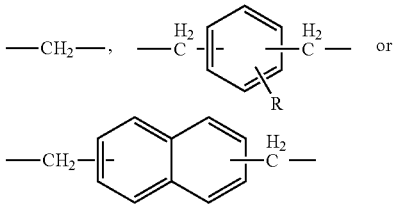

in Formula IC-4, n is an integer from 2 to 1,000. In the above Formula IC-4, p is 1 or 2.

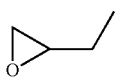

[Formula B2]

After that, in the second step, an epoxy compound of Formulae I-1 to I-4 having substituent of Formula A4 may be produced by the alkoxysilylation of one intermediate of Formulae IC-1 to IC-4 in the presence of an optional base and an optional solvent. In the second step, the reaction of the above intermediate IC and the NCO-containing alkoxysilane of the following Formula IIIB is performed so that 0.1 to 5 equivalents of the NCO-containing alkoxysilane of Formula IIIB with respect to 1 equivalent of the hydroxyl group of intermediate IC may react in the presence of an optional solvent at −20° C. to 120° C. for 1 to 72 hours.

OCN—(CH$_2$)$_m$—SiR$_1$R$_2$R$_3$  [Formula IIIB]

In the above Formula IIIB, at least one of $R_1$ to $R_3$ is an alkoxy group having 1 to 5 carbon atoms, and preferably, an ethoxy group, and the remainder thereof are an alkyl group having 1 to 10 carbon atoms, the alkoxy group and the alkyl group may be a linear or a branched, and m is an integer from 3 to 10, and preferably, an integer from 3 to 6.

In the second step reaction, since intermediate IC and the NCO-containing alkoxysilane react according to equivalent ratios on the basis of stoichiometry of the hydroxyl group of intermediate IC and the alkoxysilane, the intermediate IC and the NCO-containing alkoxysilane may react so that 0.1 to 5 equivalents of the alkoxysilane with respect to 1 equivalent of the hydroxyl group of the intermediate IC may react.

The reaction temperature and the reaction time of the second step may change depending on the kind of reactants, and the reaction may be performed, for example, within a temperature range from −20° C. to 120° C. for 1 to 72 hours to produce an epoxy compound of Formulae I-1 to I-4 having a substituent of —CONH(CH$_2$)$_n$—SiR$_1$R$_2$R$_3$.

The second step reaction may be performed in the presence of a base as occasion demands. The reaction may be performed without using a separate base; however, in this case, the reaction rate may be slow. By using the base, the reaction rate may be increased. The base used may include, for example, $K_2CO_3$, $Na_2CO_3$, $KHCO_3$, $NaHCO_3$, triethylamine and diisopropylethylamine, without limitation. These bases may be used alone or as a combination of two or more thereof. 0.1 to 5 equivalents of the base may be used based on 1 equivalent of the hydroxyl group of intermediate A3 in consideration of reaction efficiency.

The solvents used during the second step reaction may be any optional solvent. For example, the solvent may not be used if the viscosity of the reactants at the reaction temperature is appropriate for carrying out the second step reaction without using a separate solvent. That is, a separate solvent is not necessary in the case in which the viscosity of the reactants is sufficiently low, and the mixing and stirring of the reactants may be easily performed without solvents. This may be easily decided upon by a person skilled in the art. In the case in which a solvent is used, any aprotic solvent may be used, if able to dissolve the reactants properly, not inducing any adverse influence to the reaction, and being easily removed after the reaction. For example, toluene, acetonitrile, THF (tetra hydro furan), MEK (methyl ethyl ketone), DMF (dimethyl formamide), DMSO (dimethyl sulfoxide), methylene chloride (MC), or the like may be used, without limitation. These solvents may be used alone or as a mixture of two or more thereof. The content of the solvent may not be limited to being within a specific range, and an appropriate content of the solvent may be used within a range for sufficiently dissolving the reactants and not adversely affecting the reaction. A person skilled in the art may select an appropriate content of the solvent in consideration of the above-mentioned points.

An exemplary reaction scheme of Reaction 2 of Formula I-1 where Z is IA is as follows.

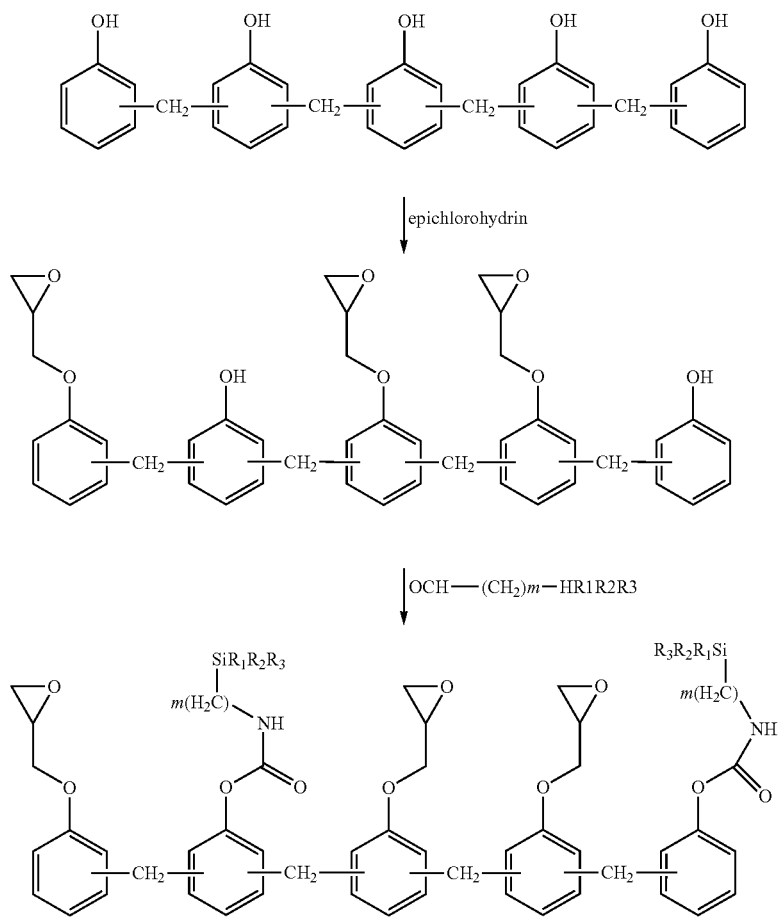

As defined in the epoxy compound of the above Formulae I-1 to I-4, at least two of a plurality of substituent A of Formulae I-1 to I-4 may have the structure of Formula A2 (that is, an epoxy group), at least one thereof may have the structure of A4 (that is an alkoxysilyl group), and the remainder thereof may be hydrogen. The extent of substitution of the epoxy group and the alkoxysilyl group with respect to Formulae I-1 to I-4 in the first reaction of the first step may be changed by controlling the number of epoxidized hydroxyl groups by controlling the equivalent of the epichlorohydrin and the reaction temperature. A person skilled in the art may control appropriately in consideration of the reactivity from the above-mentioned points.

3. Epoxy Composition

According to another embodiment of the present invention, there is provided an epoxy composition including at least one novel novolac epoxy compound selected from the group consisting of the above Formulae I-1 to I-4.

Any compositions provided in the present invention may be used in various uses such as an electronic material, for example, a semiconductor substrate such as an IC substrate, a build-up film, an encapsulating material (packaging material), an electronic part such as a printed circuit board, an adhesive, a paint, a composite, or the like, without limitation. In addition, any compositions provided in the present invention may be a curable composition and/or a curable composition including an inorganic material.

Any epoxy compositions according to any embodiments described above or later in the present invention may include any kind and/or any mixing ratio known in the art only when including at least one novel novolac epoxy compound selected from the group consisting of the above Formulae I-1 to I-4. In this case, the kind and the mixing ratio of the curing agent, the curing accelerator (catalyst), the inorganic material (filler) (for example, inorganic particles and/or a fiber), other common epoxy compounds and other additives are not limited.

Further, the epoxy composition, the cured article and/or the composite may be used with various kinds of common epoxy compounds in consideration of the controlling feature of physical properties according to the application and/or use thereof. Thus, in the epoxy compositions according to any embodiments described above or later in the present invention, the epoxy compound may include at least one novel novolac epoxy compound selected from the group consisting of the above Formulae I-1 to I-4 (hereinafter a 'novolac epoxy compound of the present invention'), and any kind of epoxy compound commonly known in this art (hereinafter a 'common epoxy compound').

The common epoxy compounds may be any kind of epoxy compounds commonly known in this art without limitation, and may be, for example, at least one epoxy compound selected from the group consisting of a glycidyl ether-based epoxy compound, a glycidyl-based epoxy compound, a glycidyl amine-based epoxy compound, a glycidyl ester-based epoxy compound, a rubber modified epoxy compound, an aliphatic polyglycidyl-based epoxy compound and an aliphatic glycidyl amine-based epoxy compound. Further, the common epoxy compound may be at least one epoxy compound selected from the group consisting of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound including bisphenol A, bisphenol F, bisphenol S, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol, a cyclo aliphatic compound, or a novolac unit, as a core structure.

For example, the common epoxy compound may be at least one epoxy compound selected from the group consisting of the glycidyl ether-based epoxy compound, the glycidyl-based epoxy compound, the glycidyl amine-based epoxy compound, the glycidyl ester-based epoxy compound, the rubber modified epoxy compound, the aliphatic polyglycidyl-based epoxy compound and the aliphatic glycidyl amine-based epoxy compound including bisphenol A, bisphenol F, bisphenol S, biphenyl, naphthalene, benzene, thiodiphenol, fluorene, anthracene, isocyanurate, triphenylmethane, 1,1,2,2-tetraphenylethane, tetraphenylmethane, 4,4'-diaminodiphenylmethane, aminophenol, a cyclo aliphatic compound, or a novolac unit, as a core structure.

Any epoxy compositions in accordance with an embodiment of the present invention may include without limitation, based on the total amount of an epoxy compound, from 1 wt % to 100 wt % of the novolac epoxy compound according to any embodiments of the present invention and from 0 wt % to 99 wt % of the common epoxy compound; for example, from 10 wt % to 100 wt % of the novolac epoxy compound of the present invention and from 0 wt % to 90 wt % of the common epoxy compound; for example, from 30 wt % to 100 wt % of the novolac epoxy compound of the present invention and from 0 wt % to 70 wt % of the common epoxy compound; for example, from 50 wt % to 100 wt % of the novolac epoxy compound of the present invention and from 0 wt % to 50 wt % of the common epoxy compound; for example, from 10 wt % to below 100 wt % of the novolac epoxy compound of the present invention and from excess of 0 wt % to 90 wt % of the common epoxy compound; for example, from 30 wt % to below 100 wt % of the novolac epoxy compound of the present invention and from excess of 0 wt % to 70 wt % of the common epoxy compound; for example, from 50 wt % to below 100 wt % of the novolac epoxy compound of the present invention and from excess of 0 wt % to 50 wt % of the common epoxy compound.

Further, in accordance with an embodiment of the present invention, an epoxy composition including at least one novel novolac epoxy compound selected from the group consisting of the above Formulae I-1 to I-4 and an inorganic material (filler) (for example, inorganic particles and/or a fiber) according to any embodiments of the present invention (hereinafter a 'composite composition') is provided. The composite composition is considered to include an epoxy composition having any kind and/or any mixing ratio commonly known in this art only when including at least one novel novolac epoxy compound selected from the group consisting of the above Formulae I-1 to I-4 and the filler. The kinds and the mixing ratios of the curing agent, the curing accelerator (catalyst), the inorganic material (filler) (for example, inorganic particles and/or a fiber) composing the epoxy composition, and the kinds of the common epoxy compound and other additives are not limited.

The above-described composite composition and any compositions described above or later according to the present invention may additionally include inorganic particles and/or a fiber.

Any inorganic particles known to be used to reinforce the physical properties of a common organic resin may be used. Examples of the inorganic particles may include, without limitation, at least one selected from the group consisting of at least one metal oxide selected from the group consisting of silica (including, for example, fused silica and crystalline silica), zirconia, titania, alumina, silicon nitride and aluminum nitride, T-10 type silsesquioxane, ladder type silsesquioxane, and cage type silsesquioxane. The inorganic particles may be used alone or as a mixture of two or more thereof.

In the case that particularly a large content of the silica is mixed, the fused silica is preferably used. The fused silica may have any shape among a cataclastic shape and a spherical shape. However, the spherical shape is preferable to order to increase the fill factor of the fused silica and to restrain the increase of the melt viscosity of a composite material.

The inorganic particles having a particle size of 0.5 nm to several tens of μm (for example, from 50 μm to 100 μm) may be used in consideration of the use of a composite, particularly, the dispersibility of the inorganic particles, or the like. Since the dispersibility of the inorganic particle in the epoxy matrix may be different according to the particle size, the inorganic particles having the above-described size may preferably be used. In addition, the increase of size distribution of the inorganic particles to be mixed is preferable to increase the fill factor of the inorganic particles.

In the epoxy composition in accordance with an embodiment of the present invention, the fill factor of the inorganic particles with respect to the epoxy compound may be appropriately controlled in consideration of the CTE decrease of an epoxy composite and an appropriate viscosity required while applying. For example, the content of the inorganic particles may be 5 wt % to 95 wt %, for example, 5 wt % to 90 wt %, for example, 10 wt % to 90 wt %, for example, 30 wt % to 95 wt %, for example, 30 wt % to 90 wt %, for example, 5 wt % to 60 wt %, for example, 10 wt % to 50 wt % based on the total content of the solid content of the epoxy compound (based on the total content of the epoxy cured article for the epoxy cured article).

More particularly, in an exemplary embodiment, when the epoxy composition is used as a semiconductor packaging, or the like, the content of the inorganic particles may be, for example, 30 wt % to 95 wt %, for example, 30 wt % to 90 wt %, without limitation, based on the total solid content of the epoxy formulation (based on the total content of the epoxy cured article for the epoxy cured article) in consideration of the CTE value and material processability. In other exemplary embodiments, when the epoxy composition is used in a IC substrate, the content of the inorganic particles may be 5 wt % to 60 wt %, for example, 10 wt % to 50 wt % based on the total solid content of the epoxy compound (based on the total content of the epoxy cured article for the epoxy cured article) considering the CTE value and the modulus of the substrate.

Meanwhile, when the fiber is used as the inorganic material, a composite may mainly be obtained by an impregnation of the fiber within the epoxy composition. Thus, the size of the fiber may not be specifically limited. Any kind of fiber commonly used in this field may be used and dimensions thereof are not limited.

Any commonly used fibers used for improving physical properties of a common cured organic resin may be used without limitation. Particularly, a glass fiber, an organic fiber or a mixture thereof may be used. In addition, the term 'glass fiber' used in this application may include a glass fiber fabric, a glass fiber non woven product, or the like, as well as the glass fiber. Examples of the glass fibers may include, without limitation, an E-glass fiber, a T-glass fiber, an S-glass fiber, an NE-glass fiber, an E-glass fiber, a D-glass fiber, a quartz glass fiber, or the like. For example, the E- or T-glass fiber may be included. An organic fiber may include at least one selected from the group consisting of a liquid crystal polyester fiber, a polyethyleneterephthalate fiber, a wholly aromatic fiber, a polyoxybenzasol fiber, a nylon fiber, a polyethylene naphthalate fiber, a polypropylene fiber, a polyether sulfone fiber, a polyvinylidene fluoride fiber, a polyethylene sulfide fiber and a polyether ether ketone fiber. These fibers may be used alone or as a combination of two or more.

The content of the fiber in the epoxy composition according to the present invention, for example, in a glass fiber composite of epoxy composition, may be 10 wt % to 90 wt %, for example, 30 wt % to 70 wt %, in addition, for example, 35 wt % to 65 wt % based on the total weight of the solid content of the epoxy composition. In addition, the content of the fiber in the cured article of the epoxy composition, for example, in a glass fiber composite, may be 10 wt % to 90 wt %, for example, 30 wt % to 70 wt %, in addition, for example, 35 wt % to 65 wt % based on the total content of the cured article. Thus, the resin content may be 10 wt % to 90 wt %, for example, 30 wt % to 70 wt %, in addition, for example, 35 wt % to 65 wt %. The content of the fiber within the above-described range may be preferred in consideration of the increase in heat resistance and the processability. Meanwhile, in the epoxy composition, the cured article, or the like, including the fiber, solid parts excluding the fiber from the total solid content is referred to as the resin. In the epoxy composition including the fiber, the remaining amount other than the fiber is the resin content.

Further, in the epoxy composition including the fiber may additionally include inorganic particles as occasion demands. In this case, the inorganic particles may be included by 1 wt % to 70 wt % based on the total amount of resin in consideration of the improvement of the physical properties and processability. In this case, the kind of the inorganic particles is not specifically limited, and any inorganic particles known in this art may be used. For example, the above-described inorganic particles may be used.

According to further another embodiment of the present invention, an epoxy composition including at least one novel novolac epoxy compound selected from the group consisting of the above Formulae I-1 to I-4 according to any embodiments of the present invention and a curing agent is provided (hereinafter a 'curing agent-containing composition'). Any curing agent-containing compositions may include an epoxy composition having any kind and/or any mixing ratio known in the art only when including at least one novel novolac epoxy compound selected from the group consisting of the above Formulae I-1 to I-4 and a curing agent. However, the kinds and the mixing ratios of the curing agent, the curing accelerator (catalyst), the inorganic material (filler) (for example, inorganic particles and/or fibers), other common epoxy compounds and other additives composing the epoxy composition are not limited.

According to further another embodiment of the present invention, an epoxy composition including at least one novel novolac epoxy compound selected from the group consisting of the above Formulae I-1 to I-4 according to any embodiments of the present invention and an alkoxysilyl reaction catalyst (hereinafter a 'reaction catalyst') is provided (hereinafter a 'reaction catalyst-containing composition'). Any reaction catalyst-containing compositions may include an epoxy composition having any kind and/or any mixing ratio known in the art only when including at least one novel novolac epoxy compound selected from the group consisting of the above Formulae I-1 to I-4 and a reaction catalyst. However, the kinds and the mixing ratios of the curing agent, the curing accelerator (catalyst), the inorganic material (filler) (for example, inorganic particles and/or fibers), other common epoxy compounds and other additives composing the epoxy composition are not limited. In the case that the alkoxysilyl reaction catalyst is included, improved processability (for example, a rapid curing rate and/or a low curing temperature) may be expected.

The curing agent-containing composition and the reaction catalyst-containing composition may also include the common epoxy compound as the epoxy compound. In this case, the kind of the common epoxy compound and the mixing ratios of the alkoxysilylated epoxy compound and the common epoxy compound are the same as described above.

When a curing agent is included in the curing agent-containing composition and the composition according to an embodiment of the present invention, any curing agents commonly known as a curing agent of an epoxy compound may be used. For example, an amine, a phenol, an anhydride compound may be used, without limitation.

More particularly, an aliphatic amine, an alicyclic amine, an aromatic amine, other amines and a modified amine may be used as the amine curing agent without limitation. In addition, an amine compound including two or more primary amine groups may be used. Particular examples of the amine curing agents may include at least one aromatic amine selected from the group consisting of 4,4'-dimethylaniline (diamino diphenyl methane, DAM or DDM), and diamino diphenyl sulfone (DDS), and m-phenylene diamine, at least one aliphatic amine selected from the group consisting of diethylene triamine (DETA), diethylene tetramine, triethylene tetramine (TETA), m-xylene diamine (MXTA), methane diamine (MDA), N,N'-diethylenediamine (N,N'-DEDA), tetraethylenepentaamine (TEPA), and hexamethylenediamine, at least one alicyclic amine selected from the group consisting of isophorone diamine (IPDI), N-aminoethyl piperazine (AEP), bis(4-amino 3-methylcyclohexyl)methane, and larominc 260, other amines such as dicyanamide (DICY), or the like, and a modified amine such as a polyamide-based compound, an epoxide-based compound, or the like.

Examples of the phenol curing agent may include, without limitation, a tri-functional phenol novolac resin, a cresol novolac resin, a bisphenol A novolac resin, a xylene novolac resin, a triphenyl novolac resin, a biphenyl novolac resin, a phenol p-xylene resin, a phenol 4,4'-dimethylbiphenylene resin, a phenol dicyclopentadiene novolac resin, a dicyclopentadiene-phenol (DCPD-phenol) novolac resin, a xylok (p-xylene modified) resin, a biphenyl-based phenol resin, a naphthalene-based phenol novolac resin, a triazine-based compound, dihydroxy naphthalene, dihydroxy benzene, or the like.

Examples of the anhydride curing agent may include, without limitation, an aliphatic anhydride such as dodecenyl succinic anhydride (DDSA), poly azelaic poly anhydride, or the like, an alicyclic anhydride such as hexahydrophthalic anhydride (HHPA), methyl tetrahydrophthalic anhydride (MeTHPA), methylnadic anhydride (MNA), or the like, an aromatic anhydride such as trimellitic anhydride (TMA), pyromellitic acid dianhydride (PMDA), benzophenonetetracarboxylic dianhydride (BTDA), or the like, and a halogen-based anhydrous compound such as tetrabromophthalic anhydride (TBPA), chlorendic anhydride, or the like.

In general, the crosslinking density of an epoxy composite may be controlled by the extent of reaction of the curing agent and the epoxy group. According to the target crosslinking density, the stoichiometric ratio of the curing agent to epoxy compound may be controlled. For example, when an amine curing agent is used, the stoichimetric equivalent ratio of the epoxy to amine may be preferably controlled to 0.5 to 2.0, for example, 0.8 to 1.5 in a reaction of the amine curing agent with the epoxy group.

Though the mixing ratio of the curing agent has been explained with respect to the amine curing agent, a phenol curing agent, an anhydride curing agent and any curing agents for curing epoxy compounds not separately illustrated in this application but used for curing may be used by appropriately mixing a stoichiometric amount according to the chemical reaction of the epoxy functional group and the reactive functional group of the curing agent based on the concentration of the total epoxy group in the epoxy composition according to the desired range of the crosslinking density. The above-described elements are commonly known in this field.

As a cationic photo curing agent (also referred to as a photo initiator), commonly known photo curing agents in this field may be used and for example, an aromatic phosphonium salt, an aromatic iodonium salt, an aromatic sulfonium salt, etc. may be illustrated without limitation. Particularly, diphenyliodonium tetrakis(pentafluorophenyl) borate, diphenyliodonium hexafluorophosphate, diphenyliodonium hexafluoroantimonate, di(4-nonylphenyl) iodonium hexafluorophosphate, triphenylsulfonium hexafluorophosphate, triphenylsulfonium hexafluoroantimonate, triphenylsulfonium tetrakis(pentafluorophenyl)borate, 4,4'-bis[diphenylsulfonio]diphenylsulfide bishexafluorophosphate, 4,4'-bis[di(8-hydroxyethoxy)phenylsulfonio]diphenylsulfide bishexafluorophosphate, etc. may be used. The photo curing agent may be used in a ratio of 0.5 to 20 parts per hundred (phr) (parts by weight on the basis of 100 parts by weight of the epoxy compound), may preferably be at least 1 phr, and may preferably be at most 15 phr.

An optional curing accelerator (catalyst) may be additionally included as occasion demands to promote the curing reaction in any epoxy compositions provided in the present invention. Any curing accelerators (catalysts) commonly used for curing an epoxy composition in this art may be used without limitation, for example, an imidazoles, a tertiary amines, a quaternary ammonium compounds, an organic acid salt, a phosphorous compounds may be used as curing accelerators.

More particularly, for example, the imidazole-based curing accelerator such as dimethylbenzylamine, 2-methylimidazole (2MZ), 2-undecylimidazole, 2-ethyl-4-methylimidazole (2E4M), 2-phenylimidazole, 1-(2-cyanoethyl)-2-alkyl imidazole, and 2-heptadecylimidazole (2HDI); the tertiary amine-based curing accelerator such as benzyldimethylamine (BDMA), tris dimethylaminomethyl phenol (DMP-30), and triethylenediamine; the quaternary ammonium-based curing accelerator such as tetrabutylammonium bromide, or the like; diazabicycloundecene (DBU), or an organic acid of DBU; the phosphor compound-based curing accelerator such as triphenylphosphine, phosphoric acid ester, or the like, and a Lewis acid such as $BF_3$-monoethylamine ($BF_3$-MEA), or the like, may be illustrated without limitation. Latent curing accelerators may also be used, which are provided by microcapsulating the accelerators and forming complex salts with accelerators, for example. These compounds may be used alone or a mixture of two or more thereof according to curing conditions.

The mixing content of the curing accelerator may be a commonly applied mixing amount in this art without limitation. For example, 0.1 to 10 phr (parts per hundred parts of resin, parts by weight based on 100 parts by weight of the epoxy compound), for example, 0.2 to 5 phr of the curing accelerator based on the epoxy compound may be used. The above-described range of the curing accelerator may be preferably used in consideration of curing reaction accelerating effect and the control of curing reaction rate. Through using the above-described range of the curing accelerator, the curing may be rapidly achieved, and the improvement of working throughput may be expected.

When the reaction catalyst for alkoxysilyl group is included in the curing catalyst-containing composition and a composition according to any embodiments of the present invention, the reaction catalyst for alkoxysilyl group may be at least one selected from the group consisting of at least one inorganic acid selected from the group consisting of, for example, nitric acid, sulfuric acid, hydrochloric acid, acetic acid and phosphoric acid, ammonia, KOH, $NH_4OH$, amine, a transition metal alkoxide, a metal oxide, an organic acid salt and halide of a metal, and a tin compound (for example, dibutyltin dilaurate, tin octylate, tin(II) 2-ethylhexanoate, or the like). These compounds may be used alone or as a mixture of two or more thereof. The mixing ratio of the reaction catalyst for alkoxysilyl group is not specifically limited; however, 0.01 phr to 10 phr of the reaction catalyst for alkoxysilyl group may be used with respect to the epoxy compound of the present invention in consideration of reactivity.

In the composition including the reaction catalyst for alkoxysilyl group, water may be additionally included to increase the efficiency of the alkoxysilyl reaction catalyst. The mixing ratio is not specifically limited; however, 0.01 to 20 equivalents of water may be included with respect to 1 equivalent of the alkoxysilyl group in consideration of the efficiency and reactivity as the catalyst.

In the epoxy composition, other additives such as a releasing agent, a surface treating agent, a flame retardant, a plasticizer, bactericides, a leveling agent, a defoaming agent, a colorant, a stabilizer, a coupling agent, a viscosity controlling agent, a diluent, a rubber, a thermoplastic resin, or the like may be mixed to control the physical properties of the epoxy composition within the range of undamaging the physical properties of the epoxy composition as occasion demands.

For example, when a thin film is formed using any compositions of the present invention, and when forming a thin layer using a composition having insufficient flexibility, the thin layer thus formed may be brittle, and cracks may be easily generated. This phenomenon may be exhibited when, for example, the composition of the present invention includes a large amount of inorganic particles. Thus, to improve the processability as the thin film by imparting the composition with the solubility, the rubber and/or the thermoplastic resin may be added to the epoxy composition of the present invention. As the thermoplastic resin and a rubber-modified epoxy resin, commonly known resins in this field may be used. As rubber particles, any rubbers known in this field may be used only if the rubber particles are not dissolved in a solvent used in the composition and maintains a dispersed state in the composition. The kind of the rubber may include, for example, an acrylonitrile butadiene rubber, a butadiene rubber, an acryl rubber, core-shell type rubber particles, a cross-linked acrylonitrile butadiene rubber, cross-linked styrene butadiene rubber particles, acryl rubber particles, or the like, without limitation. These materials may be used alone, or at least two thereof may be used at the same time. When a rubber having a particle shape is used, the mean particle diameter may preferably be from 0.005 to 1 µm, and more preferably be from 0.2 to 0.6 µm in consideration of the improvement of physical properties. The rubber particles may be mixed in an amount ratio, for example, of 0.5 to 10 wt % based on the solid content of the epoxy composition in consideration of physical properties.

As the thermoplastic resin, a phenoxy resin, a polyvinyl acetal resin, a polyimide resin, a polyamideimide resin, a polyether sulfone resin, a polysulfone resin, or the like may be used, without limitation. These materials may be used alone or at least two thereof may be used at the same time. The thermoplastic resin may be mixed in a ratio of, for example, from 0.5 to 60 wt %, and preferably from 3 to 50 wt % based on the solid content of the epoxy composition in consideration of physical properties.

As described above, the term "epoxy composition" used in the present application is understood to include an epoxy compound of the present invention and other constituents composing the epoxy composition, for example, an optional curing agent, a curing accelerator (catalyst), an inorganic material (filler) (for example, inorganic particles and/or a fiber), other common epoxy compounds, a solvent and other additives mixed as occasion demands in this field. In general, the solvent may be optionally used to control the amount and/or the viscosity of the solid content of the epoxy composition in consideration of the processability of the epoxy composition, and the like. Meanwhile, the "total solid content of the epoxy composition" used in the present invention refers to the total amount of a solid component other than a liquid component such as solvents composing the epoxy composition.

The epoxy composition provided in accordance with an exemplary embodiment of the present invention may be used as an electronic material. The electronic material may include, for example, a substrate for semiconductor, a film, a prepreg, a laminate obtained by placing a metal layer on a base layer formed by using the composition of the present invention, a substrate, an encapsulating material (a packaging material), a build-up film (substrate), a printed circuit board, or the like. In addition, the epoxy composition may be used in various applications such as an adhesive, a paint and a composite material. In accordance with other exemplary embodiments of the present invention, an electronic material including or manufactured by using a composition including the novolac epoxy compound of the present invention is provided. Further, a semiconductor apparatus including or manufactured by essentially using or using the electronic material, is provided. Particularly, the semiconductor apparatus may be a semiconductor apparatus including a printed circuit board (for example, for installing a semiconductor device) including or manufactured by essentially using or using the composition including the novolac epoxy compound of the present invention and/or may be a semiconductor apparatus including a semiconductor packaging material. In addition, a curing agent, an adhesive, a paint or a composite material including or manufactured by essentially using or using any epoxy compositions provided in any embodiments of the present invention, may be provided.

In accordance with other exemplary embodiments of the present invention, a cured article including or manufactured by essentially using or using the epoxy composition provided in accordance with an exemplary embodiment of the present invention may be provided. In the case that applying the epoxy composition provided in an exemplary embodiment of the present invention is practically used, for example, when the epoxy composition is applied as the electronic material, or the like, a cured article formed of the epoxy composition may be used. In this art, the cured article formed of the composition including the epoxy compound and the filler of the inorganic component may be commonly referred to as a composite.

The novolac epoxy compound provided in above-described exemplary embodiments of the present invention may show good heat resistance in the composite and/or good flame retardancy in the cured article.

Particularly, the composite may exhibit a low CTE, for example, 15 ppm/° C. or less, for example, 12 ppm/° C. or less, for example, 10 ppm/° C. or less, for example, 8 ppm/° C. or less, for example, 6 ppm/° C. or less, for example, 4 ppm/° C. or less. The property of the composite are better as the CTE value is smaller, and the lower value of the CTE is not particularly delimited.

For example, a composite including any novolac epoxy compounds in accordance with exemplary embodiments of the present invention as the epoxy compound, and a glass fiber, for example, an E-glass fiber and/or a T-glass fiber as the inorganic material, and having the resin content (the resin content may or may not include inorganic particles) of 30 wt % to 60 wt % may have a CTE of 10 ppm/° C. or less, for example, 8 ppm/° C. or less, for example, 6 ppm/° C. or less, for example, 4 ppm/° C. or less.

In addition, for example, a composite including any novolac epoxy compounds in accordance with exemplary embodiments of the present invention as the epoxy compound, and inorganic particles as the inorganic material, for example, silica particles of 60 wt % to 80 wt %, for example, 70 wt % to 80 wt %, may have a CTE of 20 ppm/° C. or less, for example, 15 ppm/° C. or less, for example, 10 ppm/° C. or less, for example, 8 ppm/° C. or less, for example, 6 ppm/° C. or less, for example, 4 ppm/° C. or less.

In addition, Tg of the composite (a cured article including an inorganic material) according to the present invention may be higher than 100° C., for example, 130° C. or higher, in addition, for example, 250° C. or higher. Otherwise, the composite may be Tg-less. The physical properties of the composite are better when the Tg is higher, and the upper value of the Tg is not particularly delimited.

Meanwhile, the cured article formed by using the novolac epoxy compound (a cured article excluding an inorganic material) according to the present invention may have a CTE of 50 ppm/° C. to 150 ppm/° C.

In the present application, the values delimited by the range include the lower limit, the upper limit, any sub ranges in the range, and all numerals included in the range, unless otherwise specifically stated. For example, C1 to C10 is understood to include all of C1, C2, C3, C4, C5, C6, C7, C8, C9 and C10. In addition, in the case when the lower limit or the upper limit of the numerical range is not defined, it would be found that the smaller or the larger value may provide the better properties. In addition, in the case when the limit is not defined, any values may be included. For example, CTE of 4 ppm/° C. or less is understood to include every values in the range such as the CTE of 4, 3.5, 3, 2.7, 2, 1.4, 1, 0.5 ppm/° C., or the like.

Hereinafter, the present invention will be explained in detail referring to examples. The following examples are for illustrating the present invention and not for limiting the present invention.

Synthetic Example 1

(1) First Step

In a two-necked flask, 10 g of a phenol novolac resin (Meiwa plastic Ind., trade name HF-1M) and 9.35 g of NaOH in 250 ml of DMSO were stirred at room temperature for 30 minutes. Then, the temperature thereof was lowered to 0° C., and 2.83 g of allyl bromide was slowly added to the flask, followed by stirring at room temperature for 1 hour. The temperature thereof was lowered to 0° C. again, and 34.6 g of epichlorohydrin was slowly added, followed by stirring at room temperature for 24 hours. After completing the reaction, the reaction mixture was worked-up using 400 ml of ethyl acetate and a saturated NaCl solution. An organic layer was separated and remaining $H_2O$ was removed with $MgSO_4$. The solvent was evaporated and dried using a vacuum pump to produce an intermediate. The NMR analysis result of the intermediate thus obtained is as follows.

$^1$H NMR (400 MHz, $CDCl_3$): δ=7.14-6.70 (m, 21.68H), 6.04-6.00 (m, 2.09H), 5.41-5.20 (m, 3.59H), 4.49-4.47 (m, 3.23H), 4.17-3.80 (m, 21.11H), 3.32-3.29 (m, 5.39H), 2.73-2.60 (m, 10.17H)

(2) Second Step 10 g of the product obtained in the first step, 71 mg of $PtO_2$, 3.08 g of triethoxysilane (TCI, the same hereinafter) and 150 ml of toluene were added to a flask, followed by stirring at room temperature for 5 minutes. The temperature thereof was set at 80° C., and heating while stirring was conducted for 24 hours. After completing the reaction, the reaction mixture was cooled to room temperature, and an inorganic material was removed using a celite filter. Toluene was removed through evaporation and completely dried using a vacuum pump to produce a novolac epoxy compound having an ethoxysilyl group. The concentration ratio of epoxy:silyl function groups of the novolac epoxy compound having the ethoxysilyl group thus obtained was 3.86:1, and NMR data are as follows.

$^1$H NMR (400 MHz, $CDCl_3$): δ=7.15-6.70 (m, 21.68H), 4.20-3.79 (m, 33.2H), 3.33-3.25 (m, 4.8H), 2.73-2.59 (m, 9.7H), 1.82-1.70 (m, 2.4H), 1.24-1.20 (m, 11.93H), 0.80-0.61 (m, 2.49H)

The reaction scheme of the above Synthetic Example 1 is as follows. In the reaction scheme, n=4 for convenience; however, the epoxy compound of this synthetic example is not limited thereto. A final product corresponding to the repeating unit of a starting material may be obtained, and the concentration of epoxy:silyl function groups in a final product was 3.86:1. The above-described points will be applied in the following synthetic examples.

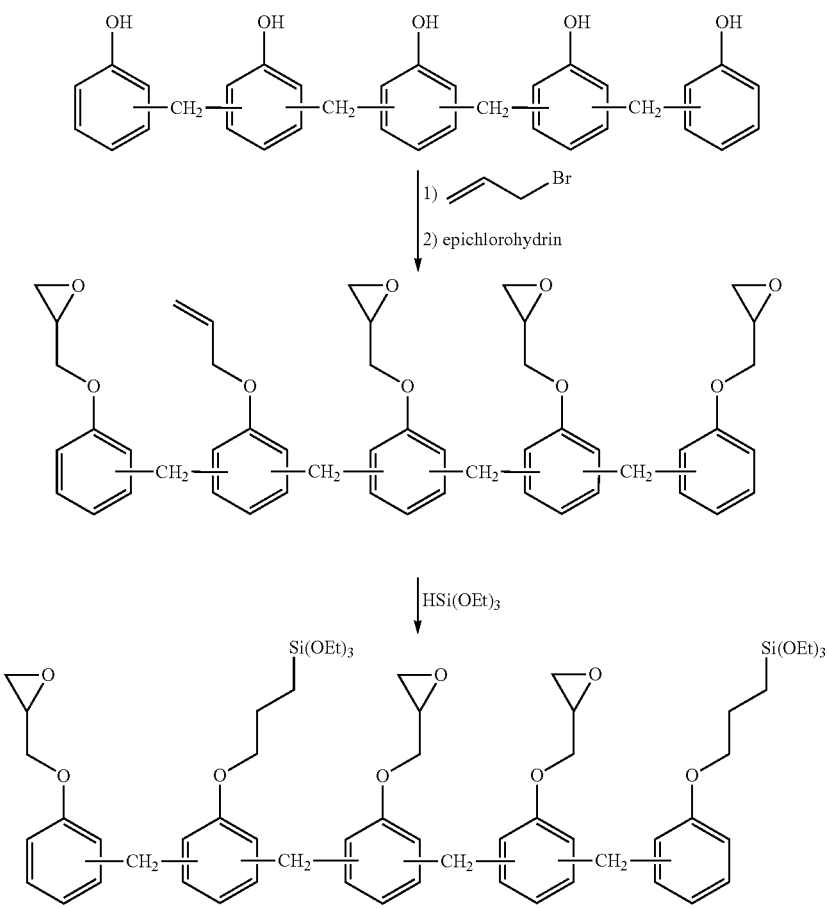

Synthetic Example 2

(1) First Step

The same procedure was performed as the first step of Synthetic Example 1 except for using 3.39 g of allyl bromide to produce an intermediate. The NMR analysis result of the intermediate thus obtained is as follows.

$^1$H NMR (400 MHz, CDCl$_3$): δ=7.14-6.70 (m, 21.68H), 6.04-6.00 (m, 2.05H), 5.41-5.20 (m, 3.71H), 4.49-4.47 (m, 3.28H), 4.17-3.80 (m, 22.76H), 3.32-3.29 (m, 5.07H), 2.73-2.60 (m, 9.85H)

(2) Second Step

The same procedure was performed as the second step of Synthetic Example 1 except for using 98 mg of PtO$_2$ and 4.24 g of triethoxysilane. The concentration ratio of epoxy:silyl function groups in the novolac epoxy compound having an ethoxysilyl group thus obtained was 2.9:1, and NMR data are as follows.

$^1$H NMR (400 MHz, CDCl$_3$): δ=7.15-6.70 (m, 21.68H), 4.20-3.79 (m, 38.4H), 3.33-3.25 (m, 8.6H), 2.73-2.59 (m, 9.0H), 1.82-1.70 (m, 3.4H), 1.24-1.20 (m, 15.2H), 0.80-0.61 (m, 3.1H)

Synthetic Example 3

(1) First Step

The same procedure was performed as the first step of Synthetic Example 1 except for using 5.65 g of allyl bromide to produce an intermediate. The NMR analysis result of the intermediate thus obtained is as follows.

$^1$H NMR (400 MHz, CDCl$_3$): δ=7.14-6.70 (m, 21.68H), 6.04-6.00 (m, 3.35H), 5.41-5.20 (m, 6.8H), 4.49-4.47 (m, 6.93H), 4.17-3.80 (m, 23.52H), 3.32-3.29 (m, 3.5H), 2.73-2.60 (m, 8.5H)

(2) Second Step

The same procedure was performed as the second step of Synthetic Example 1 except for using 145 mg of PtO$_2$ and 6.32 g of triethoxysilane. The concentration ratio of epoxy:silyl function groups in the novolac epoxy compound having an ethoxysilyl group thus obtained was 1:1, and NMR data are as follows.

$^1$H NMR (400 MHz, CDCl$_3$): δ=7.15-6.70 (m, 21.68H), 4.20-3.79 (m, 45.5H), 3.33-3.25 (m, 12.2H), 2.73-2.59 (m, 8.5H), 1.82-1.70 (m, 6.4H), 1.24-1.20 (m, 32.3H), 0.80-0.61 (m, 6.7H)

Synthetic Example 4

(1) First Step

In a two-necked flask, 10 g of a phenol novolac resin (Meiwa plastic Ind., trade name HF-1M) and 2.62 g of NaOH in 250 ml of DMSO were stirred at room temperature for 30 minutes. Then, the temperature thereof was lowered to 0° C., and 34.6 g of epichlorohydrin was slowly added to the flask, followed by stirring at room temperature for 24 hour. After completing the reaction, the reaction mixture was worked-up using 400 ml of ethyl acetate and a saturated NaCl solution. An organic layer was separated and remaining H₂O was removed with MgSO₄. The solvent was evaporated and dried using a vacuum pump to produce an intermediate. The NMR analysis result of the intermediate thus obtained is as follows.

a celite filter, and evaporation was performed to produce a final product having the concentration ratio of epoxy:silyl function groups of 2:1.

$^1$H NMR (400 MHz, CDCl$_3$): δ=7.16-6.69 (m, 21.68H), 5.25-5.23 (br s, 2.3H), 4.20-3.72 (m, 33.11H), 3.39-3.28 (m, 9.2H), 2.79-2.56 (m, 10.1H), 1.75-1.66 (m, 4.76H), 1.26-1.22 (m, 20.2H), 0.72-0.64 (m, 4.51H)

The reaction scheme of the above Synthetic Example 4 is as follows.

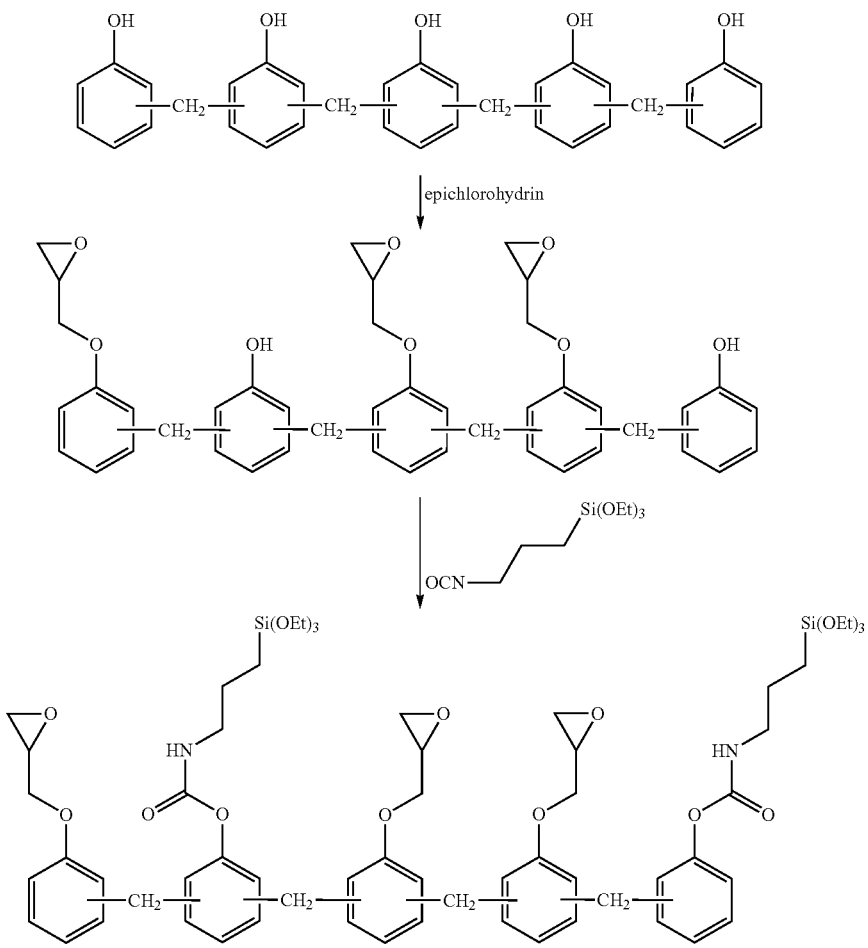

$^1$H NMR (400 MHz, CDCl$_3$): δ=7.15-6.69 (m, 21.68H), 4.18-3.74 (m, 20.31H), 3.36-3.31 (m, 4.6H), 2.75-2.59 (m, 9.3H)

(2) Second Step 10 g of the intermediate obtained in the first step, 5.4 g of diisopropylethylamine and 200 ml of methylene chloride were added to a flask, followed by stirring at room temperature. Then, 7.0 g of 3-(triethoxysilyl)propyl isocyanate (TCI, the same hereinafter) was added thereto at room temperature, followed by heating to 60° C. and carrying out a reaction for 12 hours. After completing the reaction, the reaction mixture was cooled to room temperature and worked-up using H₂O. An organic layer was separated, and MgSO₄ was added to the organic layer thus separated to remove remaining H₂O. The organic layer was filtered using Synthetic Example 5

(1) First Step

In a two-necked flask, 10 g of xyloc (Milex, XLC-4L), 6.08 g of NaOH and 200 ml of DMSO were added and stirred at room temperature for 30 minutes. Then, the temperature thereof was lowered to 0° C., and 2.20 g of allyl bromide was slowly added thereto, followed by stirring at room temperature for 1 hour. Then, the temperature thereof was lowered to 0° C. again, and 22.5 g of epichlorohydrin was slowly added, followed by stirring at room temperature for 24 hours. After completing the reaction, the reaction mixture was worked-up using 400 ml of ethyl acetate and a saturated NaCl solution. An organic layer was separated and remaining H₂O was removed with MgSO₄. The solvent was evaporated and dried using a vacuum pump to produce an intermediate. The NMR analysis result of the intermediate thus obtained is as follows.

$^1$H NMR (400 MHz, CDCl$_3$): δ=7.08-6.68 (m, 19.91H), 6.04-6.00 (m, 1.04H), 5.41-5.20 (m, 2.10H), 4.49-4.47 (m, 2.12H), 4.17-3.66 (m, 12.92H), 3.32-3.29 (m, 2.06H), 2.73-2.60 (m, 4.74H)

(2) Second Step 10 g of the intermediate synthesized in the first step, 63.7 mg of PtO$_2$, 2.76 g of triethoxysilane and 150 ml of toluene were added to a flask, followed by stirring at room temperature for 5 minutes. Then, the temperature thereof was set at 80° C., and the reaction mixture was heated while stirring for 24 hours. After completing the reaction, the reaction mixture was cooled to room temperature and an inorganic material was removed using a celite filter. Toluene was removed through evaporation, and the product was completely dried using a vacuum pump to produce a final product having the concentration ratio of epoxy:silyl function groups of 2.1:1. The NMR data of the final product are as follows.

$^1$H NMR (400 MHz, CDCl$_3$): δ=7.08-6.68 (m, 19.91H), 4.20-3.79 (m, 20.84H), 3.33-3.25 (m, 4.46H), 2.73-2.59 (m, 4.64H), 1.82-1.70 (m, 2.38H), 1.24-1.20 (m, 10.72H), 0.80-0.61 (m, 2.17H)

The reaction scheme of the above Synthetic Example 5 is as follows.

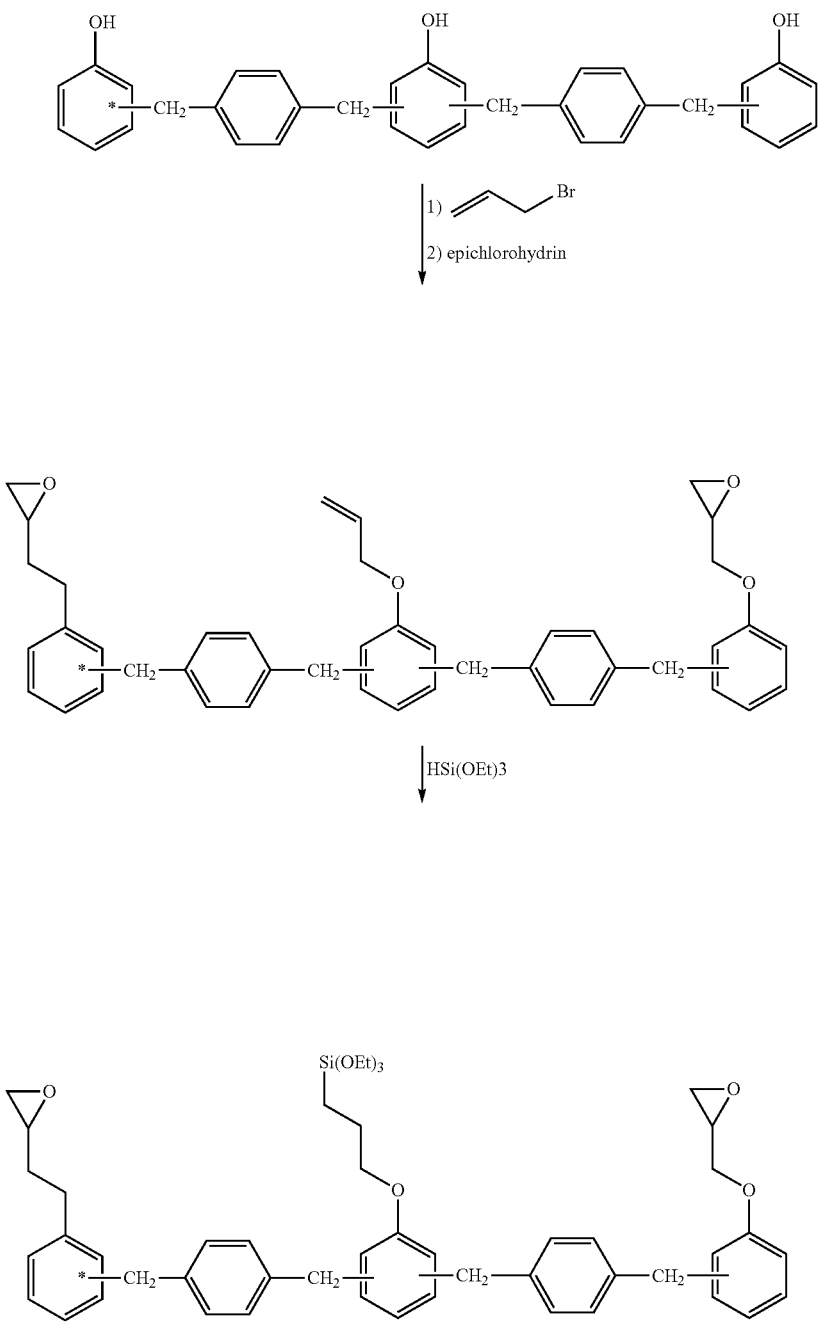

Synthetic Example 6

(1) First Step

In a two-necked flask, 10 g of xyloc (Milex, XLC-4L), 4.88 g of NaOH and 200 ml of DMSO were added and stirred at room temperature for 30 minutes. Then, the temperature thereof was lowered to 0° C., and 5.64 g of epichlorohydrin was slowly added, followed by stirring at room temperature for 24 hours. After completing the reaction, the reaction mixture was worked-up using 400 ml of ethyl acetate and a saturated NaCl solution. An organic layer was separated and remaining $H_2O$ was removed with $MgSO_4$. Solvents were evaporated and dried using a vacuum pump to produce an intermediate. The NMR analysis result of the intermediate thus obtained is as follows.

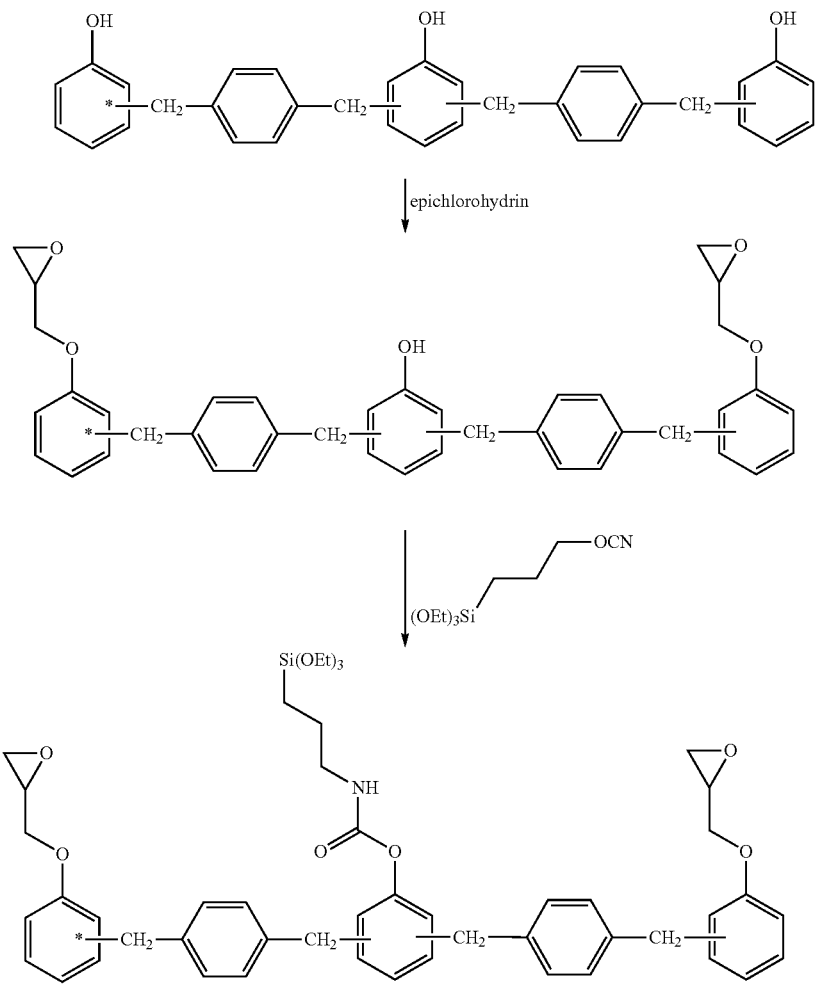

$^1$H NMR (400 MHz, $CDCl_3$): δ=9.33-9.17 (br, 0.82H), 7.08-6.68 (m, 19.91H), 4.17-3.66 (m, 12.52H), 3.32-3.29 (m, 4.56H), 2.73-2.60 (m, 8.74H)

(2) Second Step 10 g of the intermediate synthesized in the first step, 7.09 g of diisopropylethylamine, 9.05 g of 3-(triethoxysilyl) propyl isocyanate and 200 ml of methylene chloride were added to a two-necked flask at room temperature, followed by stirring at 75° C. for 18 hours. After completing the reaction, the reaction mixture was cooled to room temperature and worked-up using 400 ml of ethyl acetate and a saturated $NH_4Cl$ solution. An organic layer was separated, and remaining $H_2O$ was removed with $MgSO_4$. After performing evaporation, the product was completely dried using a vacuum pump to produce a final product having the concentration ratio of epoxy:silyl function groups of 2.1:1. The NMR data of the final product are as follows.

$^1$H NMR (400 MHz, $CDCl_3$): δ=7.08-6.68 (m, 19.91H), 5.09-5.02 (br, 1.26H), 4.20-3.79 (m, 23.84H), 3.32-3.12 (m, 5.73H), 2.73-2.60 (m, 5.44H), 1.72-1.54 (m, 2.77), 1.24-1.20 (m, 12.54H), 0.80-0.61 (m, 2.64H)

The reaction scheme of the above Synthetic Example 6 is as follows.

Synthetic Example 7

(1) First Step

In a two-necked flask, 10 g of a cresol novolac resin (Nippon kayaku Co., trade name EOCN-1020-55) and 5.10 g of NaOH in 250 ml of DMSO were stirred at room temperature for 30 minutes. Then, the temperature thereof was lowered to 0° C., and 1.85 g of allyl bromide was slowly added to the flask, followed by stirring at room temperature for 1 hour. The temperature thereof was lowered to 0° C. again, and 18.88 g of epichlorohydrin was slowly added, followed by stirring at room temperature for 24 hours. After completing the reaction, the reaction mixture was worked-up using 400 ml of ethyl acetate and a saturated NaCl solution. An organic layer was separated and remaining $H_2O$ was removed with $MgSO_4$. The solvent was evaporated and dried using a vacuum pump to produce an intermediate. The NMR analysis result of the intermediate thus obtained is as follows.

$^1$H NMR (400 MHz, DMSO): δ=7.02-6.89 (m, 10H), 6.05-6.01 (m, 1.25H), 5.43-5.20 (m, 2.69H), 4.50-4.46 (m, 2.88H), 4.24-3.36 (m, 20.2H), 3.32-3.19 (m, 6.6H), 2.84-2.52 (m, 13.0H), 2.24-2.10 (m, 11.9H)

(2) Second Step 10 g of the product obtained in the first step, 54 mg of $PtO_2$, 2.32 g of triethoxysilane and 150 ml of toluene were added to a flask, followed by stirring at room temperature for 5 minutes. The temperature thereof was set at 80° C., and heating while stirring was conducted for 24 hours. After completing the reaction, the reaction mixture was cooled to room temperature, and an inorganic material was removed using a celite filter. Toluene was removed through evaporation and completely dried using a vacuum pump to produce a novolac epoxy compound having an ethoxysilyl group having the concentration ratio of epoxy:silyl function groups of 2.0:1. The NMR data of the novolac epoxy compound having the ethoxysilyl group thus obtained are as follows.

$^1$H NMR (400 MHz, DMSO): δ=7.02-6.89 (m, 10H), 4.24-3.36 (m, 28.7H), 3.34-3.19 (m, 10.6H), 2.84-2.52 (m, 13.7H), 2.24-2.10 (m, 12.1H), 1.83-1.70 (m, 2.4H), 1.24-1.20 (m, 11.6H), 0.80-0.61 (m, 2.4H)

The reaction scheme of the above Synthetic Example 7 is as follows.

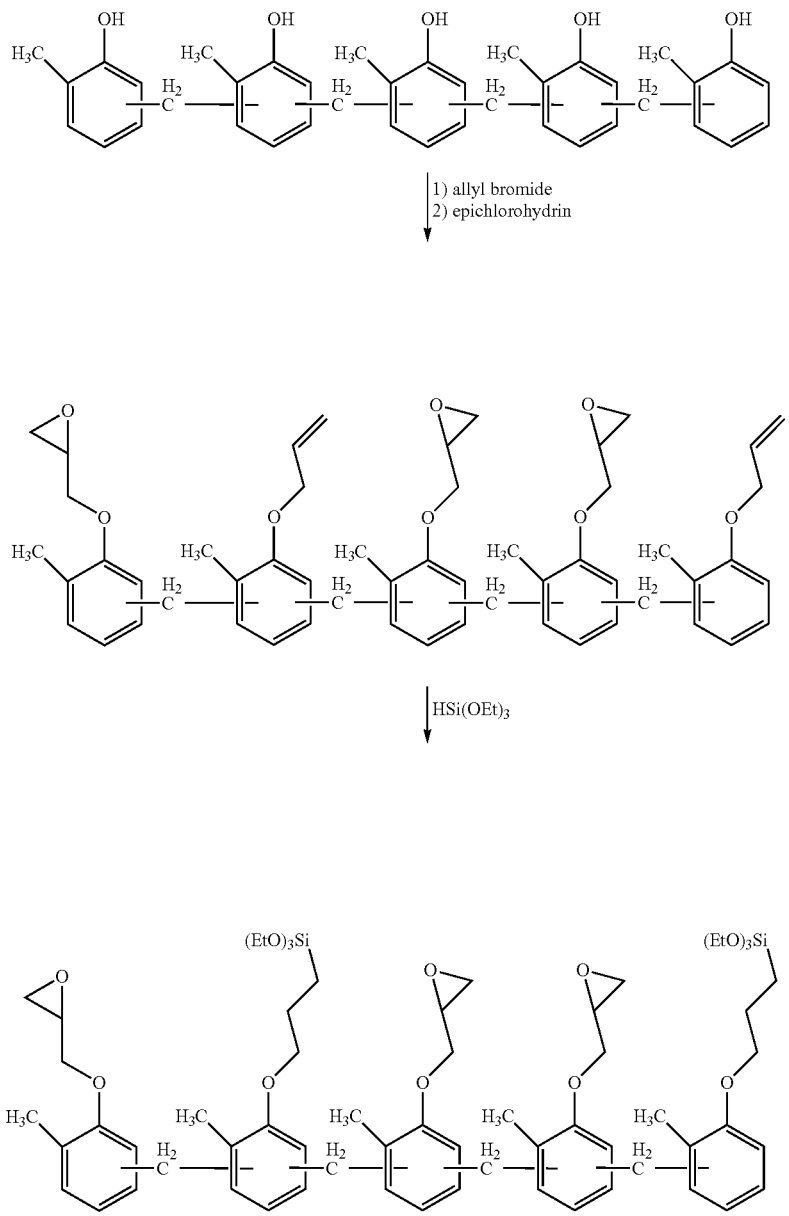

Synthetic Example 8

(1) First Step

In a two-necked flask, 10 g of a cresol novolac resin (Nippon kayaku Co., trade name EOCN-1020-55) and 1.43 g of NaOH in 250 ml of DMSO were stirred at room temperature for 30 minutes. Then, the temperature thereof was lowered to 0° C., and 18.88 g of epichlorohydrin was slowly added, followed by stirring at room temperature for 24 hours. After completing the reaction, the reaction mixture was worked-up using 400 ml of ethyl acetate and a saturated NaCl solution. An organic layer was separated and remaining $H_2O$ was removed with $MgSO_4$. The solvent was evaporated and dried using a vacuum pump to produce an intermediate. The NMR analysis result of the intermediate thus obtained is as follows.

$^1$H NMR (400 MHz, DMSO): δ=7.02-6.89 (m, 10H), 4.25-3.36 (m, 23.2H), 3.32-3.19 (m, 7.6H), 2.84-2.52 (m, 13.7H), 2.24-2.10 (m, 12.8H)

(2) Second Step 10 g of the intermediate obtained in the first step, 3.33 g of diisopropylethylamine and 200 ml of methylene chloride were added to a flask and stirred at room temperature. Then, 3.82 g of 3-(triethoxysilyl)propyl isocyanate was added thereto at room temperature, followed by reacting while heating to 60° C. for 12 hours. After completing the reaction, the reaction mixture was worked-up using a saturated $NH_4Cl$ solution. An organic layer was separated, and remaining $H_2O$ was removed with $MgSO_4$. The organic layer was filtered using a celite filter and evaporated to produce a final product having the concentration ratio of epoxy:silyl function groups of 2.0:1. The NMR data of the novolac epoxy compound having an ethoxysilyl group thus obtained are as follows.

$^1$H NMR (400 MHz, DMSO): δ=7.03-6.88 (m, 10H), 5.26-5.21 (br s, 1.30H), 4.25-3.19 (m, 44.4H), 2.84-2.52 (m, 13.7H), 2.24-2.10 (m, 12.8H), 1.77-1.66 (m, 2.7H), 1.26-1.21 (m, 11.9H), 0.72-0.64 (m, 2.7H)

The reaction scheme of the above Synthetic Example 8 is as follows.

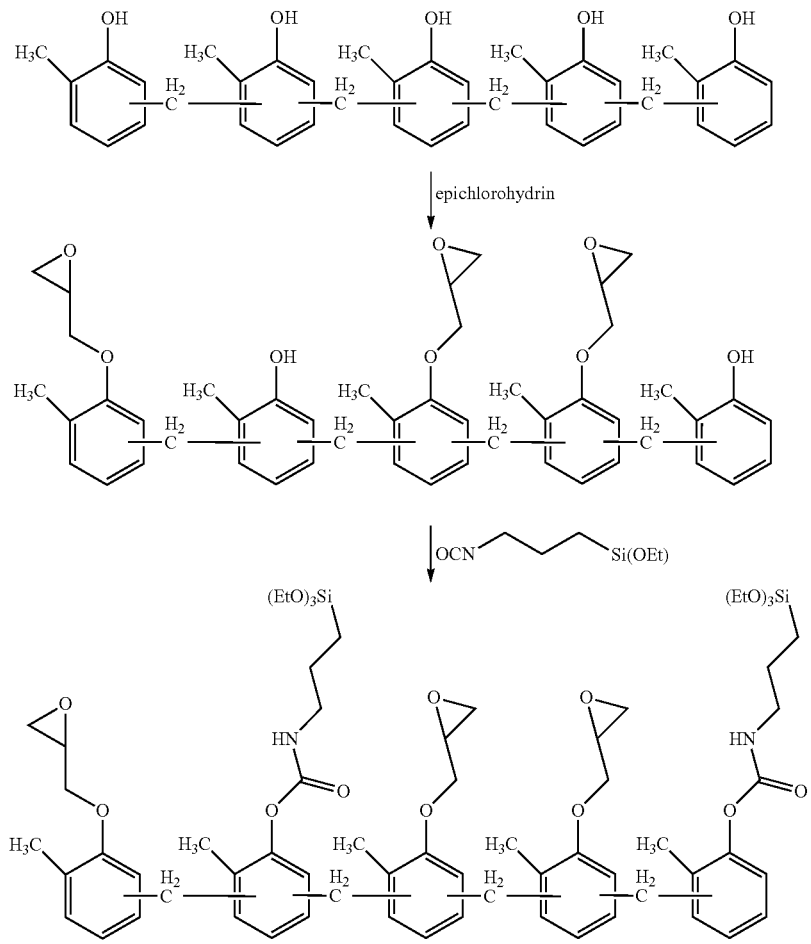

Synthetic Example 9

(1) First Step

In a two-necked flask, 10 g of a bisphenol A novolac resin (DIC Corporation) and 8.47 g of NaOH in 250 ml of DMSO were stirred at room temperature for 30 minutes. Then, the temperature thereof was lowered to 0° C., and 3.08 g of allyl bromide was slowly added thereto, followed by stirring at room temperature for 1 hour. Then, the temperature thereof was lowered to 0° C. again, and 31.36 g of epichlorohydrin was slowly added, followed by stirring at room temperature for 24 hours. After completing the reaction, the reaction mixture was worked-up using 400 ml of ethyl acetate and a saturated NaCl solution. An organic layer was separated and remaining $H_2O$ was removed with $MgSO_4$. The solvent was evaporated and dried using a vacuum pump to produce an intermediate. The NMR analysis result of the intermediate thus obtained is as follows.

$^1$H NMR (400 MHz, DMSO): δ=7.31-7.26 (m, 12H), 6.72-6.65 (m, 20H), 6.06-6.15 (m, 3.22H), 5.42-5.22 (m, 6.58H), 4.51-4.47 (m, 6.92H), 4.18-3.79 (m, 25.55H), 3.33-3.28 (m, 8.01H), 2.77-2.58 (m, 14.65H), 1.62 (m, 32.9H)

(2) Second Step 10 g of the product obtained in the first step, 89 mg of $PtO_2$, 3.86 g of triethoxysilane and 150 ml of toluene were added to a flask and stirred at room temperature for 5 minutes. Then, the temperature thereof was set at 80° C., and the reaction mixture was heated while stirring for 24 hours. After completing the reaction, the reaction mixture was cooled to room temperature, and an inorganic material was removed using a celite filter. The toluene was removed through evaporation, and the product was completely dried using a vacuum pump to produce a novolac epoxy compound having an ethoxysilyl group having the concentration ratio of epoxy:silyl function groups of 2.3:1. The NMR data of the novolac epoxy compound having an ethoxysilyl group thus obtained are as follows.

$^1$H NMR (400 MHz, DMSO): δ=7.32-7.24 (m, 12H), 6.75-6.65 (m, 20H), 4.22-3.79 (m, 45.65H), 3.36-3.28 (m, 15.01H), 2.77-2.58 (m, 14.65H), 1.83-1.69 (m, 6.35H), 1.62 (m, 32.9H), 1.27-1.20 (m, 29.9H), 0.83-0.62 (m, 6.42H)

The reaction scheme of the above Synthetic Example 9 is as follows.

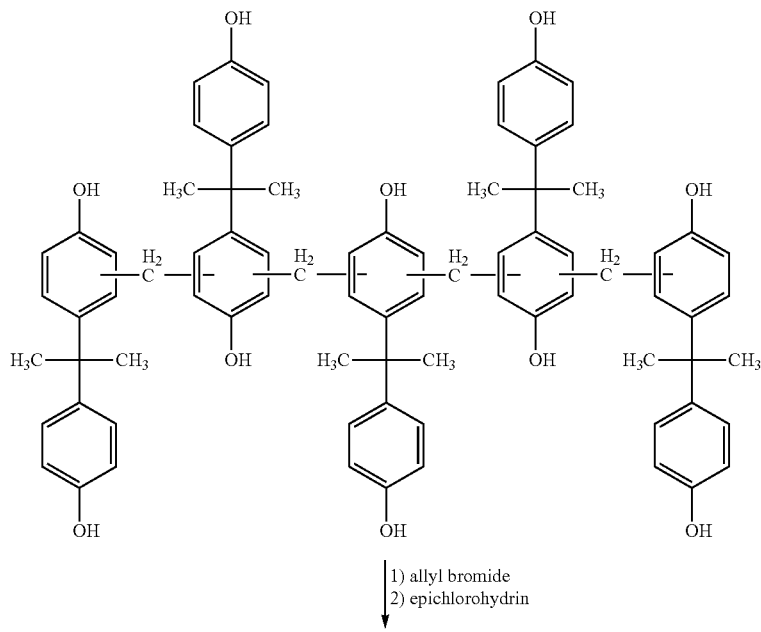

-continued

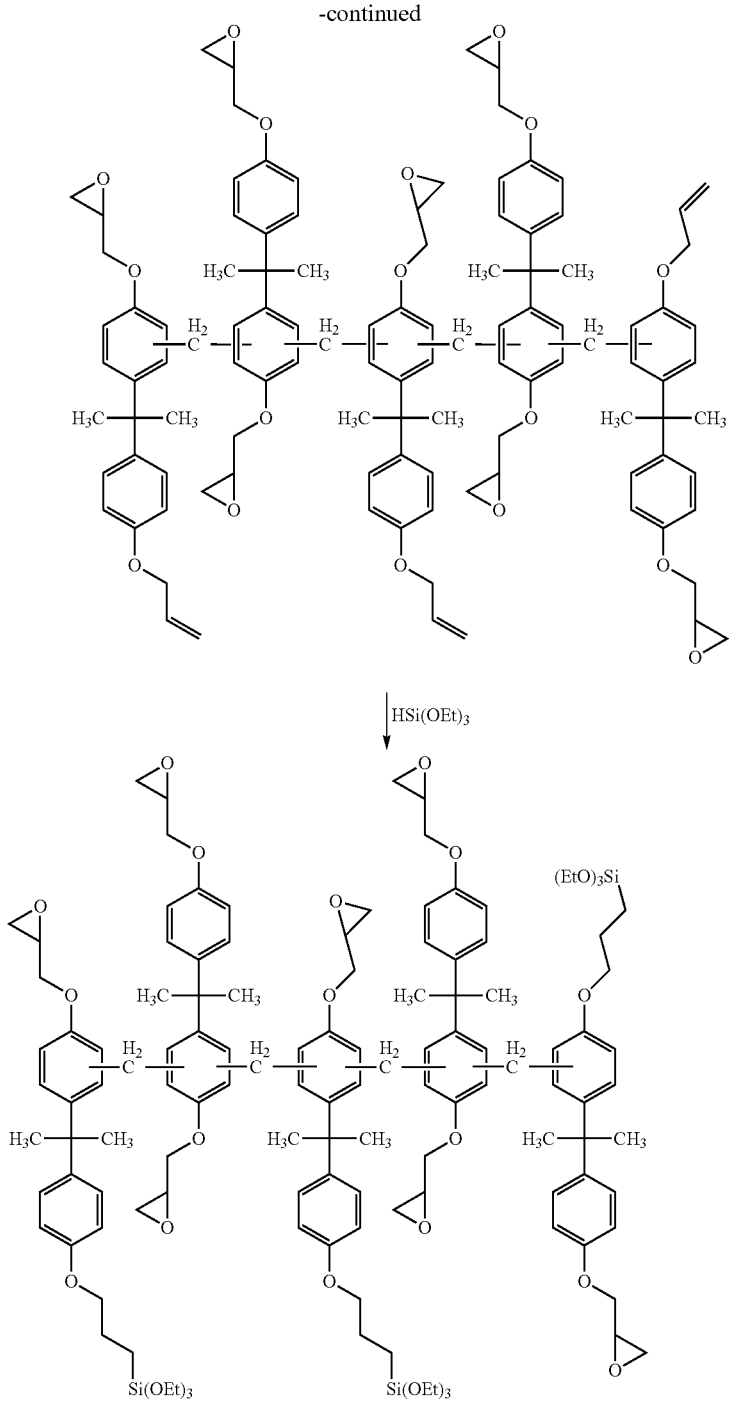

Synthetic Example 10

(1) First Step

In a two-necked flask, 10 g of a bisphenol A novolac resin (DIC Corporation) and 2.37 g of NaOH in 250 ml of DMSO were stirred at room temperature for 30 minutes. Then, the temperature thereof was lowered to 0° C., and 31.36 g of epichlorohydrin was slowly added, followed by stirring at room temperature for 24 hours. After completing the reaction, the reaction mixture was worked-up using 400 ml of ethyl acetate and a saturated NaCl solution. An organic layer was separated and remaining H$_2$O was removed with MgSO$_4$. The solvent was evaporated and dried using a vacuum pump to produce an intermediate. The NMR analysis result of the intermediate thus obtained is as follows.

$^1$H NMR (400 MHz, DMSO): δ=7.31-7.26 (m, 12H), 6.72-6.65 (m, 20H), 4.18-3.79 (m, 29.55H), 3.33-3.28 (m, 8.31H), 2.77-2.58 (m, 16.65H), 1.62 (m, 35.9H)

(2) Second Step 10 g of the intermediate obtained in the first step, 5.06 g of diisopropylethylamine and 200 ml of methylene chloride were added to a flask and stirred at room temperature. Then, 5.81 g of 3-(triethoxysilyl)propyl isocyanate was added thereto at room temperature, followed by reacting while heating to 60° C. for 12 hours. After completing the reaction, the reaction mixture was cooled to room temperature and worked-up using a saturated NH₄Cl solution. An organic layer was separated, and remaining H₂O was removed with MgSO₄. The organic layer was filtered using a celite filter and evaporated to produce a final product having the concentration ratio of epoxy:silyl function groups of 2.8:1.

¹H NMR (400 MHz, DMSO): δ=7.31-7.26 (m, 12H), 6.72-6.65 (m, 20H), 5.33-5.25 (m, 2.95H), 4.23-3.70 (m, 50.01H), 3.33-3.25 (m, 16.09H), 2.77-2.58 (m, 16.65H), 1.77-1.66 (m, 6.83H), 1.62 (m, 35.9H), 1.27-1.22 (m, 29.9H), 0.75-0.66 (m, 7.01H)

The reaction scheme of the above Synthetic Example 10 is as follows.

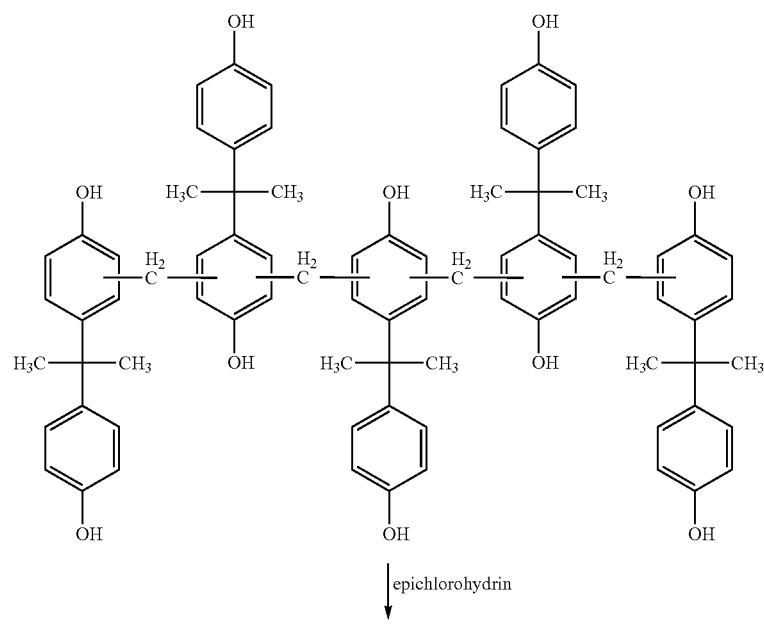

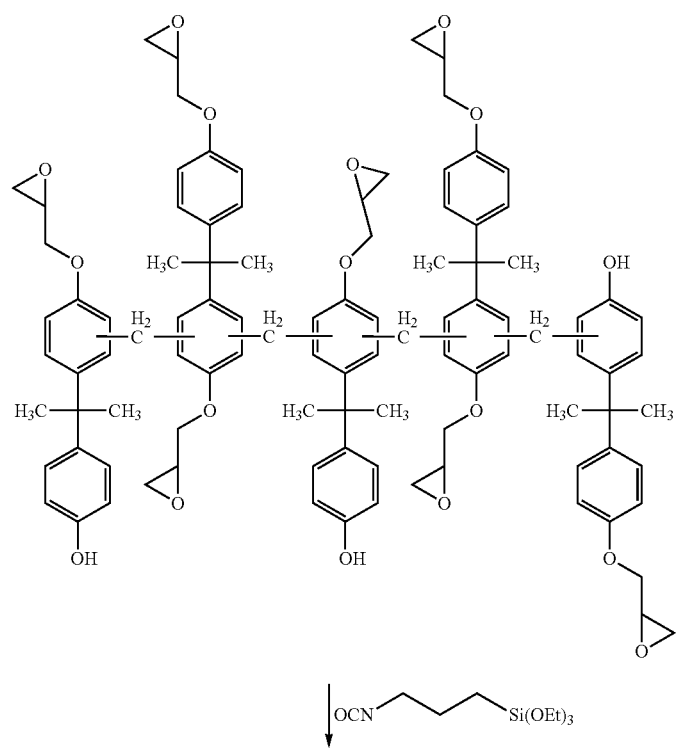

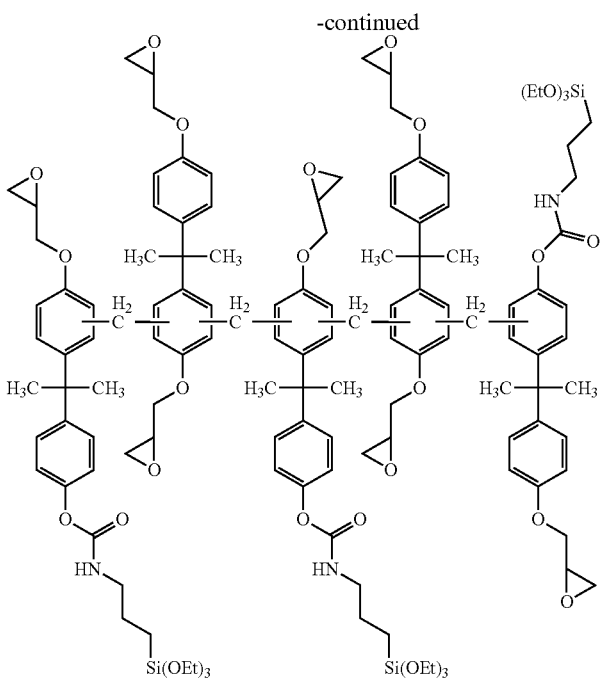

Synthetic Example 11

(1) First Step

In a two-necked flask, 10 g of a naphthalene novolac resin (Nippon kayaku Co., trade name KAYAHARD CBN) and 7.25 g of NaOH in 250 ml of DMSO were stirred at room temperature for 30 minutes. Then, the temperature thereof was lowered to 0° C., and 2.63 g of allyl bromide was slowly added thereto, followed by stirring at room temperature for 1 hour. Then, the temperature thereof was lowered to 0° C. again, and 26.82 g of epichlorohydrin was slowly added, followed by stirring at room temperature for 24 hours. After completing the reaction, the reaction mixture was worked-up using 400 ml of ethyl acetate and a saturated NaCl solution. An organic layer was separated and remaining $H_2O$ was removed with $MgSO_4$. The solvent was evaporated and dried using a vacuum pump to produce an intermediate. The NMR analysis result of the intermediate thus obtained is as follows.

$^1$H NMR (400 MHz, DMSO): δ=8.03-8.02 (m, 1.27H), 7.88-7.51 (m, 9.99H), 7.39-7.02 (m, 10.43H), 6.59-6.54 (m, 4.41H), 6.05-6.01 (m, 2.1H), 5.40-5.20 (m, 4.5H), 4.50-4.46 (m, 4.4H), 4.42H (s, 3.84H), 4.18-3.80 (m, 11.4H), 3.32-3.28 (m, 4.3H), 2.74-2.59 (m, 9.8H)

(2) Second Step 10 g of the product obtained in the first step, 76 mg of $PtO_2$, 3.30 g of triethoxysilane and 150 ml of toluene were added to a flask and stirred at room temperature for 5 minutes. Then, the temperature thereof was set at 80° C., and the reaction mixture was heated while stirring for 24 hours. After completing the reaction, the reaction mixture was cooled to room temperature, and an inorganic material was removed using a celite filter. The toluene was removed through evaporation, and the product was completely dried using a vacuum pump to produce a novolac epoxy compound having an ethoxysilyl group. The NMR data of the novolac epoxy compound having an ethoxysilyl group thus obtained are as follows.

$^1$H NMR (400 MHz, DMSO): δ=8.03-8.02 (m, 1.27H), 7.88-7.51 (m, 9.99H), 7.39-7.02 (m, 10.43H), 6.59-6.54 (m, 4.41H), 4.42H (s, 3.84H), 4.21-3.80 (m, 18.4H), 3.35-3.25 (m, 7.2H), 2.74-2.59 (m, 9.8H), 1.83-1.69 (m, 2.2H), 1.25-1.21 (m, 10.1H), 0.80-0.61 (m, 2.1H)

The reaction scheme of the above Synthetic Example 11 is as follows.

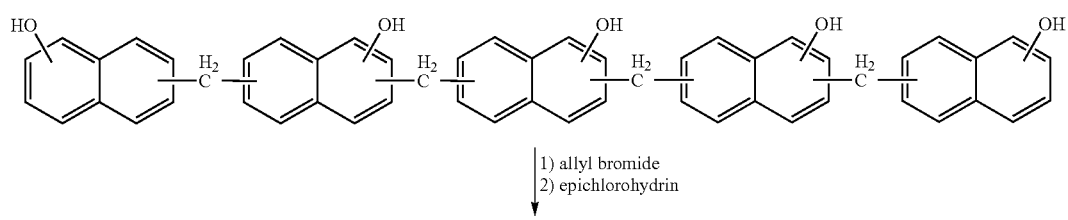

-continued

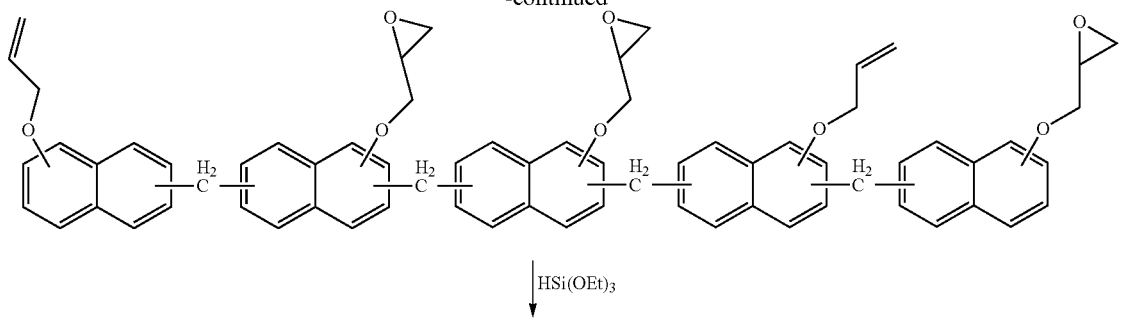

HSi(OEt)₃

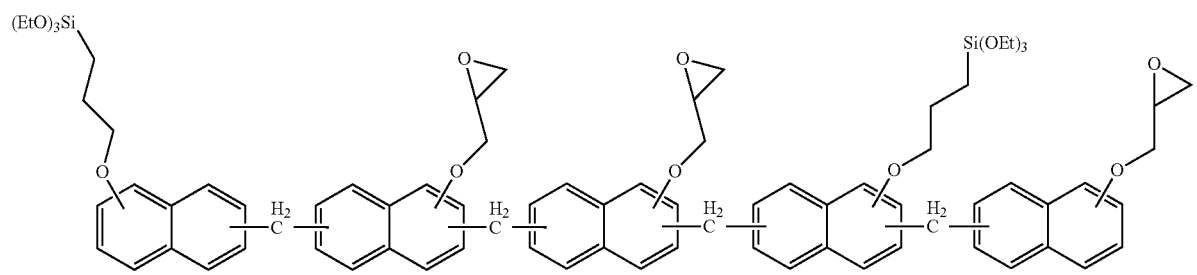

Synthetic Example 12

(1) First Step

In a two-necked flask, 10 g of a naphthalene novolac resin (Nippon kayaku Co., trade name KAYAHARD CBN) and 2.03 g of NaOH in 250 ml of DMSO were stirred at room temperature for 30 minutes. Then, the temperature thereof was lowered to 0° C., and 26.82 g of epichlorohydrin was slowly added, followed by stirring at room temperature for 24 hours. After completing the reaction, the reaction mixture was worked-up using 400 ml of ethyl acetate and a saturated NaCl solution. An organic layer was separated and remaining $H_2O$ was removed with $MgSO_4$. The solvent was evaporated and dried using a vacuum pump to produce an intermediate. The NMR analysis result of the intermediate thus obtained is as follows.

$^1$H NMR (400 MHz, DMSO): δ=8.03-8.02 (m, 1.28H), 7.88-7.51 (m, 9.89H), 7.39-7.02 (m, 10.53H), 6.59-6.54 (m, 4.45H), 4.42H (s, 3.96H), 4.19-3.80 (m, 12.7H), 3.32-3.26 (m, 5.3H), 2.74-2.59 (m, 10.9H)

(2) Second Step 10 g of the intermediate obtained in the first step, 4.73 g of diisopropylethylamine and 200 ml of methylene chloride were added to a flask and stirred at room temperature. Then, 5.43 g of 3-(triethoxysilyl) propyl isocyanate was added thereto at room temperature, and the reaction was carried out while heating to 60° C. for 12 hours. After completing the reaction, the reaction mixture was cooled to room temperature and worked-up using a saturated $NH_4Cl$ solution. An organic layer was separated, and remaining $H_2O$ was removed using $MgSO_4$. The product was filtered using a celite filter and evaporated to produce a final product.

$^1$H NMR (400 MHz, DMSO): δ=8.04-8.02 (m, 1.25H), 7.88-7.50 (m, 10.0H), 7.39-7.01 (m, 10.55H), 6.60-6.54 (m, 4.55H), 5.25-5.23 (br s, 2.3H), 4.42H (s, 3.96H), 4.21-3.80 (m, 26.6H), 3.40-3.26 (m, 9.2H), 1.77-1.65 (m, 4H), 2.74-2.59 (m, 10.8H), 1.26-1.22 (m, 20.1H), 0.73-0.63 (m, 4.2H)

The reaction scheme of the above Synthetic Example 12 is as follows.

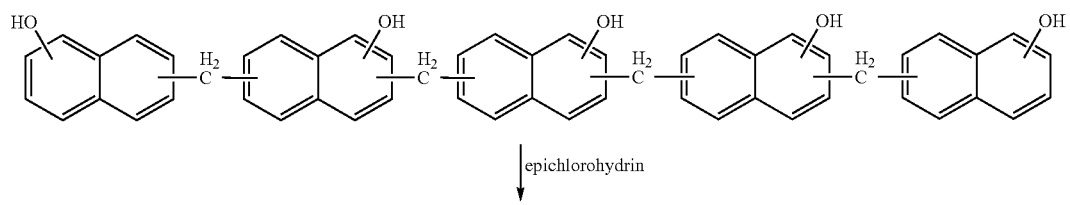

epichlorohydrin

-continued

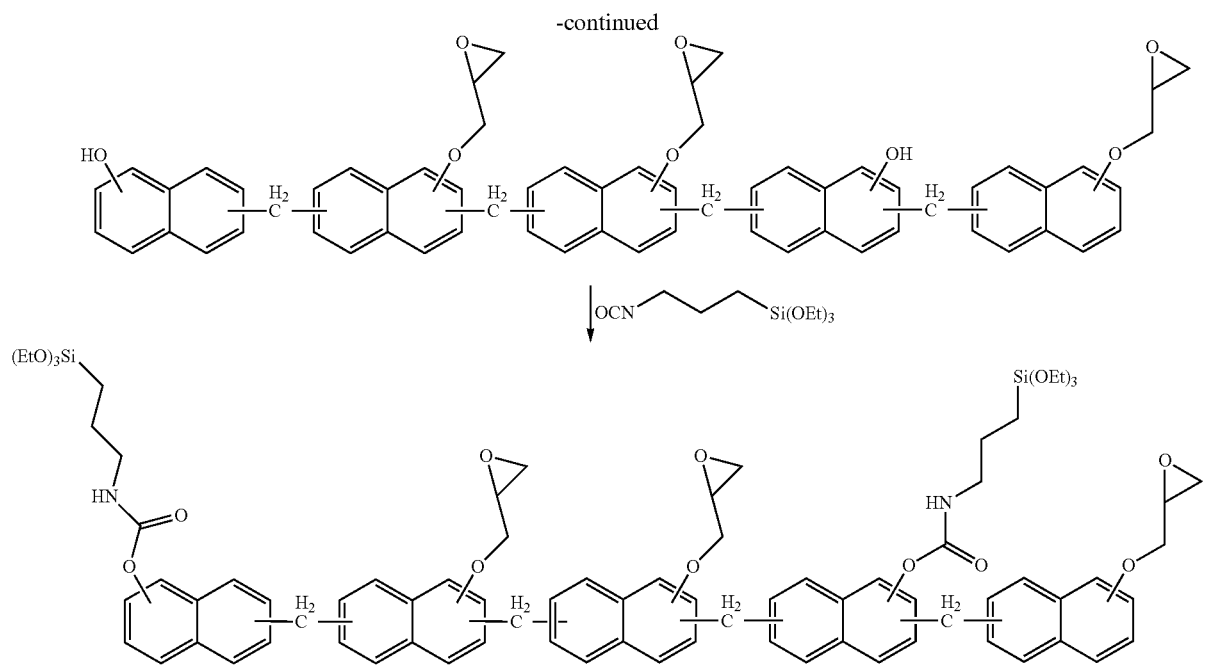

Evaluation of Physical Properties: Preparation of Cured Article and Evaluation of Heat Resistance 1. Preparation of Epoxy Composite (1) Preparation of Epoxy Glass Fiber Composite (Cured Article)

An epoxy compound (resin), a curing agent and a curing accelerator (a curing catalyst is added when a reaction catalyst is used) were dissolved in methyl ethyl ketone according to the formulation illustrated in Table 1 so that a solid content was 40 wt % and mixed to obtain a homogeneous solution. A glass fiber (a glass fiber texture of Nittobo Co, E-glass 2116) was impregnated with the mixture thus obtained to prepare a glass fiber composite including an epoxy compound. Then, the composite was placed in a vacuum oven heated to 100° C. to remove solvents, and was cured in a preheated hot press at 120° C. for 2 hours, at 180° C. for 2 hours and >200° C. for 2 hours to prepare a glass fiber composite film (4 mm×16 mm×0.1 mm). While manufacturing the composite film, the resin content of the composite film was controlled according to the pressure of a press and the viscosity of the resin. The resin content in the composite film is illustrated in the following Table 1.

In addition, when a composition for a glass fiber composite includes silica, an epoxy compound, and a silica slurry (70 wt % of solid content, 2-methoxyethanol solvent, 1 μm of silica average size) were dissolved in methyl ethyl ketone according to the formulation illustrated in the following Table 1 so that a solid content was 40 wt %. The mixture thus obtained was mixed in a rate of 1,500 rpm for 1 hour, and a curing agent was added, followed by further mixing for 50 minutes. Finally, a curing accelerator was added and mixed for 10 minutes further to obtain an epoxy mixture. A glass fiber composite was prepared by immersing a glass fiber (glass fiber fabric by Nittobo Co., E-glass 2116 or T-glass 2116) with the epoxy mixture. Then, the same curing process was performed under the same conditions as described above to prepare a composite film.

(2) Preparation of Epoxy Filler Composite (Cured Article)

All compounds except for the curing agent and the curing accelerator, and a silica slurry (70 wt % of solid content, 2-methoxyethanol solvent, 1 μm of silica average size) were dissolved in methyl ethyl ketone according to the formulation illustrated in the following Table 2 so that a solid content was 40 wt %. The mixture thus obtained was mixed in a rate of 1,500 rpm for 1 hour, and a curing agent was added, followed by further mixing for 50 minutes. Finally, a curing catalyst was added and mixed for 10 minutes to obtain an epoxy mixture. Then, the mixture was placed into a heated vacuum oven to 100° C. to remove solvents, and was cured in a hot press preheated to 120° C., at 120° C. for 2 hours, at 180° C. for 2 hours and at >200° C. for 2 hours to prepare an epoxy filler (inorganic particles) composite (5 mm×5 mm×3 mm).

2. Evaluation of Physical Properties

The dimensional changes with respect to the temperature of the cured articles according to the examples and comparative examples illustrated in the following Tables 1 and 2 were evaluated by using a Thermo-mechanical analyzer and are illustrated in the following Tables 1 and 2. The specimens of the epoxy glass fiber composite films were manufactured into a size of 4×16×0.1 (mm$^3$), and the specimens of the filler composites were manufactured into a size of 5×5×3 (mm$^3$).

TABLE 1

| | | | | | | | | | | | | |
|---|---|---|---|---|---|---|---|---|---|---|---|---|
| | | Epoxy compound (Synthetic Example No.) | Example 1 | Example 2 | Example 3 | Example 4 | Example 5 | Example 6 | Example 7 | Example 8 | Example 9 |
| Epoxy formulation (g) | Epoxy | 1 | 5.00 | | | | | | | | |
| | | 2 | | 5.00 | | | | | | | |
| | | 3 | | | 5.00 | 5.00 | 5.00 | 4.50 | 4.50 | 5.00 | 5.00 |
| | | 4 | | | | | | | | | |
| | | 5 | | | | | | | | | |
| | | 6 | | | | | | | | | |
| | | 7 | | | | | | | | | |
| | | 8 | | | | | | | | | |
| | | 9 | | | | | | | | | |
| | | 10 | | | | | | | | | |
| | | 11 | | | | | | | | | |
| | | 12 | | | | | | | | | |
| | | YX-4000H[1] | | | | | | | | | |
| | | DGEBA[2] | | | | | | 0.50 | 0.50 | | |
| | | Polydis[3] | | | | | | | | | |
| | | EOCN[4] | | | | | | | | | |
| | HF-IM[5] | | 2.19 | 1.97 | 1.13 | 1.13 | 1.13 | 1.30 | 1.30 | 1.30 | |
| | TPP[6] | | 0.03 | 0.04 | 0.04 | 0.04 | 0.04 | 0.03 | 0.03 | 0.03 | |
| | Tin-OC[7] | | | | | | | | | 0.25 | 0.25 |
| | Polyvinyl butyral | | | | | | | | | | |
| | Silica | | | | | 1.54 | 1.54 | | 1.54 | | |
| | Glass fiber type | | E | E | E | E | T | E | E | E | E |
| | Resin amount (wt %) | | 44% | 43% | 41% | 41% | 42 | 38% | 40% | 41% | 37% |
| Thermal properties | CTE (ppm/° C.) | $\alpha_1$ (T < Tg) | 8.6 | 6.9 | 6.5 | 6.2 | 3.0 | 8.5 | 8.0 | 7.5 | 7.6 |
| | Tg (° C.) | | TgL | TgL | TgL | TgL | TgL | TgL | TgL | TgL | TgL |

| | | | | | | | | | | | | |
|---|---|---|---|---|---|---|---|---|---|---|---|---|
| | | Epoxy compound (Synthetic Example No.) | Example 10 | Example 11 | Example 12 | Example 13 | Example 14 | Example 15 | Example 16 | Example 17 | Example 18 | Comparative Example 1 |
| Epoxy formulation (g) | Epoxy | 1 | | | | | | | | | | |
| | | 2 | | | | | | | | | | |
| | | 3 | | | | | | | | | | |
| | | 4 | 5.00 | | | | | | | | | |
| | | 5 | | 5.00 | | | | | | | | |
| | | 6 | | | 5.00 | | | | | | | |
| | | 7 | | | | 5.00 | | | | | | |
| | | 8 | | | | | 5.00 | | | | | |
| | | 9 | | | | | | 5.00 | | | | |
| | | 10 | | | | | | | 5.00 | | | |
| | | 11 | | | | | | | | 5.00 | | |
| | | 12 | | | | | | | | | 5.00 | |
| | | YX-4000H[1] | | | | | | | | | | |
| | | DGEBA[2] | | | | | | | | | | |
| | | Polydis[3] | | | | | | | | | | |
| | | EOCN[4] | | | | | | | | | | 5.00 |
| | HF-IM[5] | | 1.57 | 1.32 | 1.26 | 1.18 | 1.13 | 1.47 | 1.75 | 1.69 | 1.50 | 2.34 |
| | TPP[6] | | 0.04 | 0.03 | 0.03 | 0.03 | 0.03 | 0.03 | 0.03 | 0.03 | 0.03 | 0.03 |
| | Tin-OC[7] | | | | | | | | | | | |
| | Polyvinyl butyral | | | | | | | | | | | |
| | Silica | | | | | | | | | | | |
| | Glass fiber type | | E | E | E | E | E | E | E | E | E | E |
| | Resin amount (wt %) | | 40% | 40% | 38% | 39% | 39% | 38% | 40% | 39% | 40% | 40% |
| Thermal properties | CTE (ppm/° C.) | $\alpha_1$ (T < Tg) | 6.8 | 7.5 | 7.2 | 8.1 | 7.8 | 8.2 | 8.0 | 7.3 | 6.9 | 15 |
| | Tg (° C.) | | TgL | TgL | TgL | TgL | TgL | TgL | TgL | TgL | TgL | 150 |

TABLE 2

| | | Filler composite | | | | | | | | | |
|---|---|---|---|---|---|---|---|---|---|---|---|
| No. | | Epoxy compound (Synthetic Example No.) | Example 19 | Example 20 | Example 21 | Example 22 | Example 23 | Example 24 | Example 25 | Example 26 | Example 27 |
| Epoxy formulation (g) | Epoxy | 1 | 4.00 | | | | | | | | |
| | | 2 | | 4.00 | | | | | | | |
| | | 3 | | | 4.00 | | | | | | |
| | | 4 | | | | 4.00 | | | | | |
| | | 5 | | | | | 4.00 | | | | |
| | | 6 | | | | | | 4.00 | | | |
| | | 7 | | | | | | | 4.00 | | |
| | | 8 | | | | | | | | 4.00 | |
| | | 9 | | | | | | | | | 3.60 |
| | | 10 | | | | | | | | | |
| | | 11 | | | | | | | | | |
| | | 12 | | | | | | | | | |
| | | YX-4000H[(1)] | | | | | | | | | 0.40 |
| | | DGEBA[(2)] | | | | | | | | | |
| | | Polydis[(3)] | | 0.49 | 0.49 | 0.49 | 0.49 | 0.49 | 0.49 | 0.49 | 0.49 |
| | | EOCN[(4)] | | | | | | | | | |
| | HF-1M[(5)] | | 1.88 | 1.71 | 1.33 | 1.39 | 1.19 | 1.14 | 1.08 | 1.03 | 1.58 |
| | TPP[(6)] | | 0.02 | 0.02 | 0.03 | 0.03 | 0.02 | 0.02 | 0.02 | 0.02 | 0.02 |
| | Tin-OC[(7)] | | | | | | | | | | |
| | Polyvinyl butyral | | | 0.99 | 0.99 | 0.99 | 0.99 | 0.99 | 0.99 | 0.99 | 0.99 |
| | Silica | | 23.72 | 29.54 | 26.18 | 27.59 | 26.78 | 26.57 | 26.31 | 26.14 | 28.31 |
| | Filler amount (wt %) | | 80 | 80 | 80 | 80 | 80 | 80 | 80 | 80 | 80 |
| Thermal properties | CTE (ppm/°C.) | $\alpha_1$ (T < Tg) | 7.9 | 7.0 | 6.2 | 5.5 | 6.8 | 6.4 | 7.9 | 7.6 | 7.1 |
| | Tg (°C.) | | TgL | TgL | TgL | TgL | TgL | TgL | TgL | TgL | TgL |

| No. | | Epoxy compound (Synthetic Example No.) | Example 28 | Example 29 | Example 30 | Comparative Example 2 |
|---|---|---|---|---|---|---|
| Epoxy formulation (g) | Epoxy | 1 | | | | |
| | | 2 | | | | |
| | | 3 | | | | |
| | | 4 | | | | |
| | | 5 | | | | |
| | | 6 | | | | |
| | | 7 | | | | |
| | | 8 | | | | |
| | | 9 | | | | |
| | | 10 | 3.60 | | | |
| | | 11 | | 3.60 | | |
| | | 12 | | | 3.60 | |
| | | YX-4000H[(1)] | 0.40 | 0.40 | 0.40 | |
| | | DGEBA[(2)] | | | | |
| | | Polydis[(3)] | 0.49 | 0.49 | 0.49 | |
| | | EOCN[(4)] | | | | 4.00 |
| | HF-1M[(5)] | | 1.62 | 1.57 | 1.44 | 1.98 |
| | TPP[(6)] | | 0.02 | 0.02 | 0.02 | 0.05 |
| | Tin-OC[(7)] | | | | | |
| | Polyvinyl butyral | | 0.99 | 0.99 | 0.99 | 0.99 |
| | Silica | | 28.47 | 28.28 | 27.75 | 27.96 |
| | Filler amount (wt %) | | 80 | 80 | 80 | 80 |
| Thermal properties | CTE (ppm/°C.) | $\alpha_1$ (T < Tg) | 6.9 | 6.1 | 6.8 | 17 |
| | Tg (°C.) | | TgL | TgL | TgL | 150 |

Note: Common epoxy compounds used in the above Tables 1 and 2 are as follows.
(1) YX-4000H: Biphenyl epoxy (Yuka Shell Epoxy Co.)
(2) DGEBA: Diglycidyl ether of bisphenol A (Aldrich Co.)
(3) POLYDIS® 3615: Rubber modified BGEBA epoxy resin (Strruktol Co.)
(4) EOCN: Epoxy resin of ortho-cresol novolac (Nippon Kayaku Co.)
(5) HF-1M: Phenol novolac curing agent (Meiwa Plastic Industries)
(6) TPP: Triphenyl phosphine (Aldrich Co.)
(7) tin-OC: Tin(II)-ethylhexanoate (Aldrich Co.)

As shown in the above Table 1, for the glass fiber composite of the novolac epoxy compound modified with the alkoxysilyl group of the present invention, thermal properties are largely improved, and a low CTE, high glass transition temperature or Tg-less property are exhibited.

Figure 2:
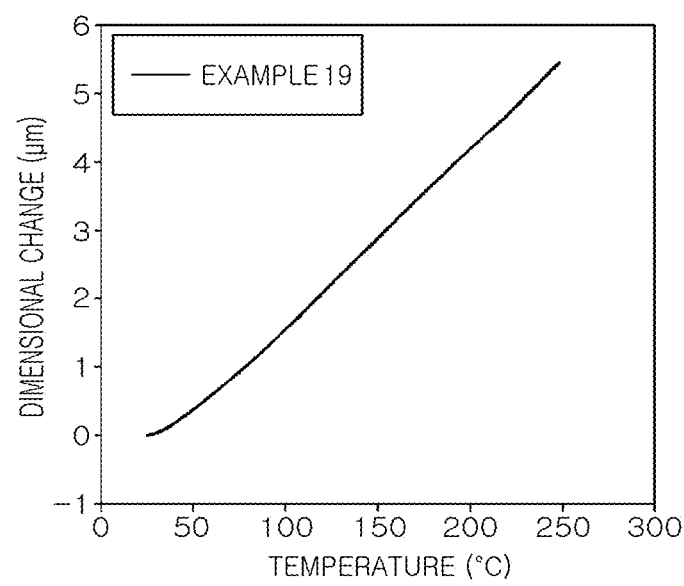
FIG. 2 is a graph illustrating dimensional change with the variation of the temperature of a composite according to Example 19.

Particularly, the CTE of the glass fiber composites of Examples 1 to 18 was low and 6.2 to 8.6 ppm/° C. when compared to the CTE=15 ppm/° C. (E-glass) of the novolac epoxy resin composite not including an alkoxysilyl group (Comparative Example 1), and Tg-less property were observed. In addition, the CTE of the inorganic particle composites of Examples 19 to 30 was 5.5 to 7.9 ppm/° C., and very excellent CTE and Tg-less property were observed. Particularly, as shown in FIGS. 1 and 2, the novolac epoxy composite modified with an alkoxysilyl group according to Examples 1 to 19 exhibited Tg-less properties.

The good properties of the CTE and the glass transition temperature of the epoxy compound having an alkoxysilyl group observed through the present invention are considered to be obtained due to the effective formation of interfacial bonding of the alkoxysilyl group with the glass fiber and/or the filler.

3. Evaluation of Flame Retardant Property

Figure 3:
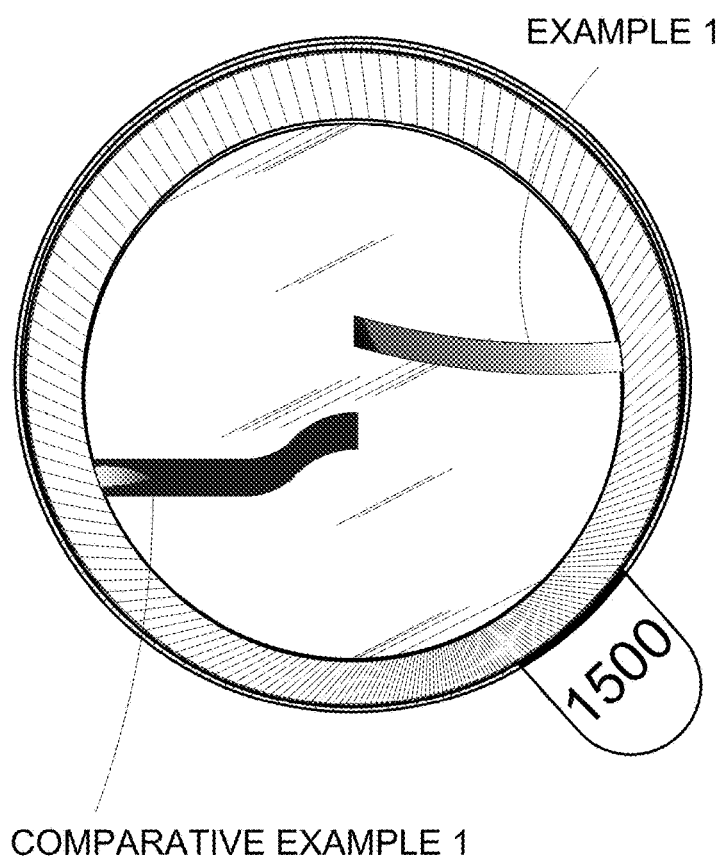
FIG. 3 is a photographic image illustrating the combustion state of the strips of the composites according to Example 1 and Comparative Example 1.

Strips of the composites according to Example 1 and Comparative Example 1 in the above Table 1 were ignited, and photographic images of the burned strips are illustrated in FIG. 3. As illustrated in FIG. 3, the strip of the composite of the epoxy compound according to Example 1 of the present invention was extinguished naturally within 1 to 2 seconds. However, the strip of the composite not including an alkoxysilyl group according to Comparative Example 1 was completely burned. Thus, it would be known that the alkoxysilylated epoxy compound according to the present invention has good flame retardant property.

While the present invention has been shown and described in connection with the exemplary embodiments, it will be apparent to those skilled in the art that modifications and variations can be made without departing from the spirit and scope of the invention as defined by the appended claims

The invention claimed is:

1. A novolac epoxy compound having at least one alkoxysilyl group selected from the group consisting of the following Formulae I-1 to I-4:

[Formula I-1]

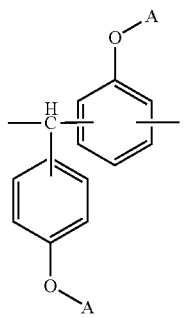

in the above Formula I-1, Z is one selected from the group consisting of the following Formulae 1A to 1F:

1A

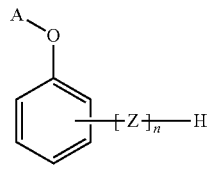

1B

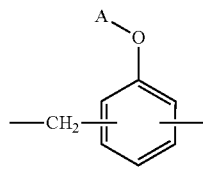

1C

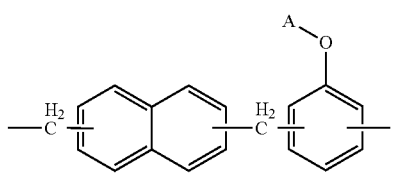

1D

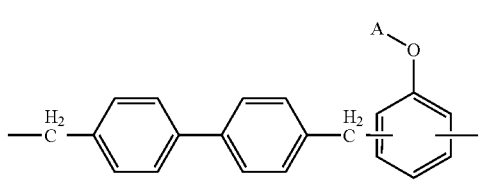

1E

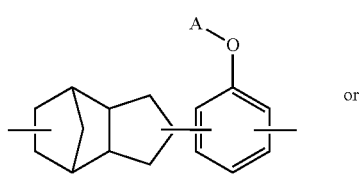

or

1F

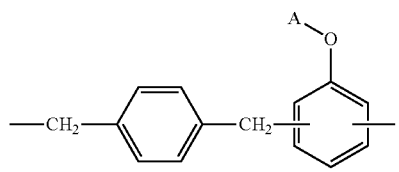

[I-2]

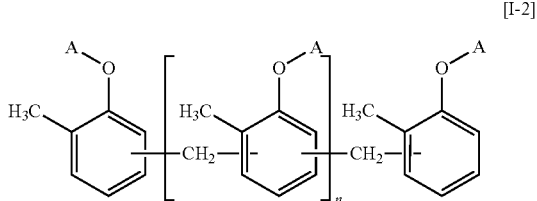

[I-3]

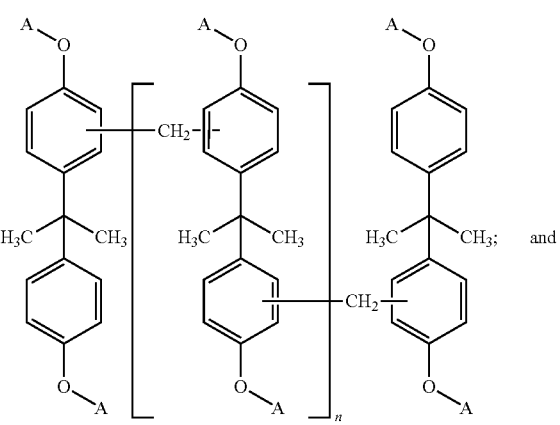

and

-continued

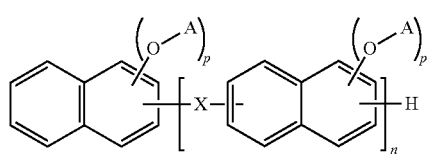
[I-4]

in the above Formula I-4, x is

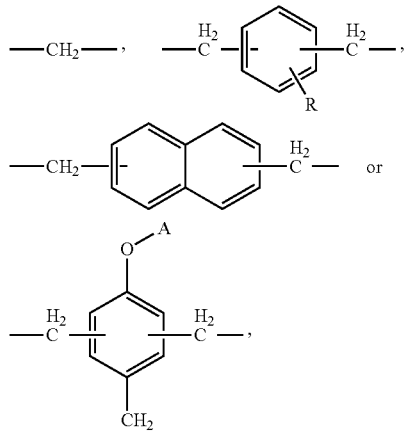

and in

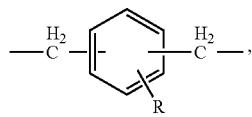

R is a linear or branched alkyl group of C1-C10, in the above Formulae I-1 to I-4, at least two of a plurality of A have a structure of the following Formula A2, and at least one of A has a structure of the following Formula A3, where in the case that at least one of A is A3, the remainder thereof have the following Formula B3 or hydrogen, in the above Formula I-1, in the case that Z is 1A to 1E, n is an integer of at least 2, and in the case that Z is 1F, n is an integer of at least 1, in the above Formulae I-2 and I-3, n is an integer of at least 1, in the above Formula I-4, in the case that x is

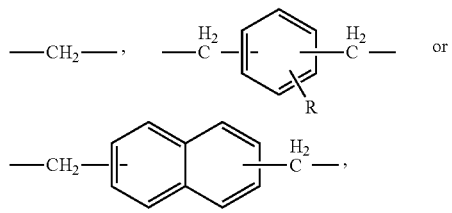

n is an integer of at least 2, and in the case that x is

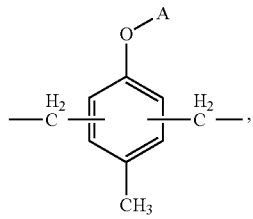

n is an integer of at least 1,
in the above Formula I-4, p is 1 or 2,

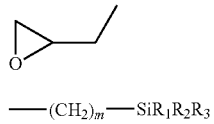
[Formula A2]

—(CH$_2$)$_m$—SiR$_1$R$_2$R$_3$    [Formula A3]

in the above Formulae A3, at least one of $R_1$ to $R_3$ is an alkoxy group having 1 to 5 carbon atoms, and the remainder thereof are an alkyl group having 1 to 10 carbon atoms, the alkoxy group and the alkyl group are a linear or a branched, and m is an integer from 3 to 10, —(CH$_2$)$_l$—CH═CH$_2$    [Formula B3]

in the above Formula B3, l is an integer from 1 to 8.

2. The novolac epoxy compound having at least one alkoxysilyl group of claim 1, wherein at least one of $R_1$ to $R_3$ in the above Formulae A3 is an ethoxy group.

3. A production method of a novolac epoxy compound having at least one alkoxysil group selected from the group consisting of Formulae I-1 to I-4, the production method comprising:

a first step of preparing one intermediate of the following Formulae IB-1 to IB-4 by reacting one starting material of the following Formulae IA-1 to IA-4, an alkenyl compound of the following Formula II and epichlorohydrin in the presence of a base and an optional solvent; and a second step of preparing one compound of Formulae I-1 to I 4 by reacting one intermediate of the above Formulae IB-1 to IB-4 and alkoxysilane of the following Formula IIIA in the presence of a platinum catalyst and an optional solvent:

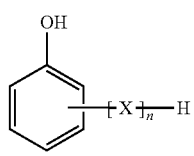
[Formula IA-1]

in the above Formula IA-1, X is one selected from the group consisting of the following Formulae 2A to 2F:

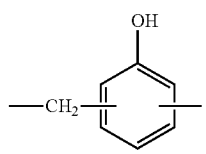
2A

2B
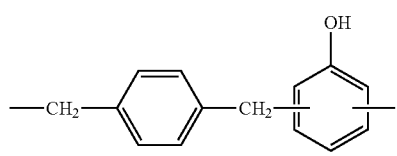
2C
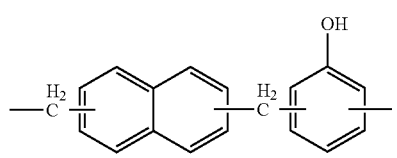
2D
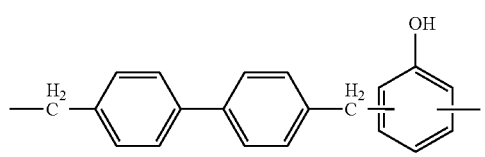
2E
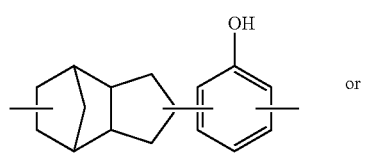  or
2F
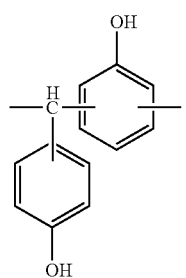
[Formula IA-2]
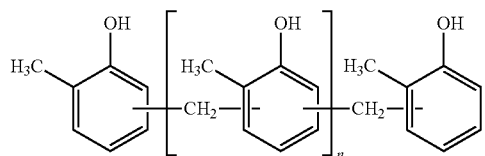
[Formula IA-3]
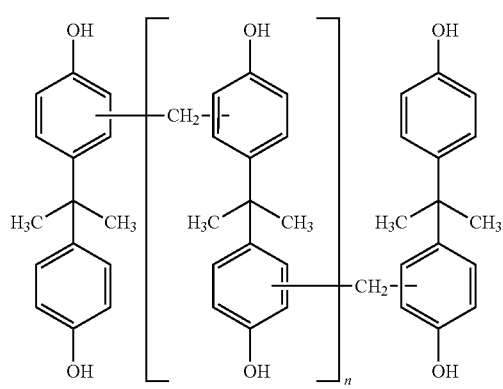
[Formula IA-4]
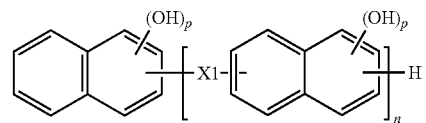
in the above Formula IA-4, x1 is
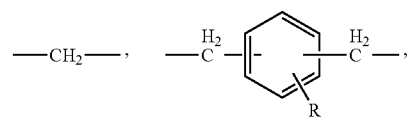
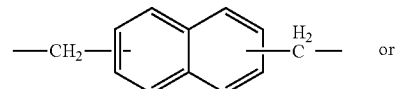  or
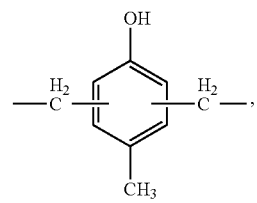
and in
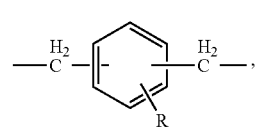
R is a linear or a branched alkyl group of C1-C10,
in the above Formula IA-1, in the case that X is 2A to 2E, n is an integer of at least 2, and in the case that X is 2F, n is an integer of at least 1,
in the above Formulae IA-2 and IA-3, n is an integer of at least 1,
in the above Formula IA-4, in the case that x1 is
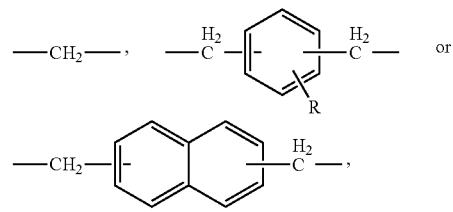

n is an integer of at least 2, and in the case that x1 is
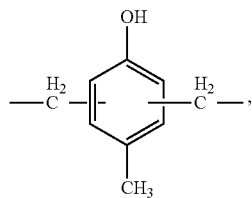
n is an integer of at least 1,
in the above Formula IA-4, p is 1 or 2,
[Formula IB-1]
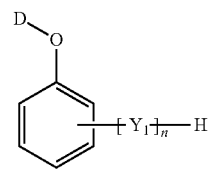
in the above Formula IB-1, $Y_1$ is one selected from the group consisting of the following Formulae 3A to 3F:
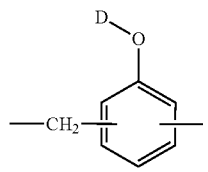
3A
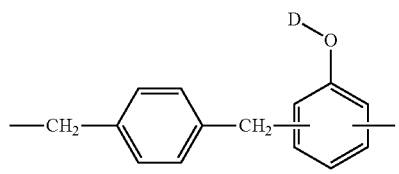
3B
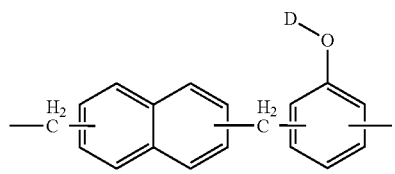
3C
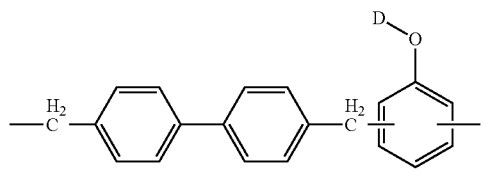
3D
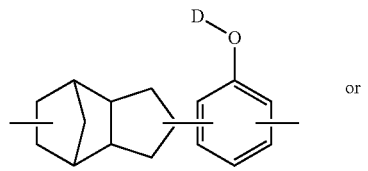
3E
or
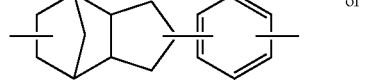
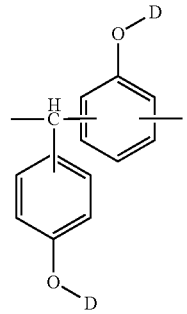
3F
[Formula IB-2]
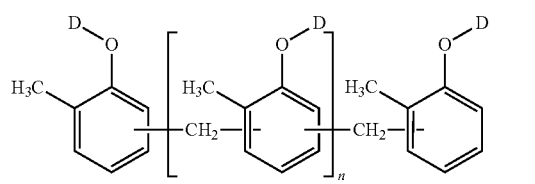
[Formula IB-3]
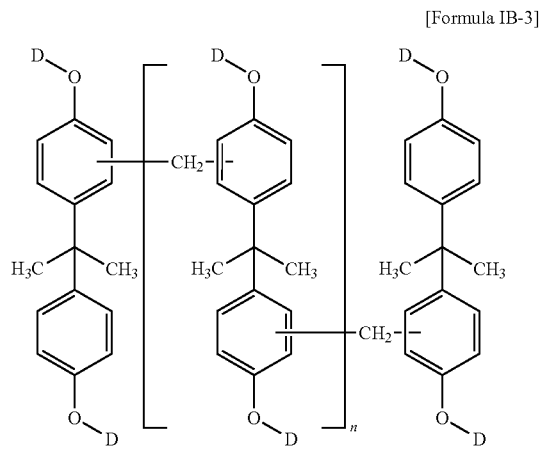
[Formula IB-4]
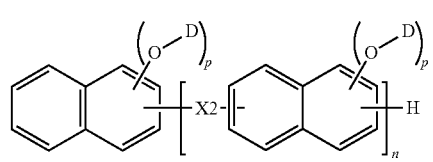
in the above Formula IB-4, x2 is
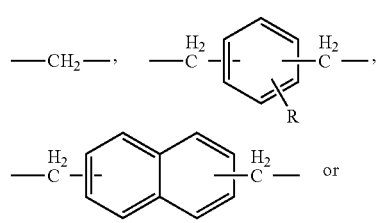
or -continued

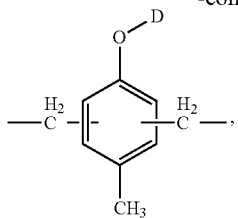

and in

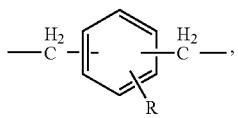

R is a linear or branched alkyl group of C1-C10,
in the above Formulae IB-1 to IB-4, at least two of a plurality of D are the following Formula B2, at least one of D is the following Formula B3, and the remainder thereof is hydrogen,
in the above Formula IB-1, in the case that Y1 is 3A to 3E, n is an integer of at least 2, and in the case that Y1 is 3F, n is an integer of at least 1,
in the above Formulae IB-2 and IB-3, n is an integer of at least 1,
in the above Formula IB-4, in the case that x2 is

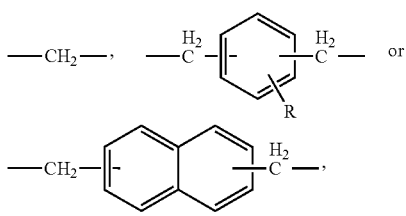

n is an integer of at least 2, and in the case that x2 is

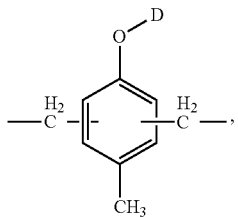

n is an integer of at least 1,
in the above Formula IB-4, p is 1 or 2,

[Formula B2]

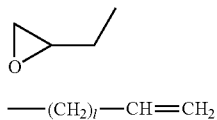

[Formula B3]

in the above Formula B3, l is an integer from 1 to 8, $$X-(CH_2)_l-CH=CH_2 \quad \text{[Formula II]}$$

in the above Formula II, l is an integer from 1 to 8, and X is a halide such as Cl, Br or I, $-O-SO_2-CH_3$, $-O-SO_2-CF_3$, or $-O-SO_2-C_6H_4-CH_3$, $$HSiR_aR_bR_c \quad \text{[Formula IIIA]}$$

in the above Formula IIIA, at least one of Ra to Rc is an alkoxy group of C1-C5, and the remainder thereof are an alkyl group of C1-C10, and the alkoxy group and the alkyl group is linear or a branched,

[Formula I-1]

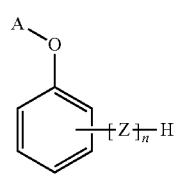

in the above Formula I-1, Z is one selected from the group consisting of the following Formulae 1A to 1F:

1A

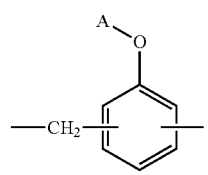

1B

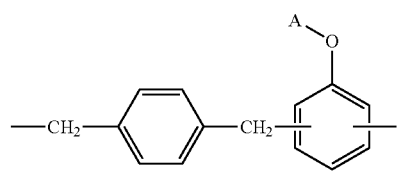

1C

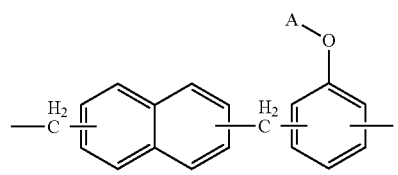

1D

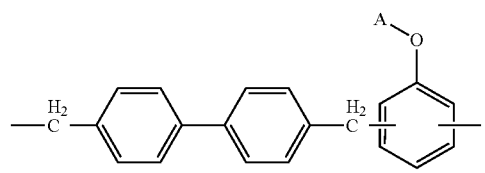

1E

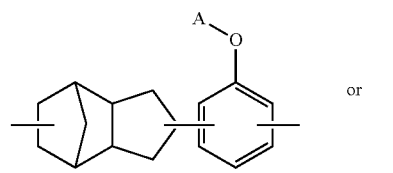

or

-continued

[I-2] 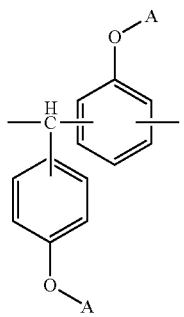

[I-3] 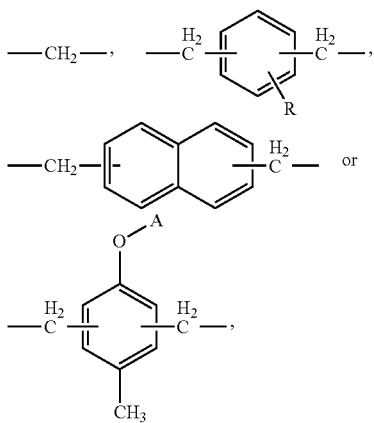

in the above Formula 1-4, x is

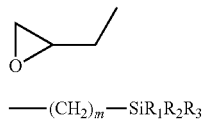

and in

1F 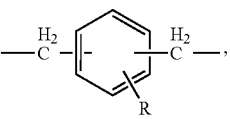

R is a linear or branched alkyl group of C1-C10, in the above Formulae I-1 to I-4, at least two of a plurality of A have a structure of the following Formula A2, and at least one of the plurality of A has the following Formula A3, and the remainder thereof have the following Formula B3 or hydrogen, in the above Formula I-1, in the case that Z is one of 1A to 1E, n is an integer of at least 2, and in the case that Z is 1F, n is an integer of at least 1, in the above Formulae I-2 and I-3, n is an integer of at least 1, in the above Formula I-4, in the case that x is

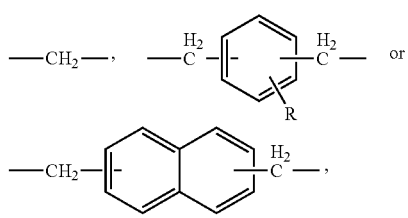

n is an integer of at least 2, and in the case that x is

[I-4] 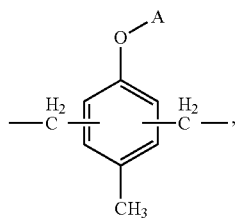

n is an integer of at least 1, in the above Formula I-4, p is 1 or 2,

[Formula A2]

[Formula A3]

—(CH$_2$)$_m$—SiR$_1$R$_2$R$_3$ in the above Formula A3, at least one of R$_1$ to R$_3$ is an alkoxy group having 1 to 5 carbon atoms, and the remainder thereof are an alkyl group having 1 to 10 carbon atoms, the alkoxy group and the alkyl group are a linear or a branched, and m is an integer from 3 to 10.

4. An epoxy composition comprising a novolac epoxy compound having at least one alkoxysil group selected from the group consisting of the following Formulae I-1 to I-4:

[Formula I-1]
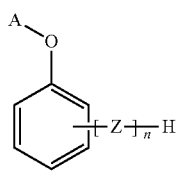
in the above Formula I-1, Z is one selected from the group consisting of the following Formulae 1A to 1F:
1A
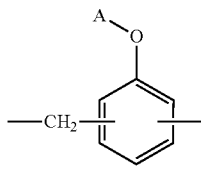
1B
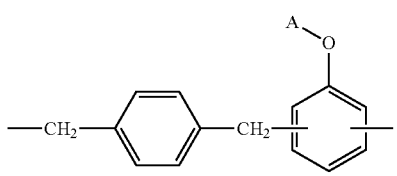
1C
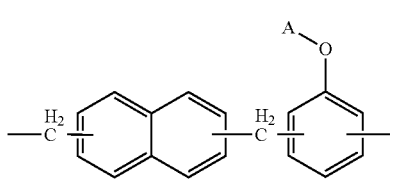
1D
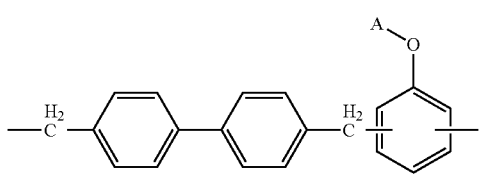
1E
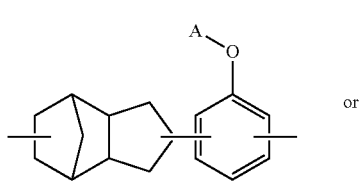
1F
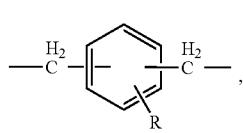
[I-2]
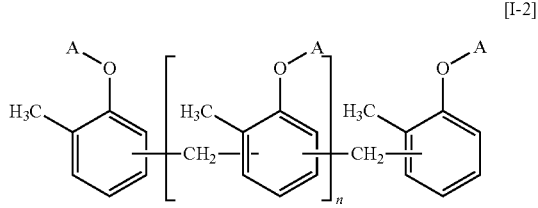
[I-3]
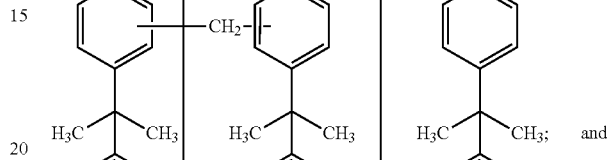
[I-4]
in the above Formula I-4, x is
—CH$_2$—, 
and in
R is a linear or branched alkyl group of C1-C10,
in the above Formulae I-1 to I-4, at least two of a plurality of A have a structure of the following Formula A2, and at least one of A has a structure of the following Formula A3, where in the case that at least one of A is A3, the remainder thereof have the following Formula B3 or hydrogen, in the above Formula I-1, in the case that Z is 1A to 1E, n is an integer of at least 2, and in the case that Z is 1F, n is an integer of at least 1, in the above Formulae 1-2 and 1-3, n is an integer of at least 1, in the above Formula I-4, in the case that x is

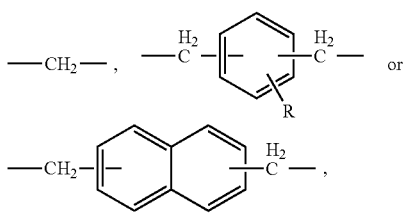

n is an integer of at least 2, and in the case that x is

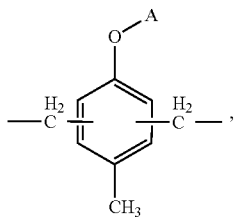

n is an integer of at least 1, in the above Formula I-4, p is 1 or 2,

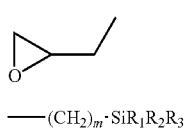 [Formula A2]

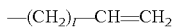 [Formula A3]

—(CH$_2$)$_m$-SiR$_1$R$_2$R$_3$ in the above Formulae A3, at least one of R$_1$ to R$_3$ is an alkoxy group having 1 to 5 carbon atoms, and the remainder thereof are an alkyl group having 1 to 10 carbon atoms, the alkoxy group and the alkyl group are a linear or a branched, and m is an integer from 3 to 10, —(CH$_2$)$_l$—CH=CH$_2$ [Formula B3]

in the above Formula B3, 1 is an integer from 1 to 8.

5. The epoxy composition of claim 4, further comprising at least one epoxy compound selected from the group consisting of a glycidyl ether-based epoxy compound, a glycidyl-based epoxy compound, a glycidyl amine-based epoxy compound, a glycidyl ester-based epoxy compound, a rubber modified epoxy compound, an aliphatic polyglycidyl-based epoxy compound and an aliphatic glycidyl amine-based epoxy compound.

6. The epoxy composition of claim 4, further comprising at least one filler selected from the group consisting of inorganic particles and a fiber.

7. The epoxy composition of claim 6, wherein the inorganic particle is at least one selected from the group consisting of a metal oxide selected from the group consisting of silica, zirconia, titania, alumina, silicon nitride and aluminum nitride, T-10 type silsesquioxane, ladder type silsesquioxane and cage type silsesquioxane.

8. The epoxy composition of claim 6, wherein the fiber is at least one glass fiber selected from the group consisting of an E-glass fiber, a T-glass fiber, an S-glass fiber, an NE-glass fiber, an E-glass fiber, an H-glass fiber, and quartz, and at least one organic fiber selected from the group consisting of a liquid crystal polyester fiber, a polyethyleneterephthalate fiber, a wholly aromatic fiber, a polyoxybenzasol fiber, a nylon fiber, a polyethylene naphthalate fiber, a polypropylene fiber, a polyether sulfone fiber, a polyvinylidene fluoride fiber, a polyethylene sulfide fiber and a polyether ether ketone fiber.

9. The epoxy composition of claim 6, wherein an content of the fiber is 10 wt % to 90 wt % based on a total solid content of the epoxy composition.

10. The epoxy composition according to claim 4, further comprising a curing agent.

11. The epoxy composition according to claim 4, further comprising an reaction catalyst for alkoxysilyl group.

12. The epoxy composition of claim 11, wherein the reaction catalyst for alkoxysilyl group is at least one selected from the group consisting of at least one inorganic acid selected from the group consisting of nitric acid, sulfuric acid, hydrochloric acid, acetic acid and phosphoric acid, ammonia, KOH, NH$_4$OH, amine, a transition metal alkoxide, and a tin compound.

13. The epoxy composition of claim 11, wherein the reaction catalyst is present in an amount of 0.01 phr to 10 phr based on the epoxy compound having an alkoxysilyl group.

14. The epoxy composition of claim 11, further comprising water.

15. A cured article of the epoxy composition according to claim 4.

16. The cured article of claim 15, wherein the cured article has a coefficient of thermal expansion (CTE) of less than or equal to 60 ppm/° C.

17. The cured article of claim 15, wherein the cured article has a glass transition temperature of 100° C. or above, or does not exhibit the glass transition temperature.

* * * * *